United States Patent [19]
Dickerman et al.

[11] Patent Number: 5,837,899
[45] Date of Patent: Nov. 17, 1998

[54] ULTRASONIC TESTING (UT) SYSTEM HAVING IMPROVED SIGNAL PROCESSING

[75] Inventors: Robert L. Dickerman, Northfield; Marc A. Camerlin, Westfield, both of Mass.; Stanley Klein, Cromwell, Conn.; Michel St. Martin, Springfield; David S. Leonard, Feeding Hills, both of Mass.

[73] Assignee: Combustion Enginineering, Inc., Windsor, Conn.

[21] Appl. No.: 714,926

[22] Filed: Sep. 13, 1996

Related U.S. Application Data

[60] Provisional application No. 60/003,882 Sep. 18, 1995.
[51] Int. Cl.[6] .................................................. G01N 29/04
[52] U.S. Cl. .............................. 73/610; 73/625; 73/628; 73/611; 73/612; 364/508; 364/550
[58] Field of Search ..................................... 364/507, 508, 364/550; 73/609–612, 613–616, 625, 626, 628, 602

[56] References Cited

U.S. PATENT DOCUMENTS

| | | | |
|---|---|---|---|
| 4,173,898 | 11/1979 | Forstermann et al. | 73/611 |
| 4,222,275 | 9/1980 | Sholl et al. | 73/636 |
| 4,234,937 | 11/1980 | Eggleton et al. | 367/11 |
| 4,970,637 | 11/1990 | Sato | 364/715.06 |
| 5,555,180 | 9/1996 | Hilger et al. | 364/577 |

FOREIGN PATENT DOCUMENTS

| | | |
|---|---|---|
| 2623892A1 | 12/1977 | Germany . |
| 3821102A1 | 1/1989 | Germany . |
| 62-135764 | 6/1987 | Japan . |
| 7225223 | 8/1995 | Japan . |
| 2279523A | 1/1995 | United Kingdom . |

Primary Examiner—Hezron E. Williams
Assistant Examiner—Rose M. Miller
Attorney, Agent, or Firm—Ronald P. Kananen; John H. Mulholland

[57] ABSTRACT

An ultrasonic testing system can receive data from at least two ultrasonic transducers and process the data in parallel to each other. The testing system can compress the data by a fixed ratio by storing the value of the sample having the highest-amplitude out of a group of samples. The testing system can also provide threshold-based run-length encoding by compressing data by only storing samples which exceed a user-defined threshold value as well as a user-defined range of samples surrounding said samples. The ultrasonic testing system also provides a hardware gate for storing a peak amplitude and associated time-of-flight for a user-defined interval and a gate for storing the time-of-flight for the first excursion of the data through a user-defined threshold and interval. The operation of these gates or the storage of waveform data may be delayed by a constant delay or until the data exceeds a user-selectable threshold during a user-selectable time interval. The system also provides a multi-channel design allowing simultaneous waveform and/or hardware gate acquisition of data on more than one channel and permitting the parallel processing of data.

25 Claims, 85 Drawing Sheets

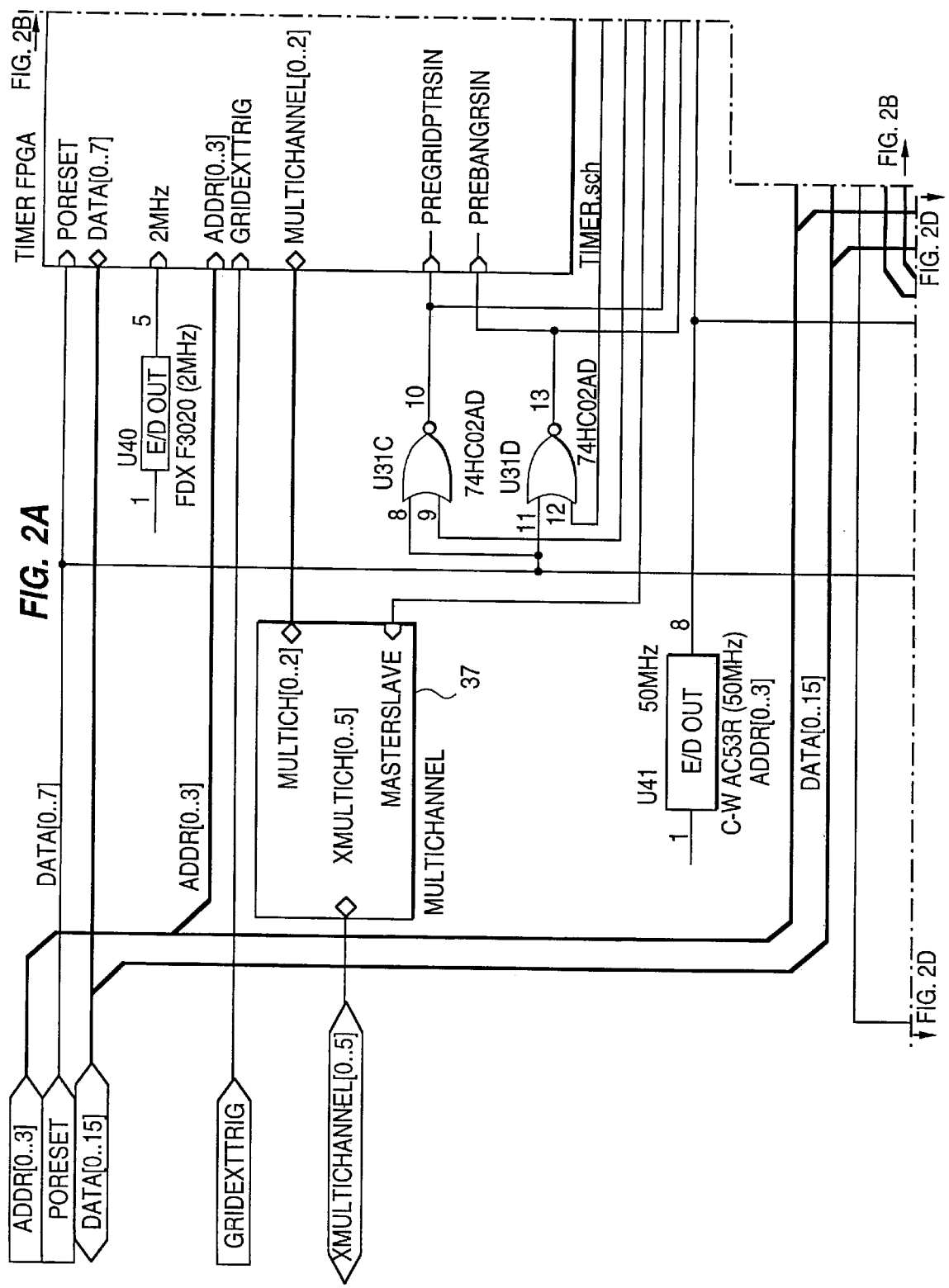

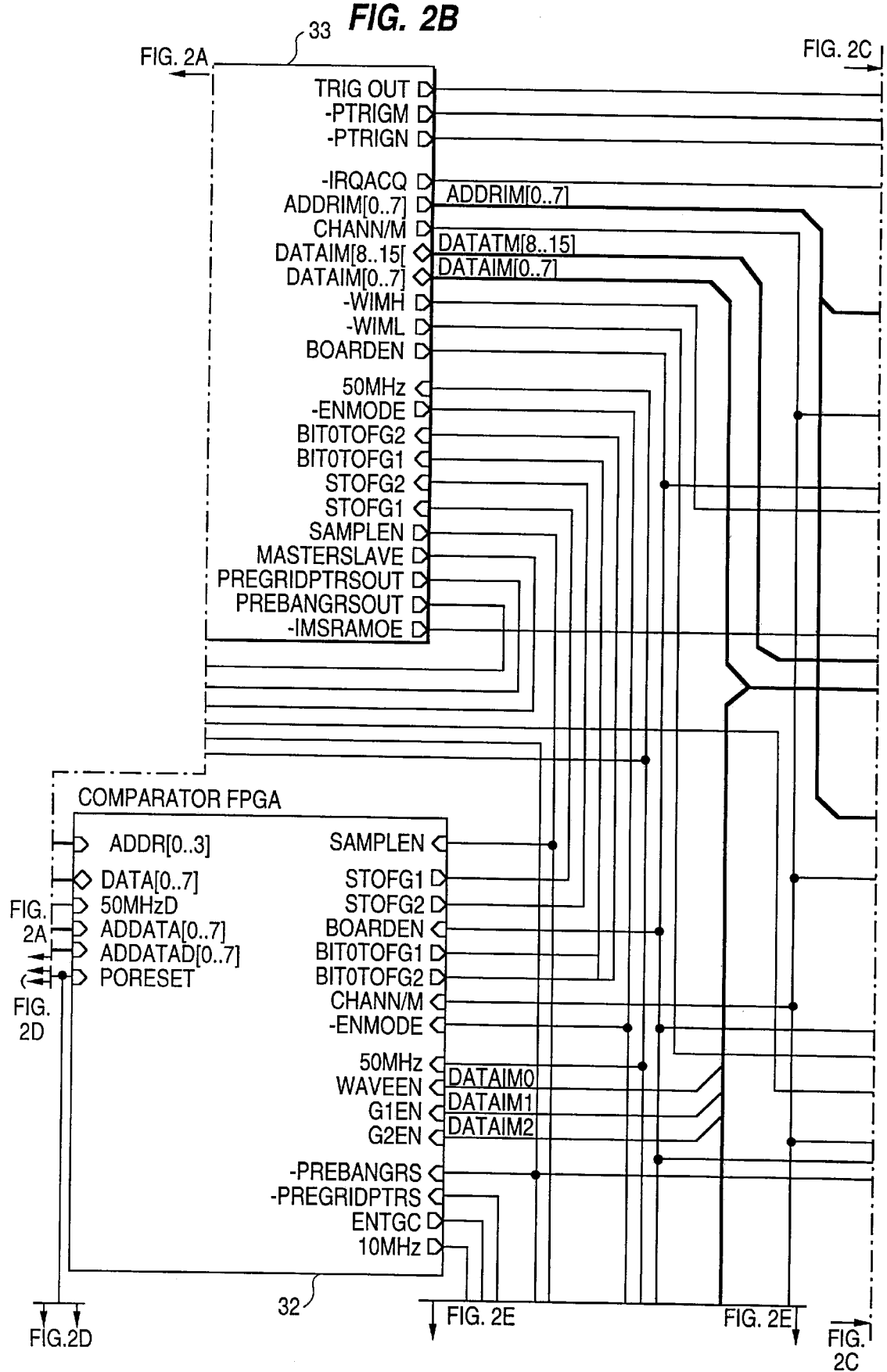

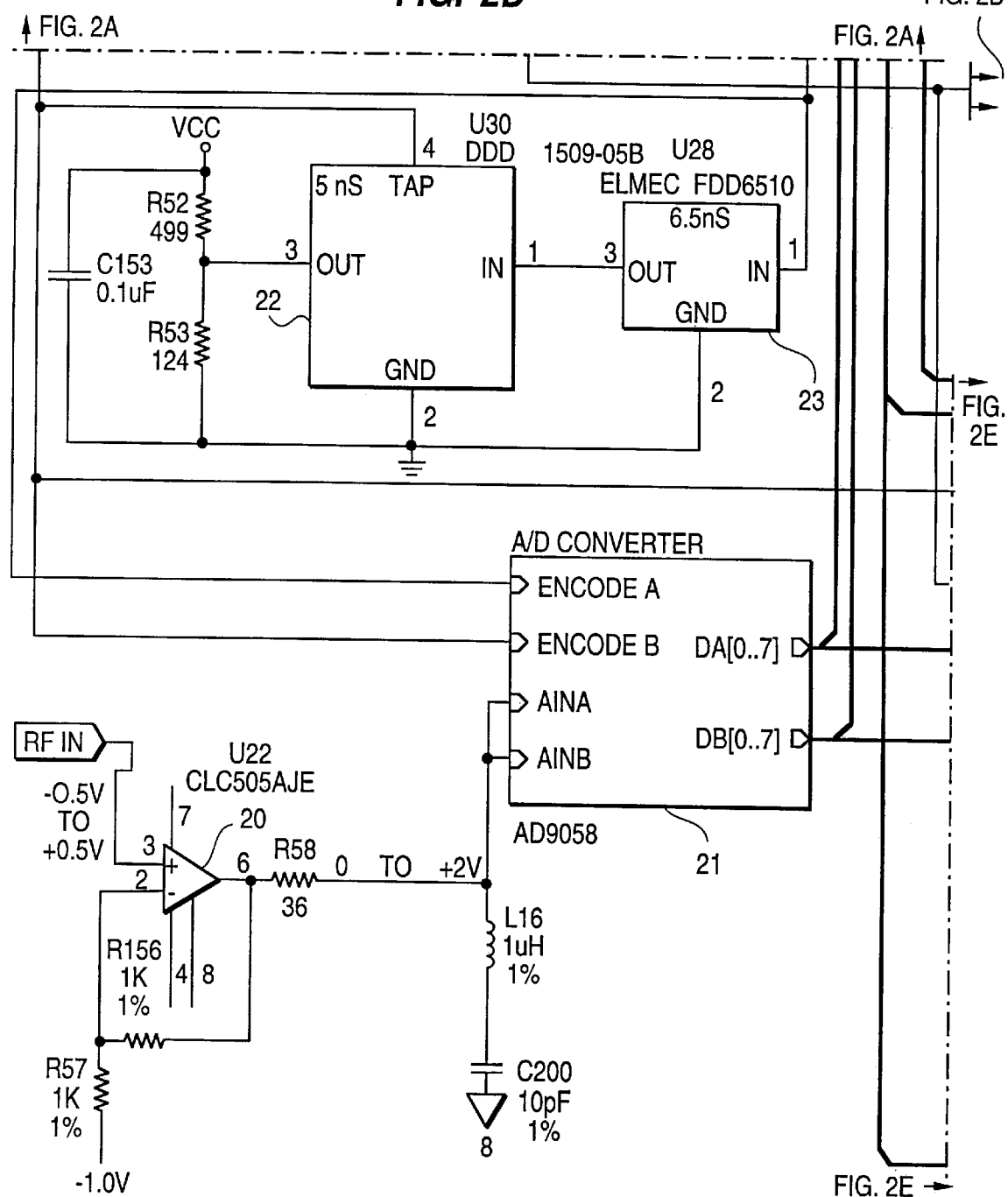

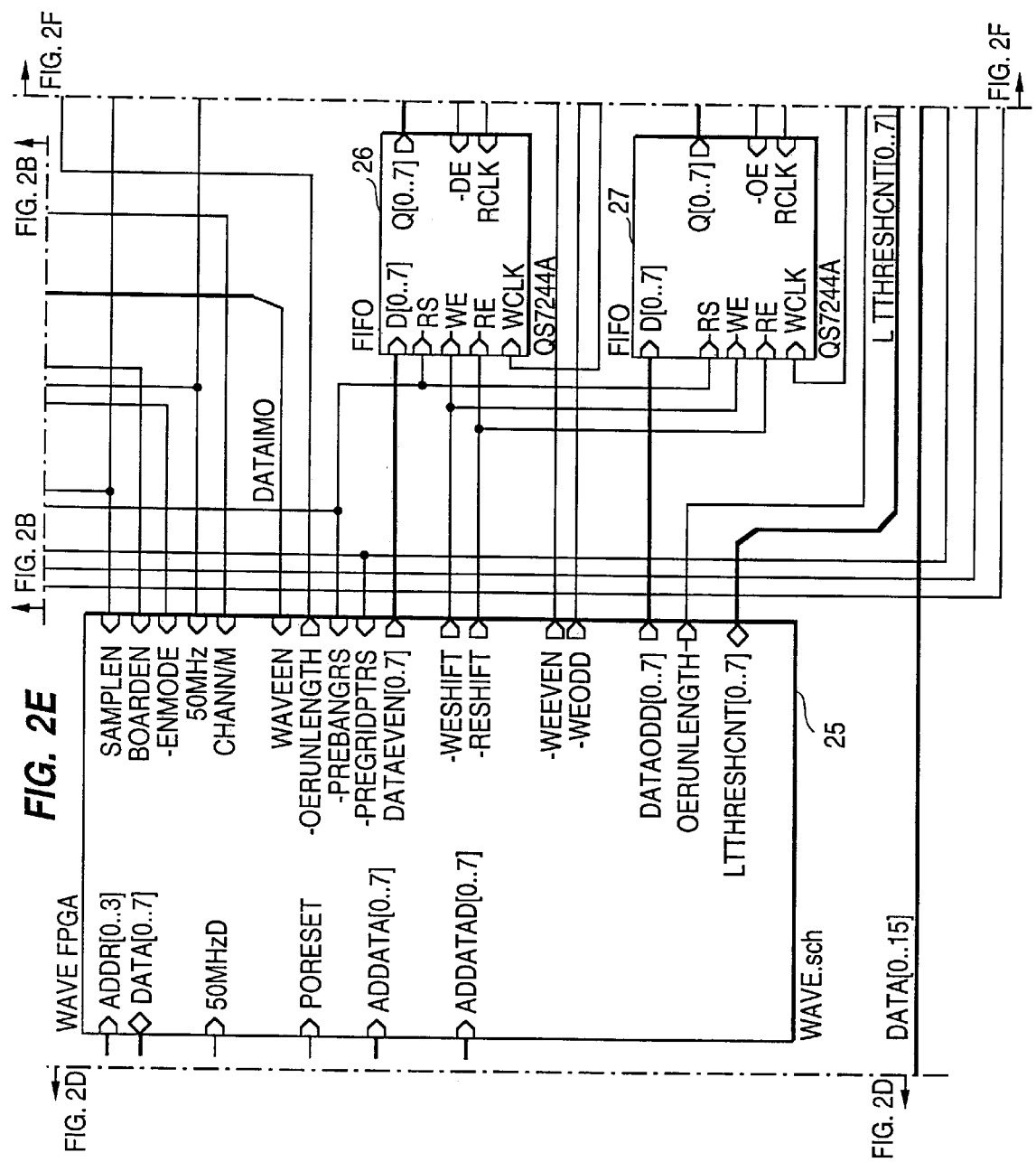

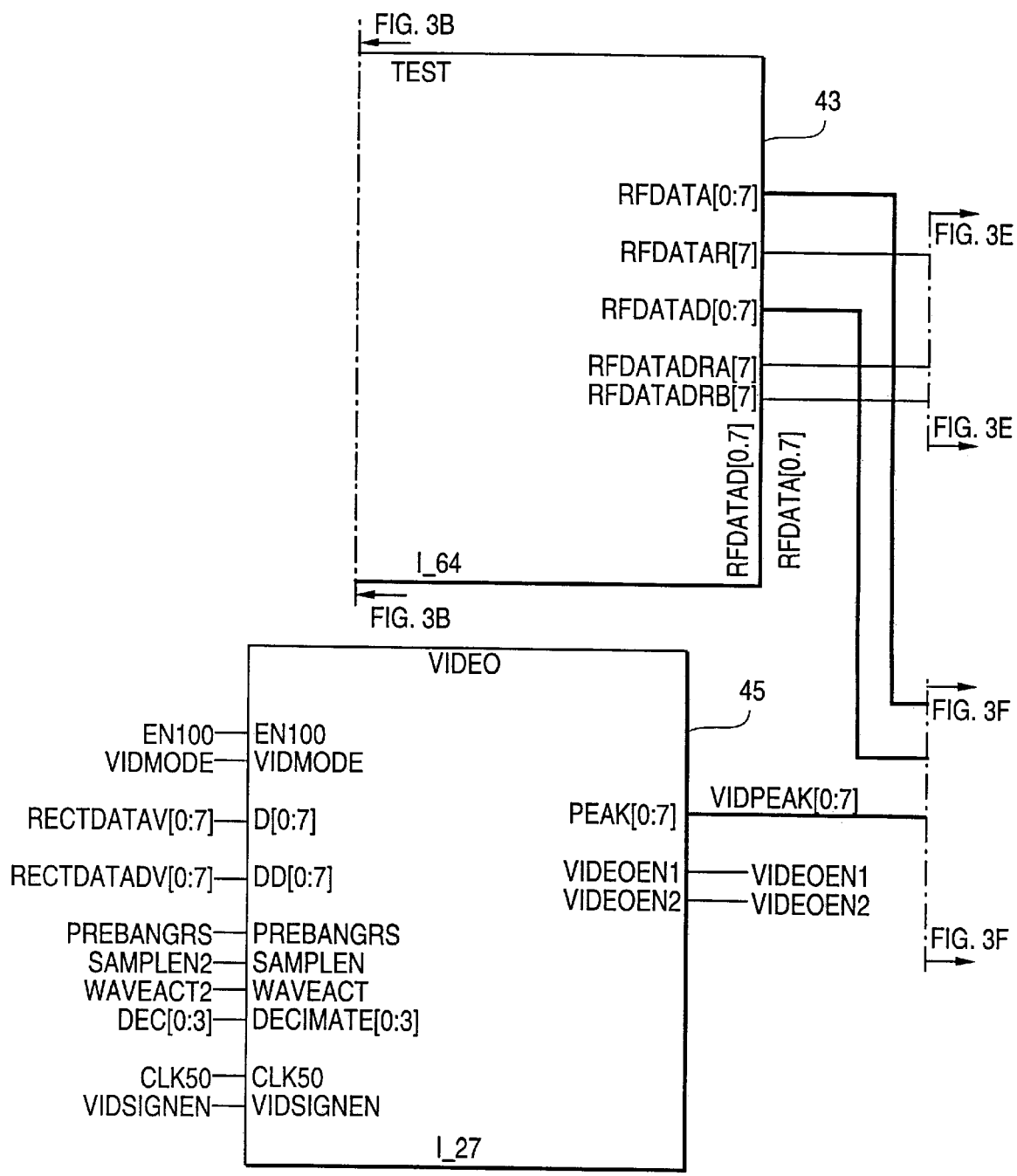

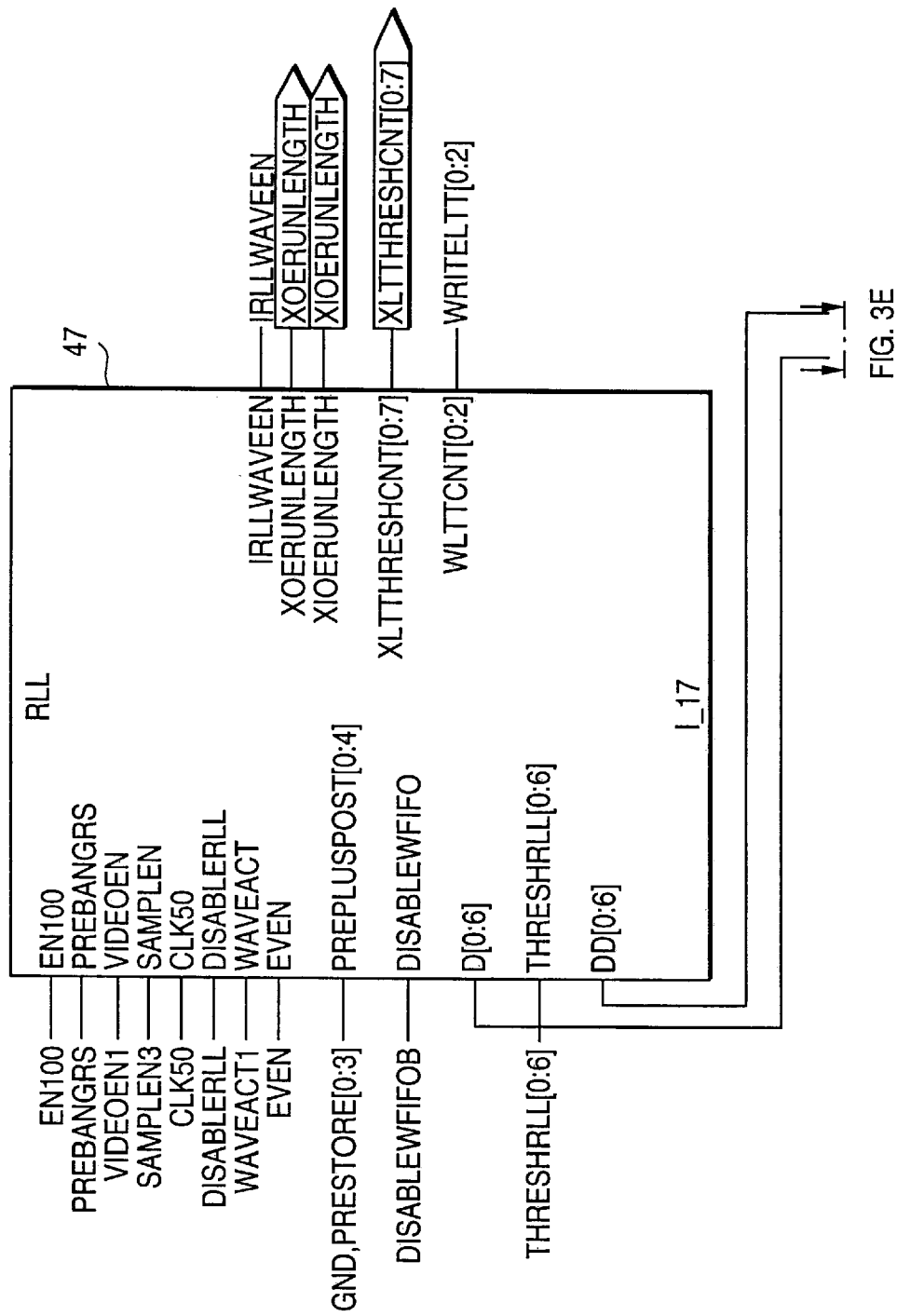

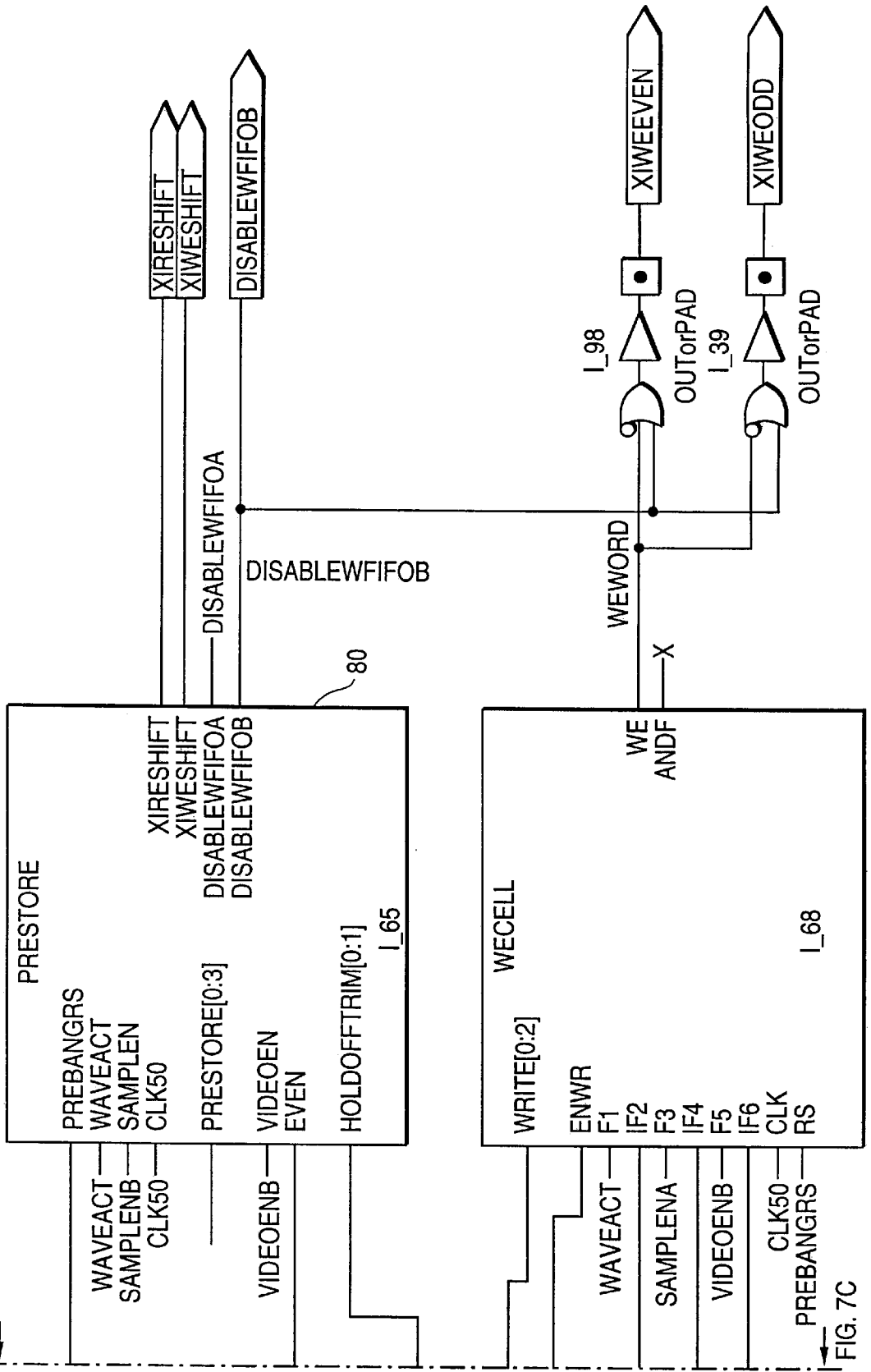

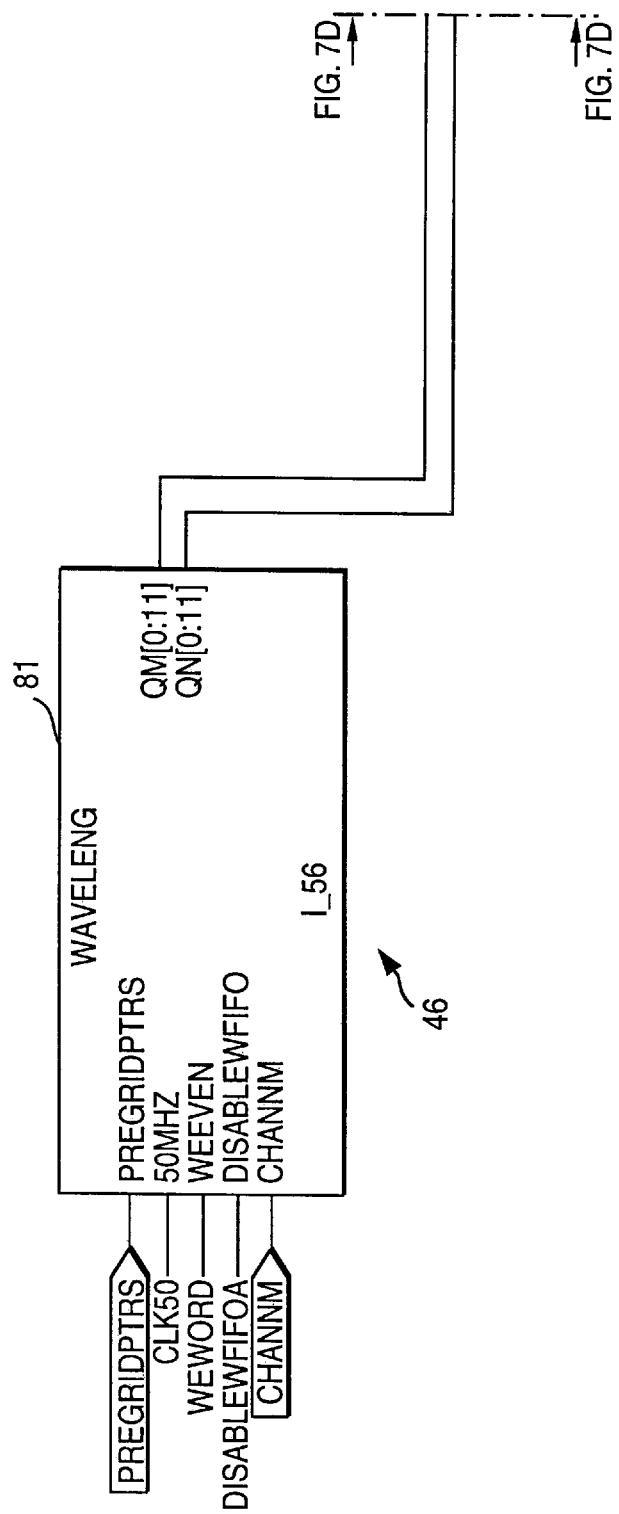

SHIFT REGISTER PRESTORE GENERATOR

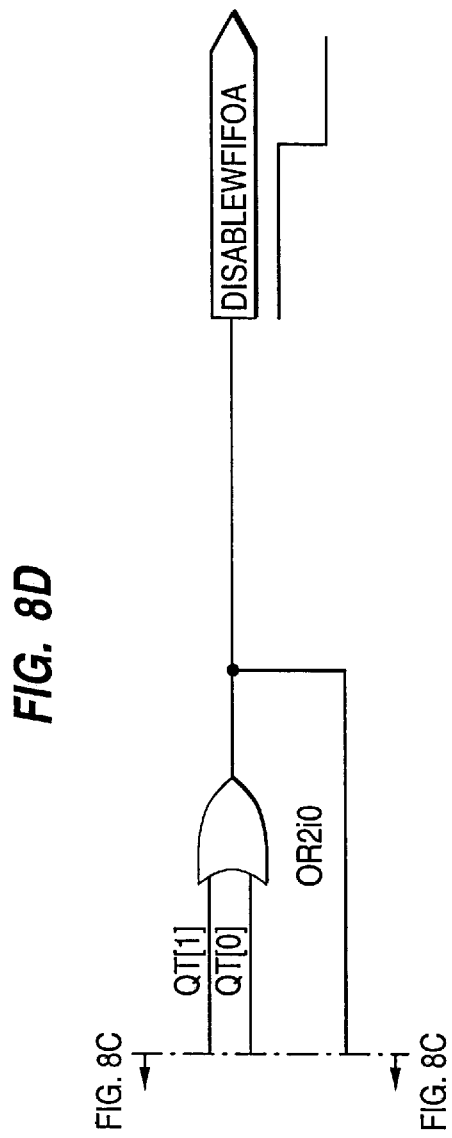

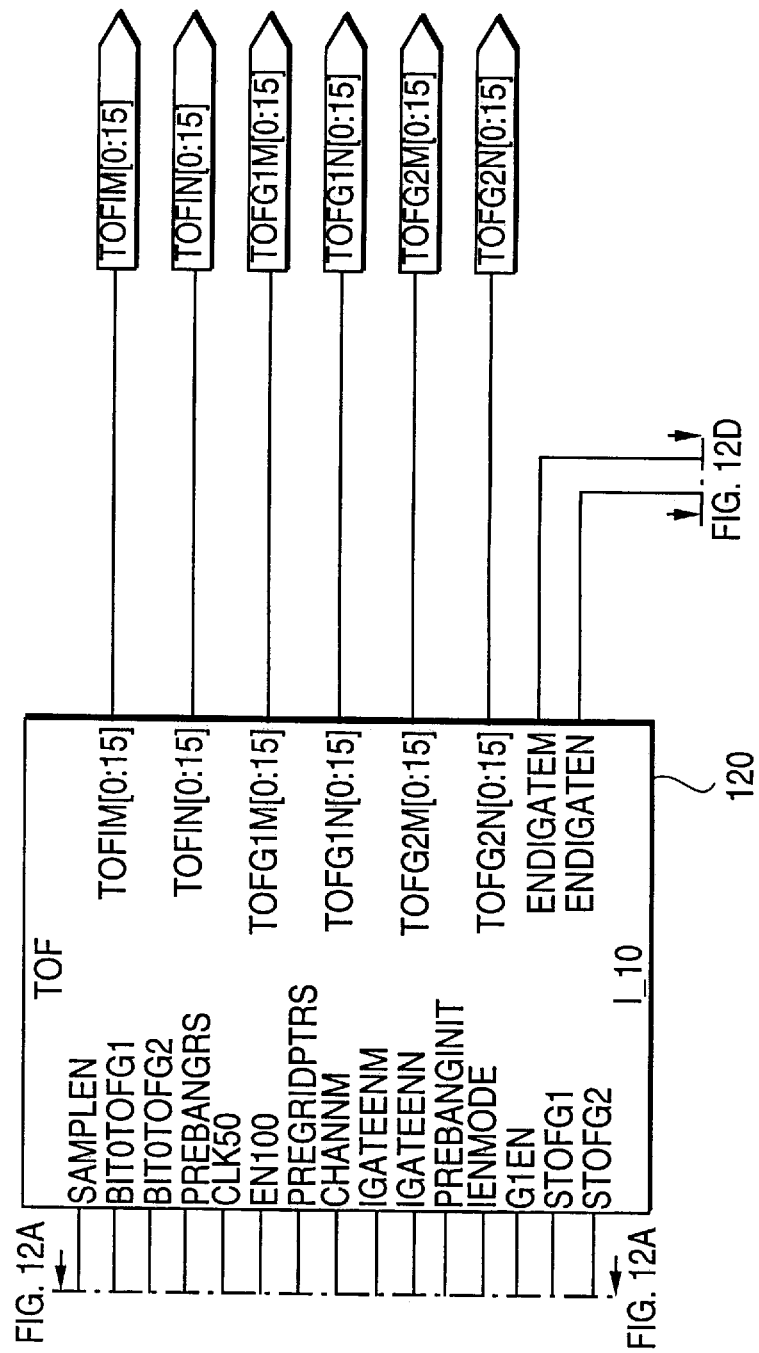

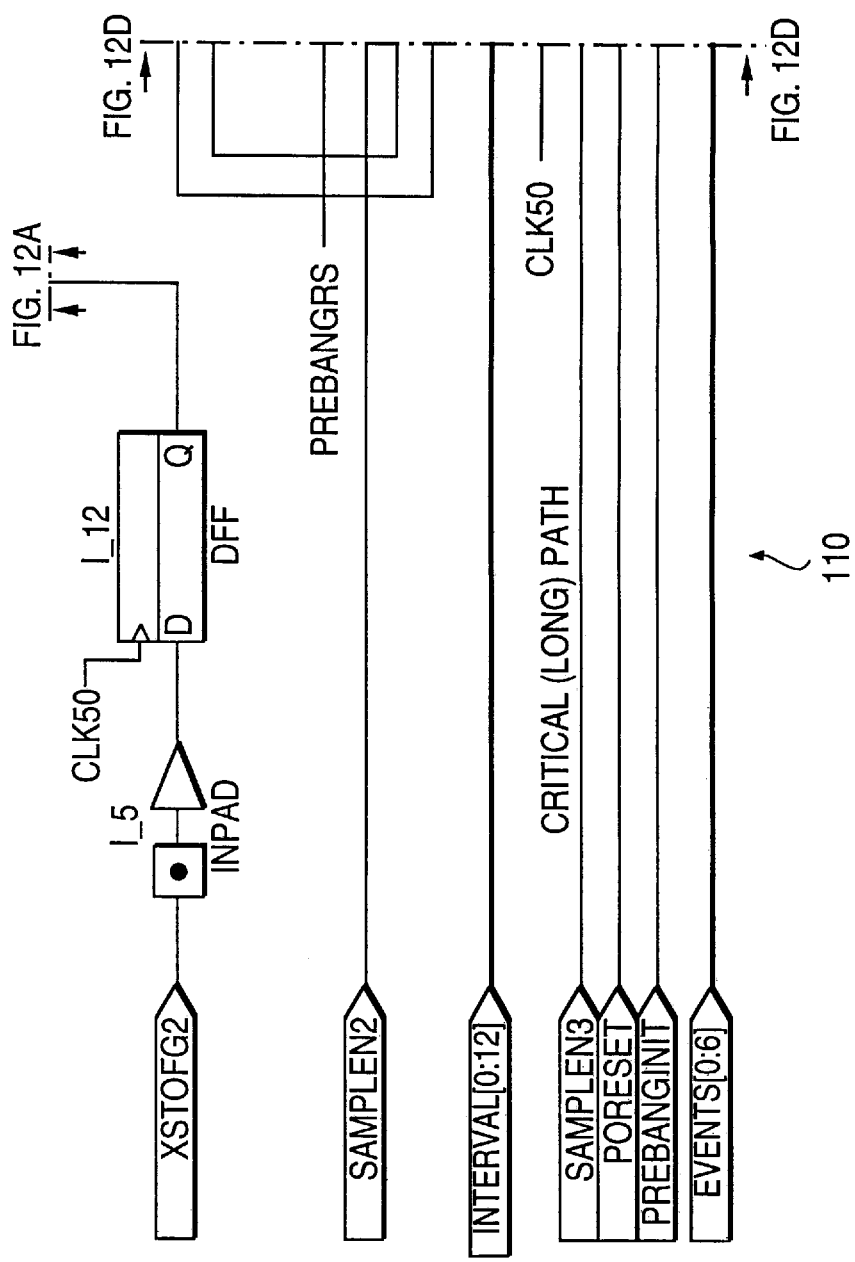

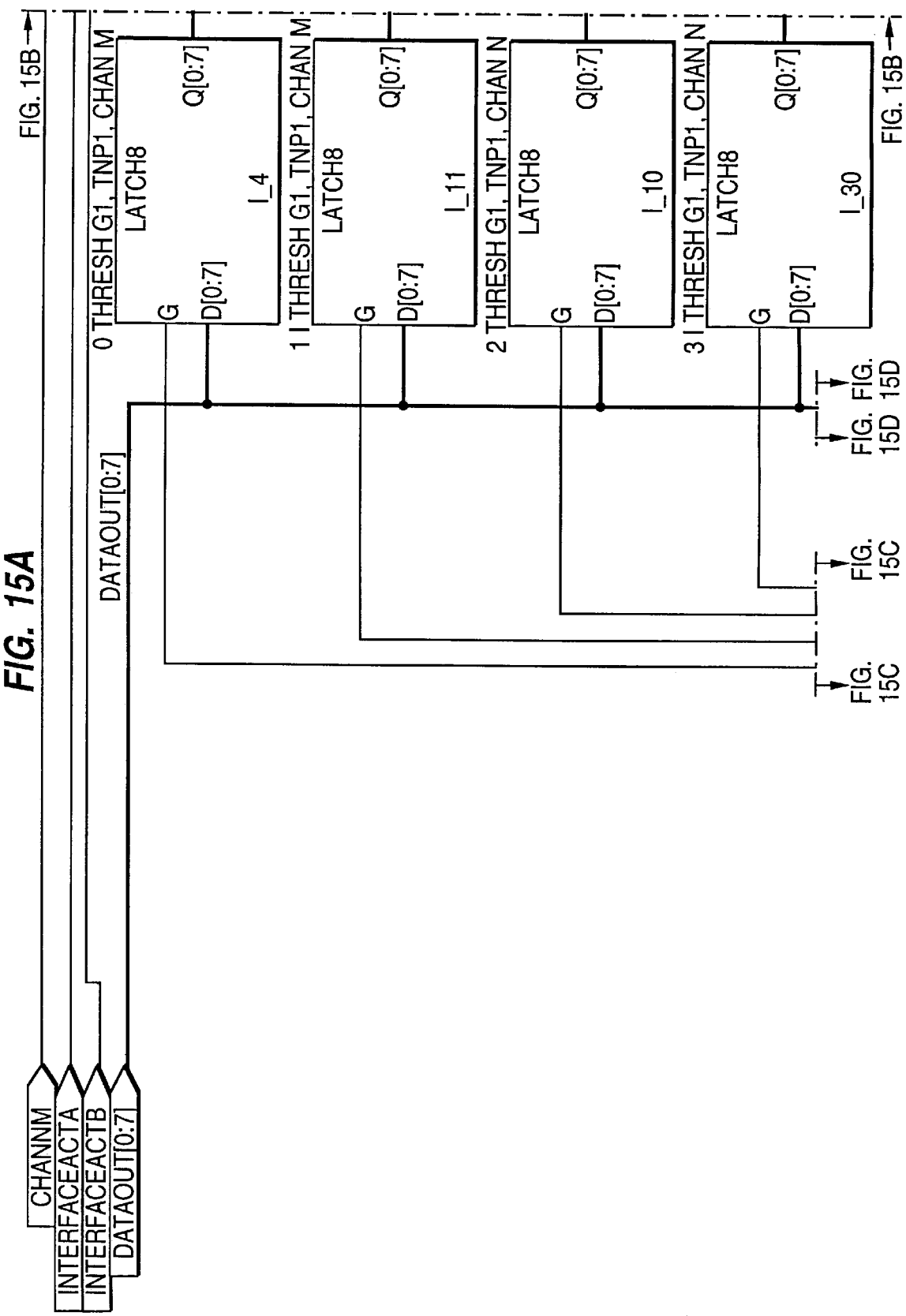

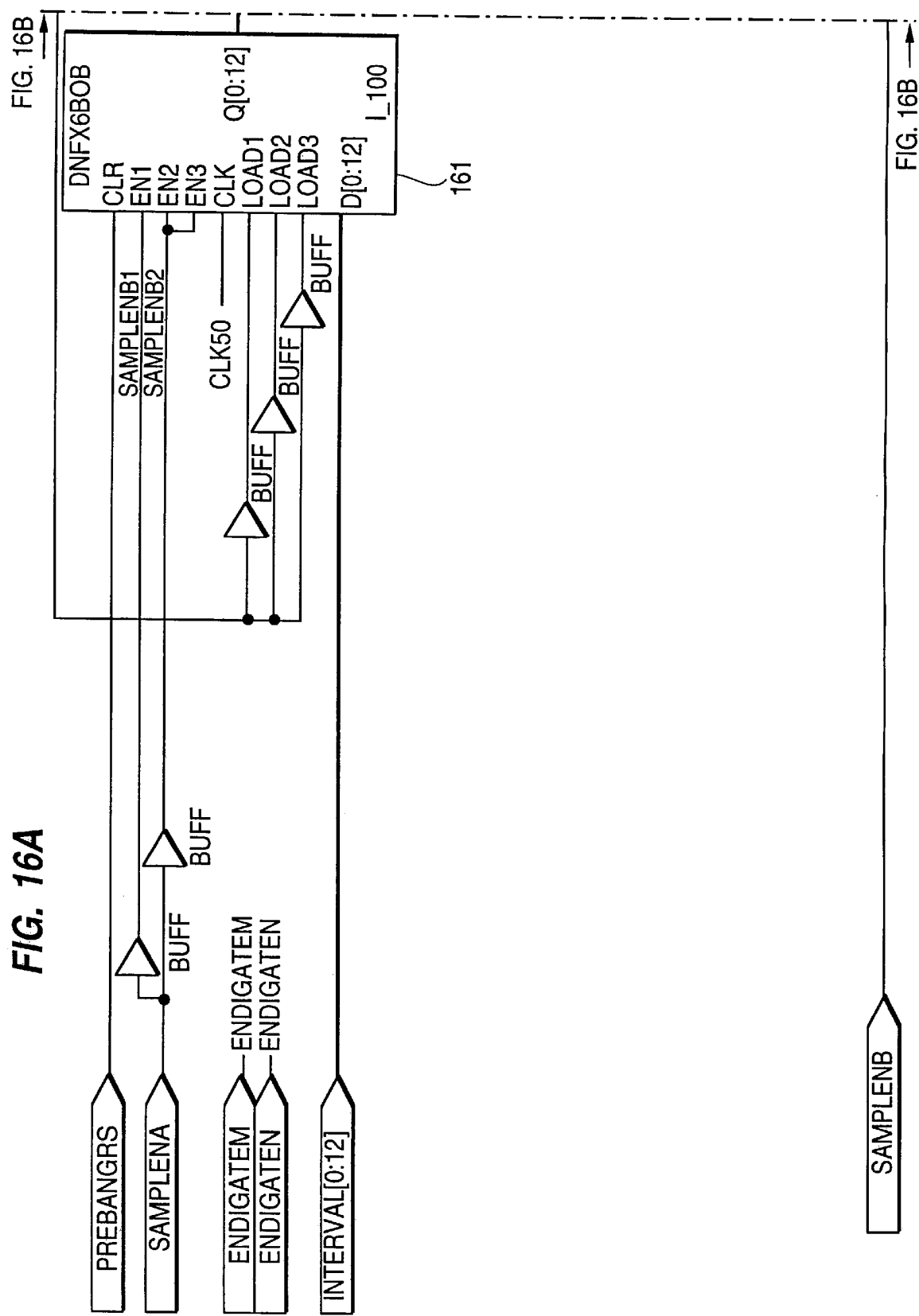

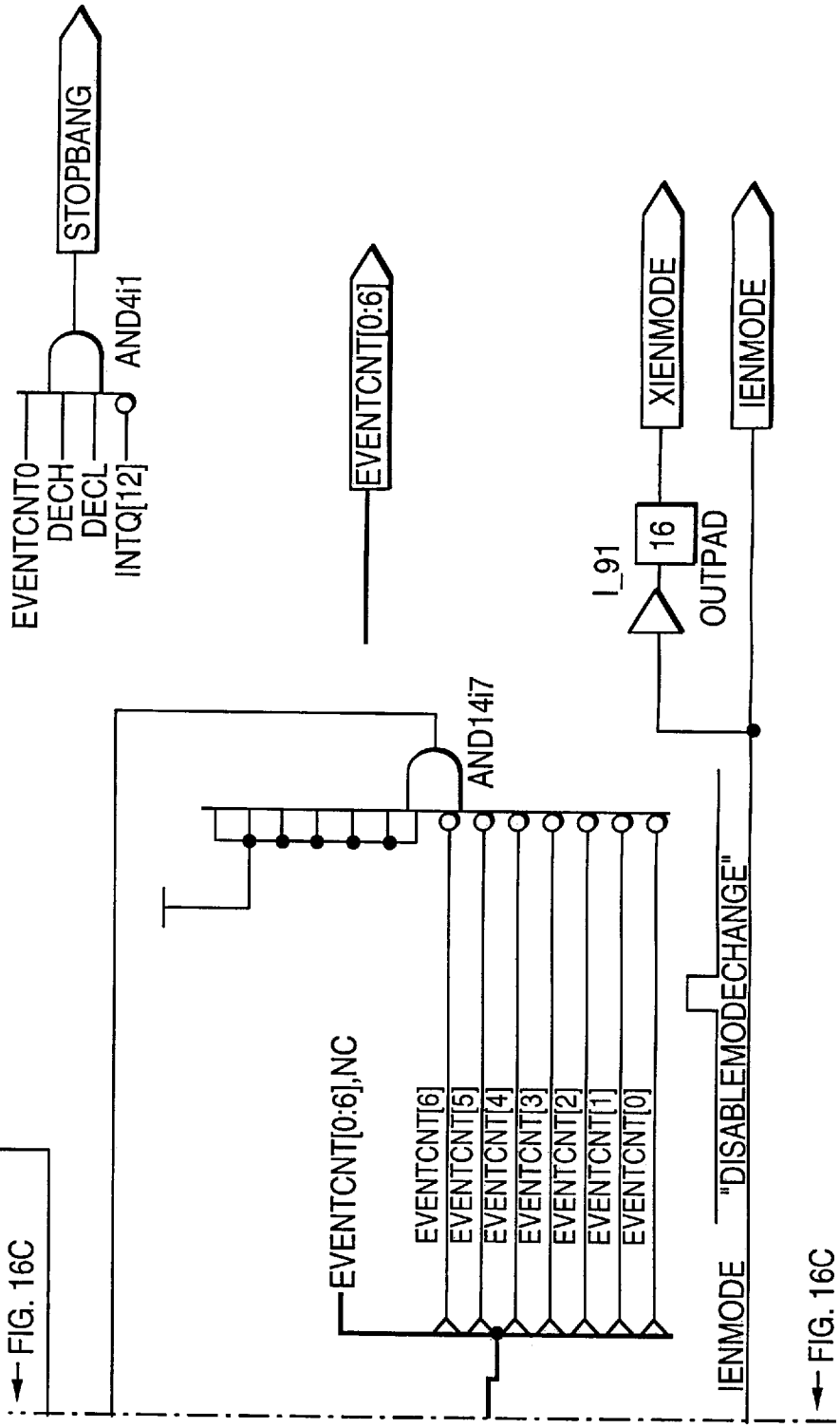

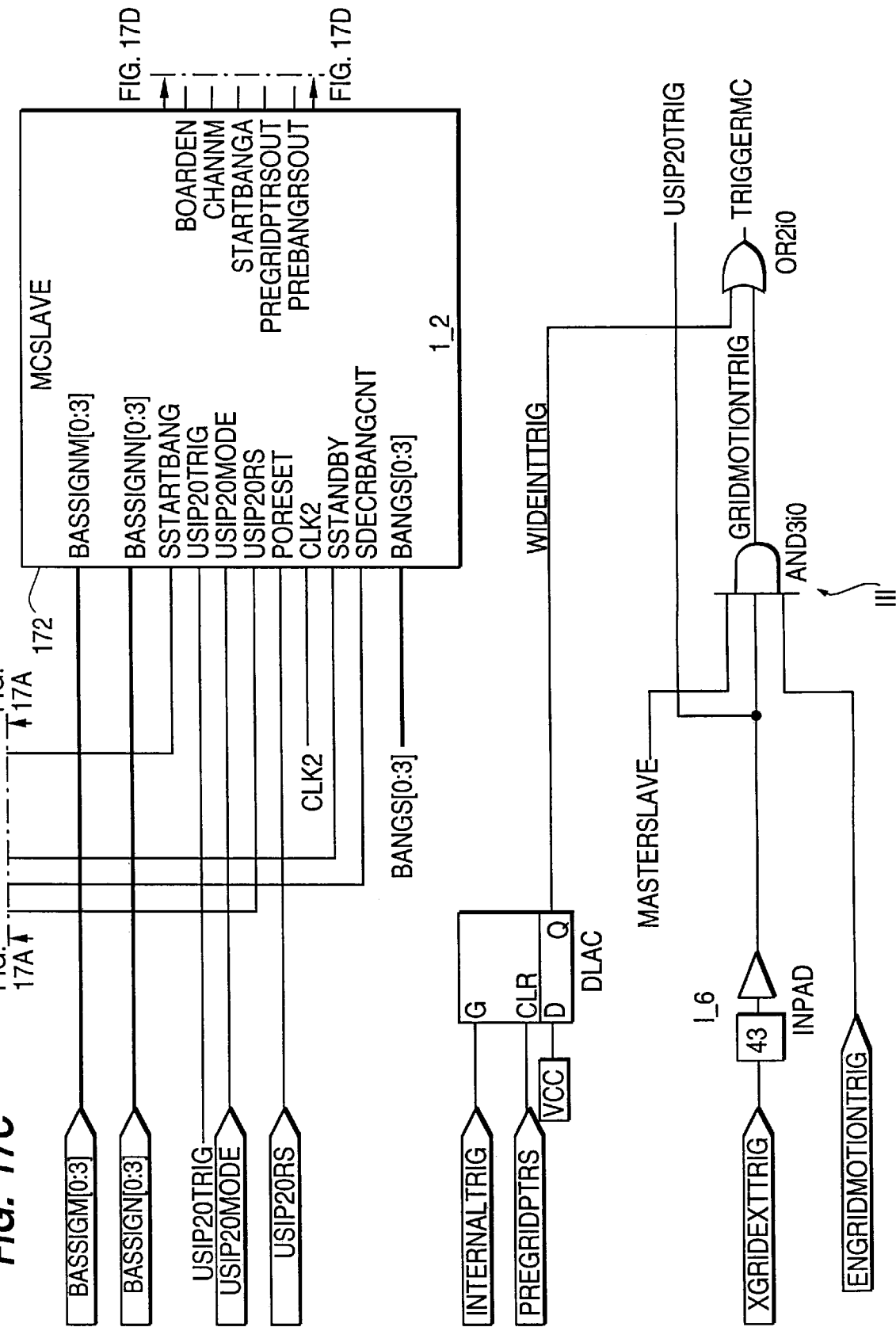

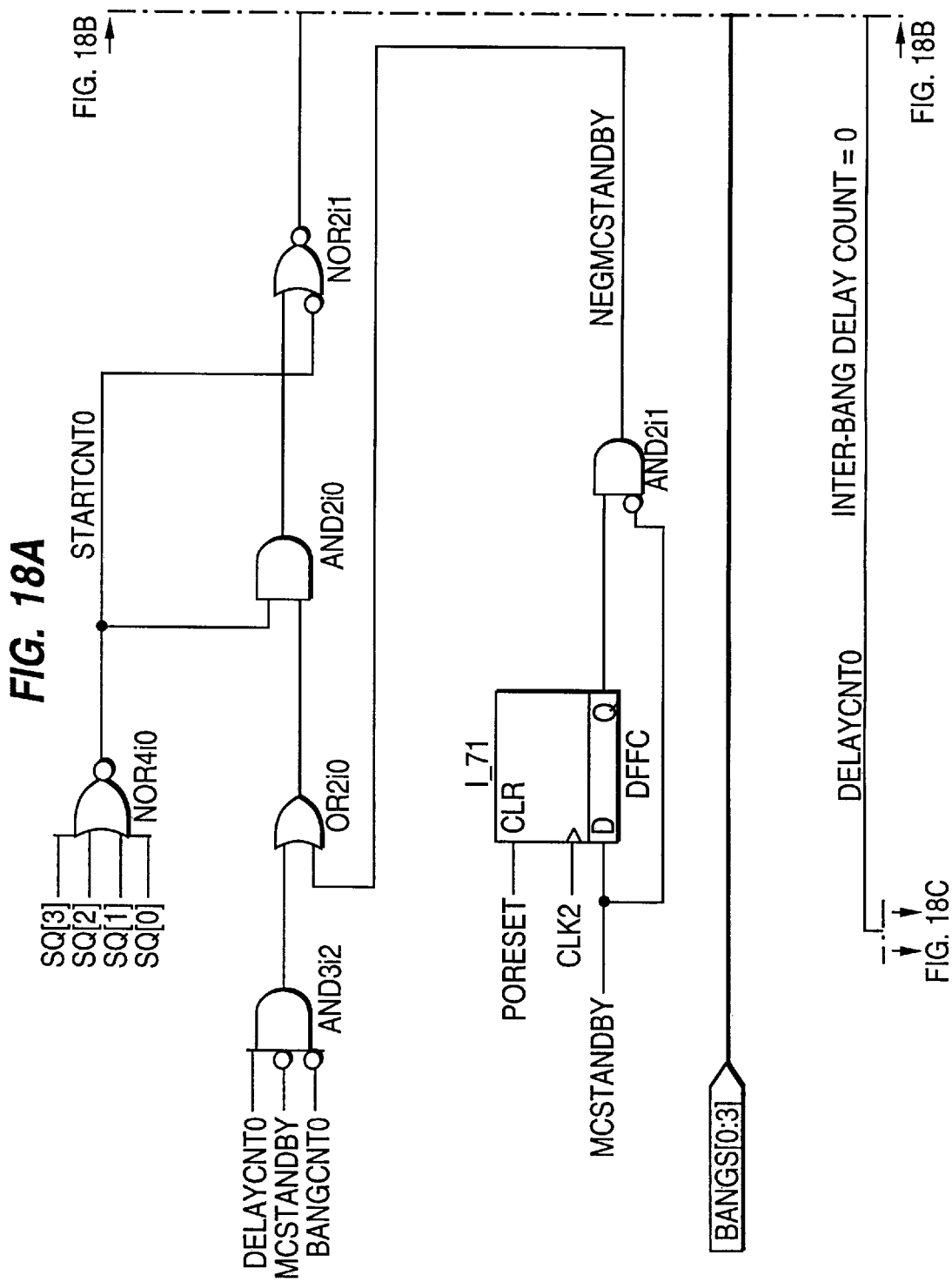

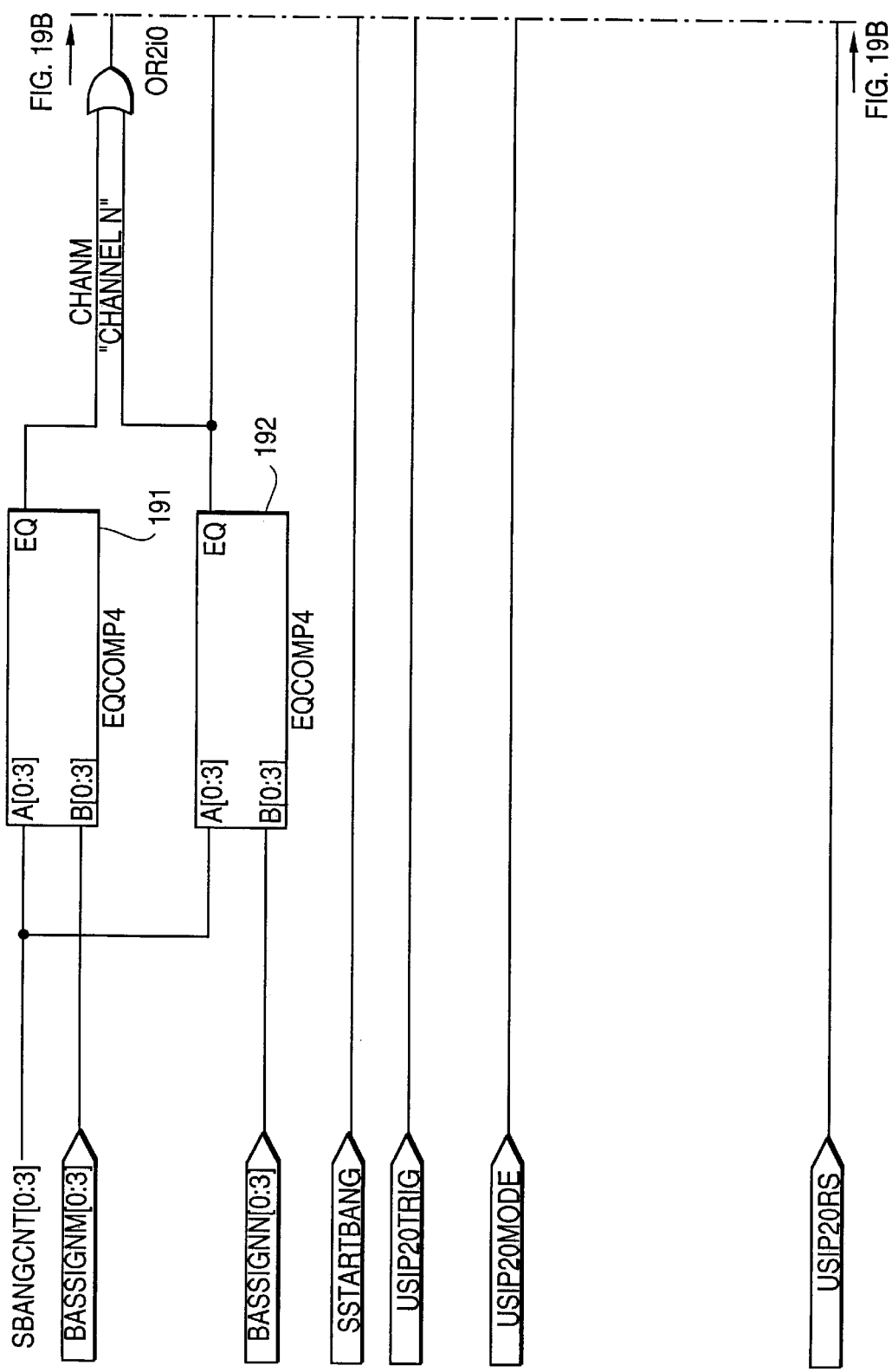

ULTRASONIC TESTING (UT) SYSTEM HAVING IMPROVED SIGNAL PROCESSING

BACKGROUND OF THE INVENTION

1. Field of the Invention

The invention generally relates to an ultrasonic testing system and, more particularly, to an ultrasonic testing system for use in non-destructive image testing using A/D conversion of ultrasonic sensor signals to digital signals.

2. Description of the Prior Art

Non-invasive ultrasonic testing systems are known for a number of uses, such as flaw detection and structural integrity. Typically, ultrasonic testing systems have a single channel of analog data acquisition and data processing capability. The received analog data is converted into a digital format and is processed prior to displaying an image. Because scan rates are preferably as fast as possible and due to the large areas scanned, large amounts of digital data are stored and processed by the ultrasonic testing systems. The flaws and structural defects, however, usually only occupy a small proportion of the area scanned by the ultrasonic test probe and thus only a small fraction of the overall stored data. As a result of this large amount of data, the conventional ultrasonic testing systems have required large storage and processing capability for only a minimum amount of pertinent data.

In addition to requiring a large storage and processing capability, the large amounts of data that are stored and processed render it difficult to quickly process the data using general purpose computers and software. It is therefore a problem in the prior art to be able to quickly scan parts for which large amounts of data are required, particularly if any sort of data compression is required.

While some ultrasonic testing systems can accommodate more than one channel, these systems typically time-multiplexed the signals from the different channels together. These systems still required a large storage area and, due to the additional channel capability, were usually larger, bulkier, and more expensive. The multiple channel testing systems, however, were still relatively slow due to the fact that they typically convert only one channel at a time to digital data, and required the general purpose computer hardware and software to process large quantities of raw data.

BRIEF SUMMARY OF THE INVENTION

It is an object of the invention to provide an ultrasonic testing system which can provide a real-time view of scanned area with a superior price-performance ratio.

It is another object of the invention to provide an ultrasonic testing system which can compress data in received ultrasonic transducer signals.

It is another object of the invention to provide an ultrasonic testing system which can compress data in received ultrasonic transducer signals, and store only data in, or near excursions above a threshold value.

It is a further object of the invention to provide an ultrasonic tester providing a digital hardware gate.

It is yet a further object of the invention to quickly process data from more than one channel.

Additional objects, advantages and novel features of the invention will be set forth in the description which follows, and will become apparent to those skilled in the art upon reading this description or practicing the invention. The objects and advantages of the invention may be realized and attained by the appended claims.

To achieve the foregoing and other objects, in accordance with the present invention, as embodied and broadly described herein, an ultrasonic testing circuit has a pulsing circuit for stimulating an ultrasonic transducer with a voltage signal and for receiving an analog data signal from the transducer. An analog-to-digital converter receives the analog signal and converts the analog data signal into digital data. A timing circuit defines delay and sampling intervals. A counter circuit defines groups of digital data samples, preferably 2 to 16 or more. After the specified delay, a peak detector circuit acquires a peak value for each of the groups of digital data samples. The peak values for each group are then stored, whereby the waveform data becomes compressed, preferably by a factor of 2 to 16 or more.

In another aspect of the invention, the sampling interval is defined to be a period of starting time before and ending time after an excursion of the digital data above a user-defined threshold during a user-defined search interval. In this manner, the ultrasonic testing system provides threshold-based run-length encoding of the digital data, compressing the data by an additional factor of up to 128:1.

In yet further aspects of the invention, the ultrasonic testing system provides digital hardware gates for the storage of certain data. The hardware gate may search a received ultrasonic transducer signal and store the peak amplitude and polarity and the time-of-flight associated with the peak for a user-defined interval. The hardware gate may alternatively search the signal and store the time-of-flight corresponding to the first excursion of the signal through a user-defined threshold during a user-defined interval. These gates may be delayed or the waveform storage may be delayed until the transducer signal exceeds a user-defined threshold during a user-defined period of time.

In another aspect of the invention, an ultrasonic testing system receives more than one analog signal from a respective number of ultrasonic transducers. The data is converted into digital data with the data from one transducer being delayed relative to the data from at least one other transducer. In this manner, more than one data signal can be processed in parallel with the others and can quickly provide a display of the results in real-time.

These and other features of this invention will become apparent from a detailed review of this specification, taken in conjunction with the accompanying drawings and the written description.

BRIEF DESCRIPTION OF THE DRAWINGS

The accompanying drawings, which are incorporated in, and form a part of, the specification, illustrate embodiments of the present invention and, together with the description, serve to explain the principles of the invention.

In the drawings.

DETAILED DESCRIPTION OF THE PREFERRED EMBODIMENTS

Reference will now be made in detail to the preferred embodiment of the invention, an example of which is illustrated in the accompanying drawings.

Figure 1A:
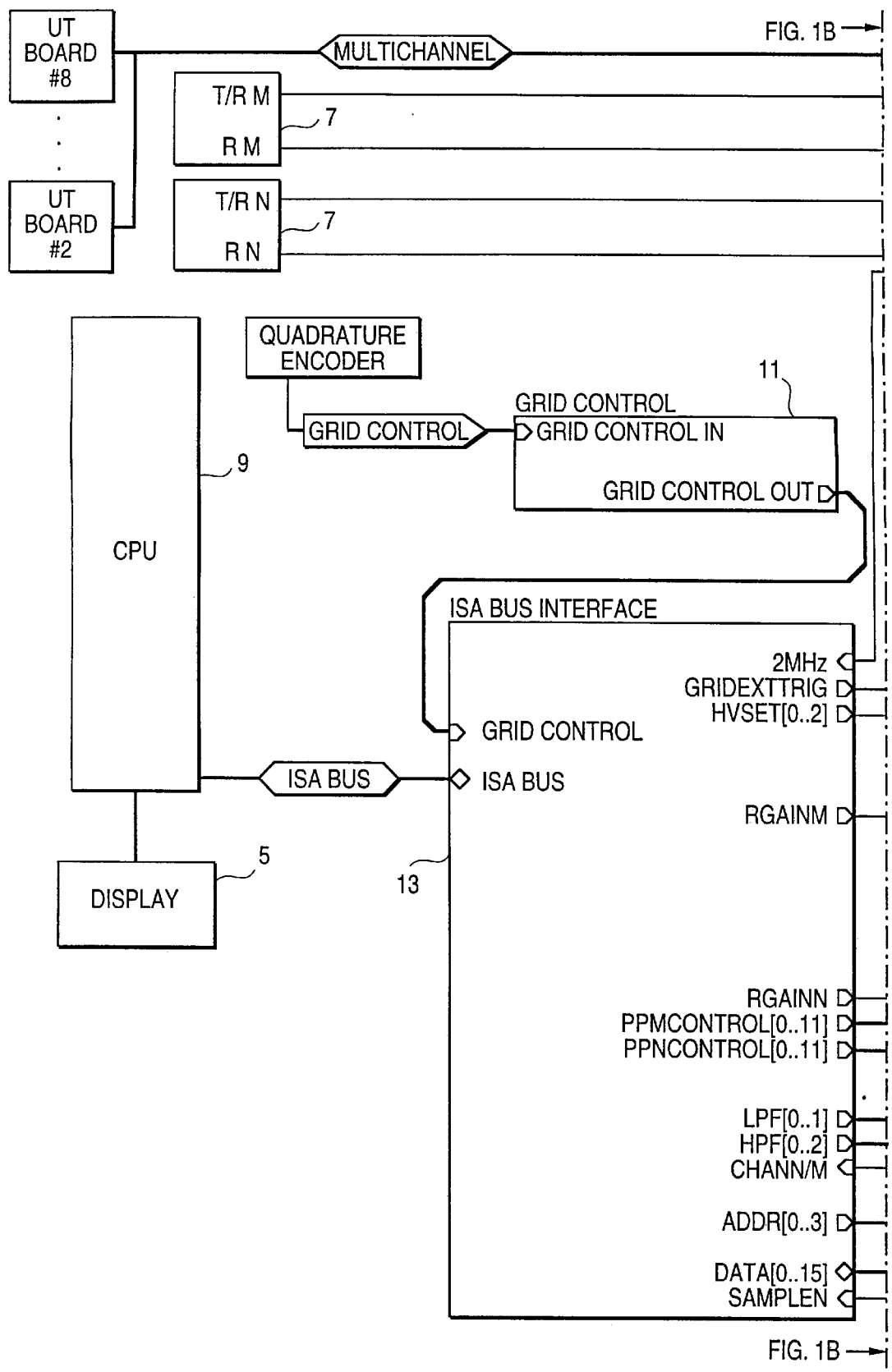
FIG. 1 (comprising FIGS. 1A, 1B and 1C) is a block diagram of an ultrasonic testing system according to a preferred embodiment of the invention.
Figure 1B:
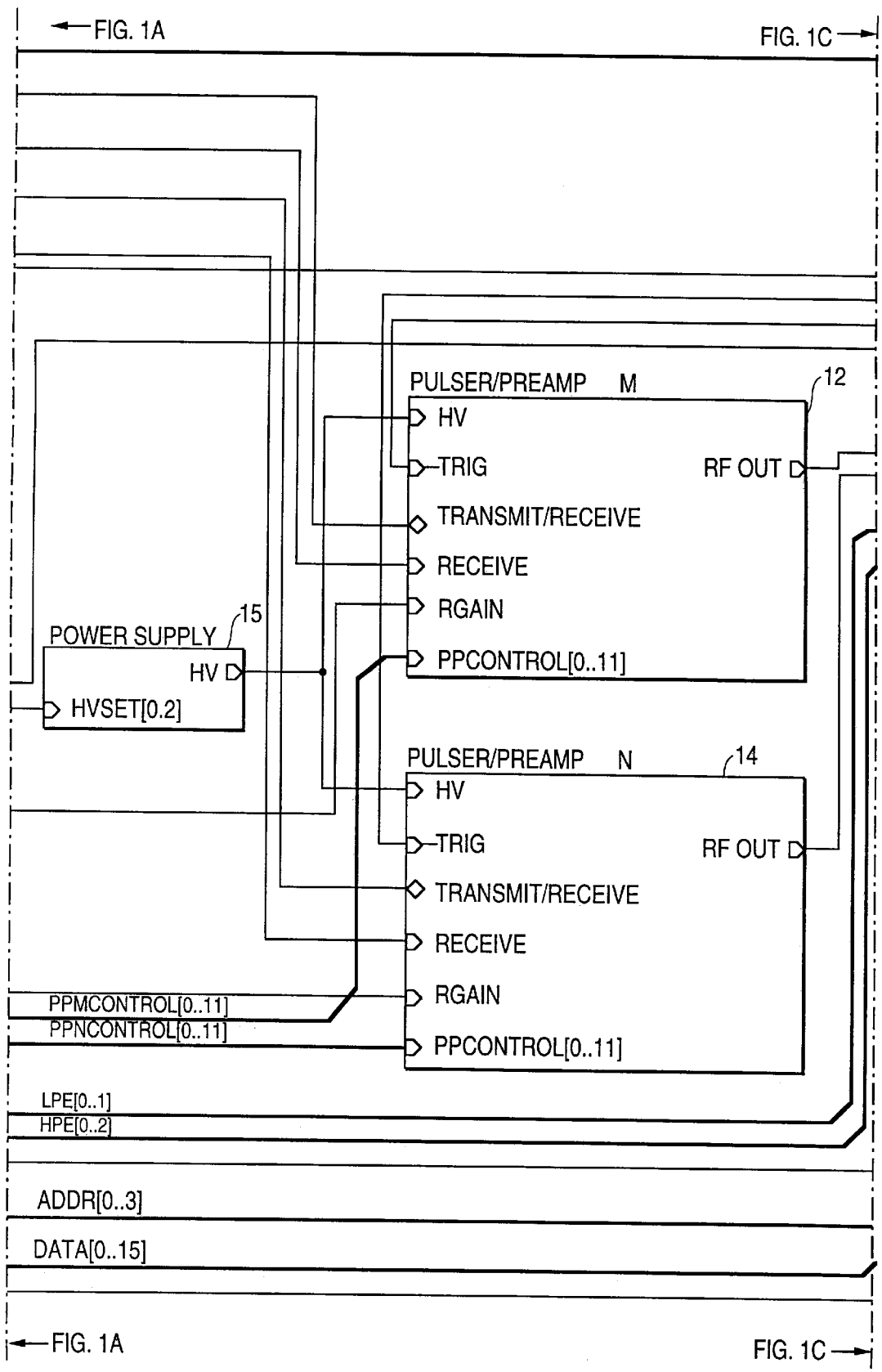
Figure 1C:
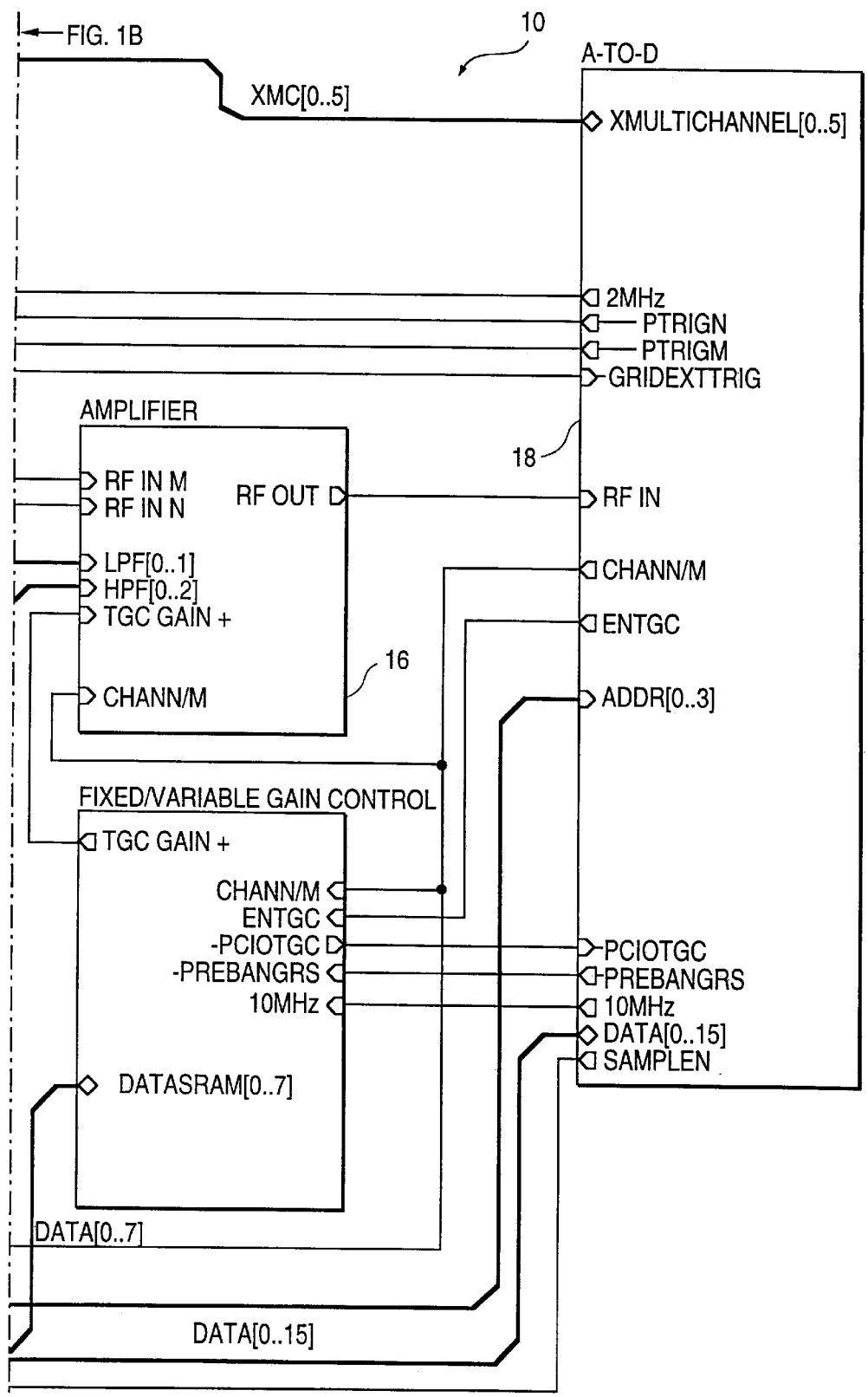

With reference to FIG. 1, an ultrasonic testing system 10 according to the invention comprises a central processing unit (CPU) 9 which can be connected to a plurality of boards. While the exemplary system 10 of FIG. 1 has eight boards, it should be understood that the system 10 may have a greater or lesser number of boards. Each board comprises a pair of pulser and pre-amp circuits 12 and 14, each of which is connected directly to an ultrasonic transducer 7. Each of the pulser and pre-amp circuits 12 and 14 has a pulsing circuit which is capable of stimulating the ultrasonic transducer 7 with a high voltage pulse and has a pre-amp circuit which can amplify the resultant returning signals from the ultrasonic transducer 7. The pulser and preamp circuits 12 and 14 generate RF output signals which are multiplexed into one second stage amplifier 16 which has an output connected to an A-to-D converter 18. Each board in the ultrasonic testing system 10 further comprises a grid control circuit 11, an ISA bus interface circuit 13, and a power supply 15. The system 10 further includes a display 5 for displaying the results of a scan and, although not shown, includes any suitable input device, such as a keyboard or mouse.

Figure 2C:
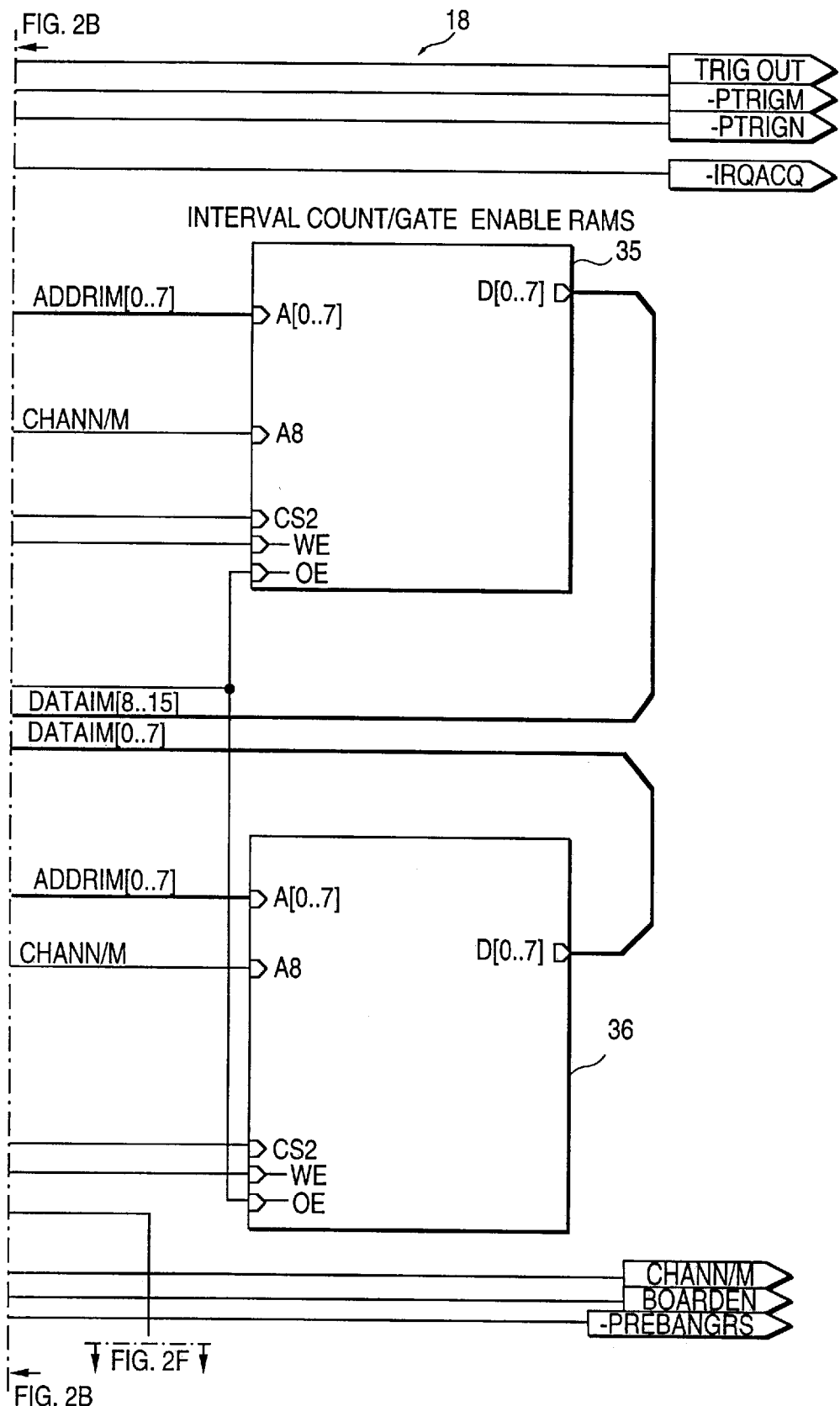
FIG. 2 (comprising FIGS. 2A, 2B, 2C, 2D, 2E and 2F) is a block diagram of an A/D converter shown in FIG. 1.
Figure 2F:
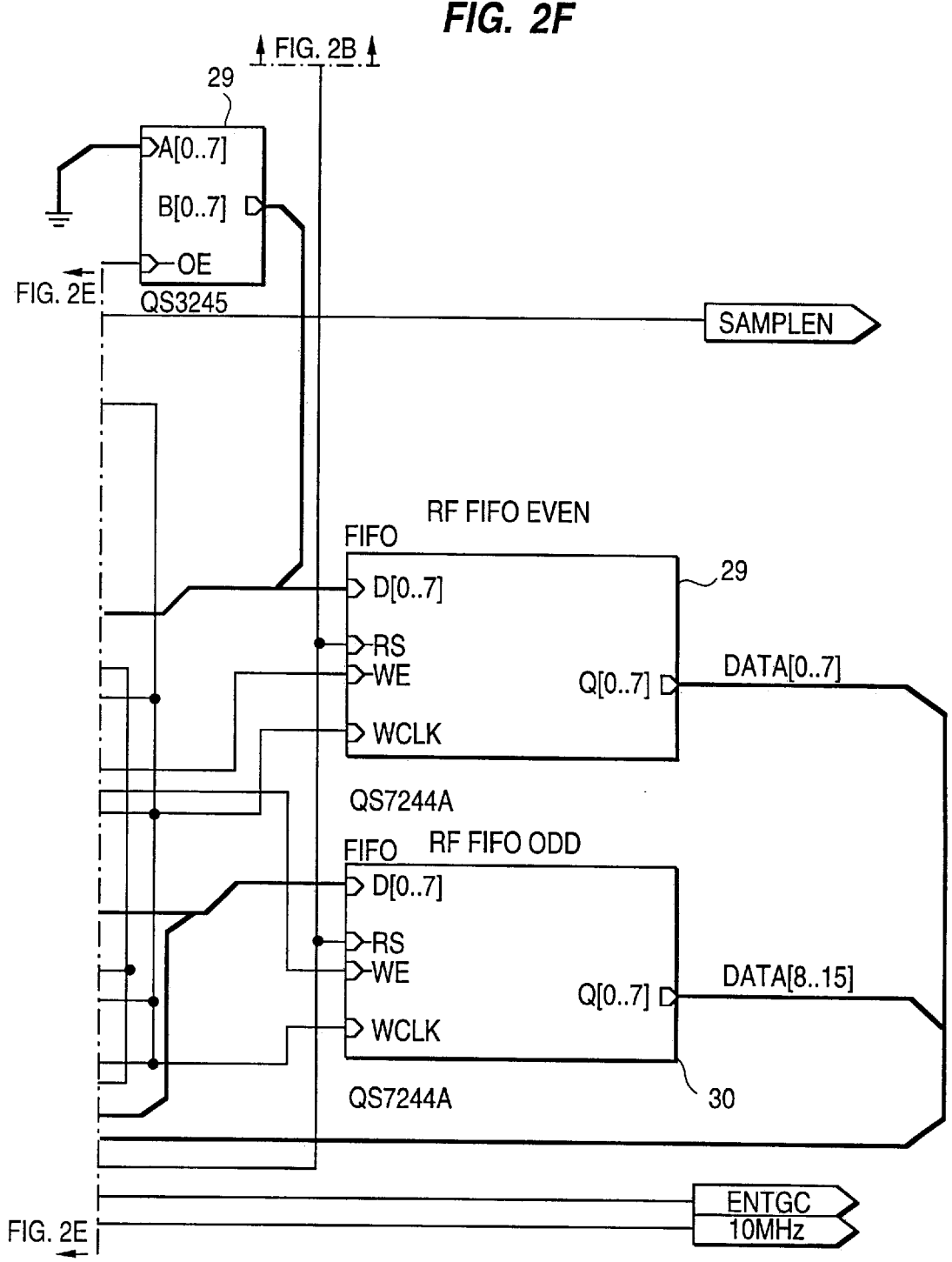
Figure 3A:
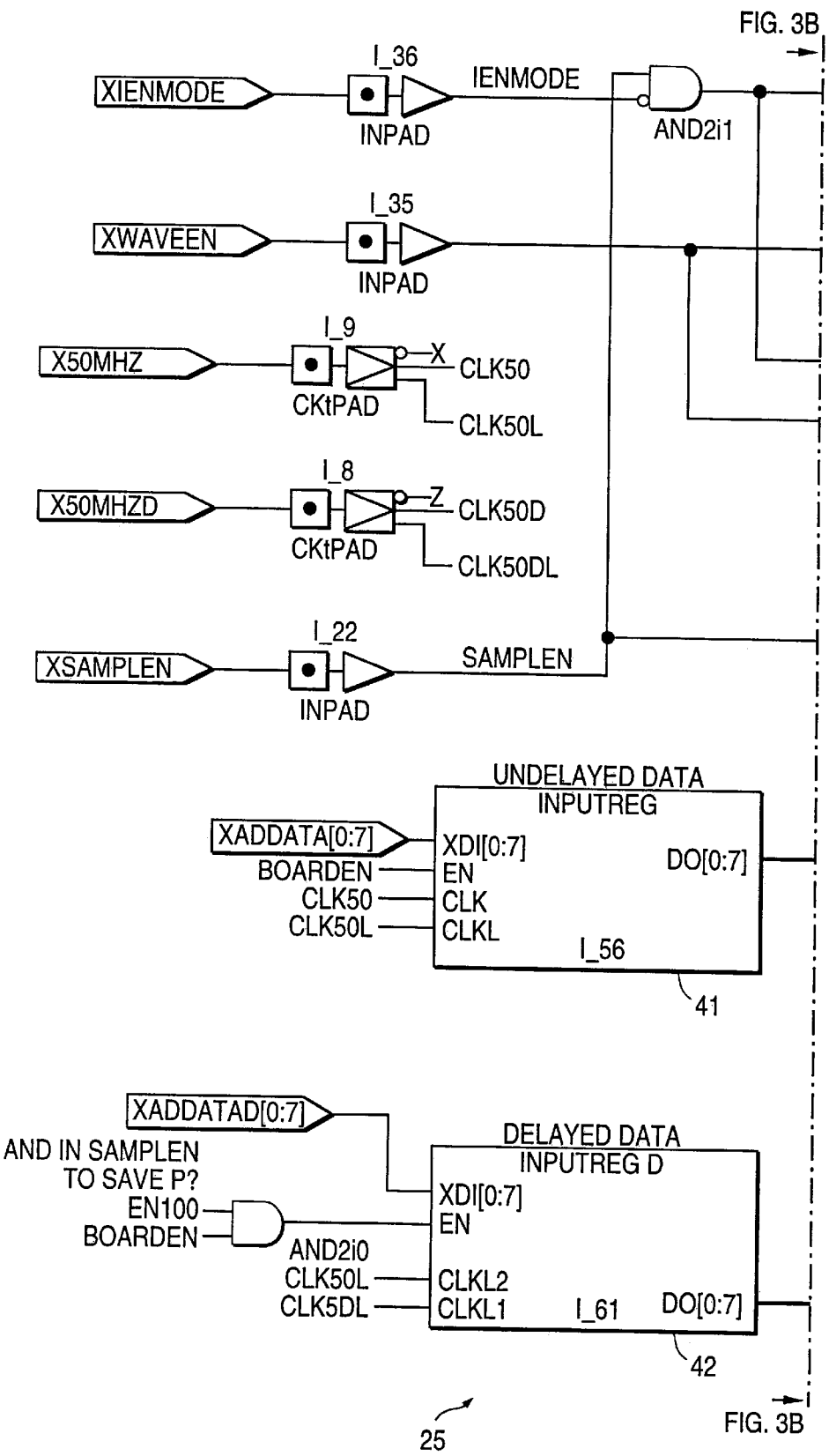
FIG. 3 (comprising FIGS. 3A, 3B, 3C, 3D, 3E, and 3F) is a block diagram of a wave field programmable gate array (FPGA) shown in FIG. 2.
Figure 3B:
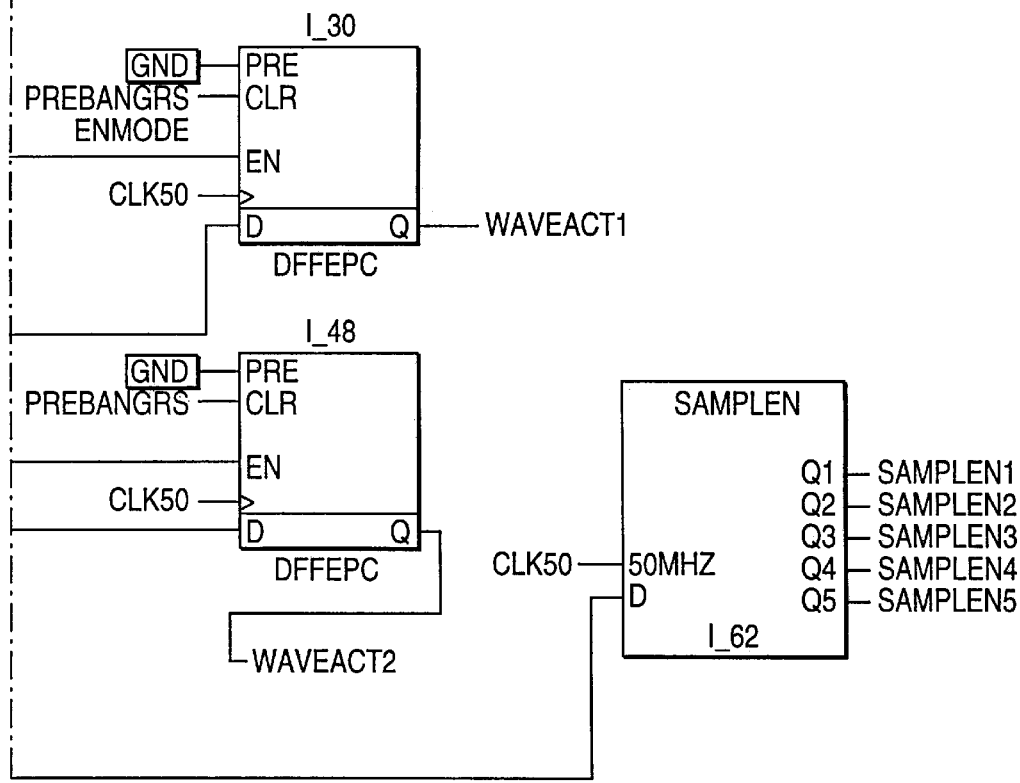
Figure 3B:
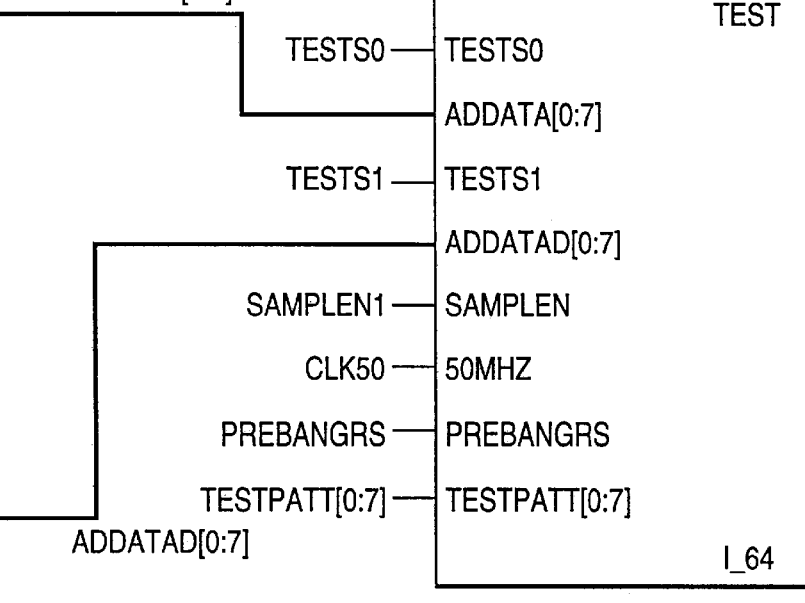
Figure 3E:
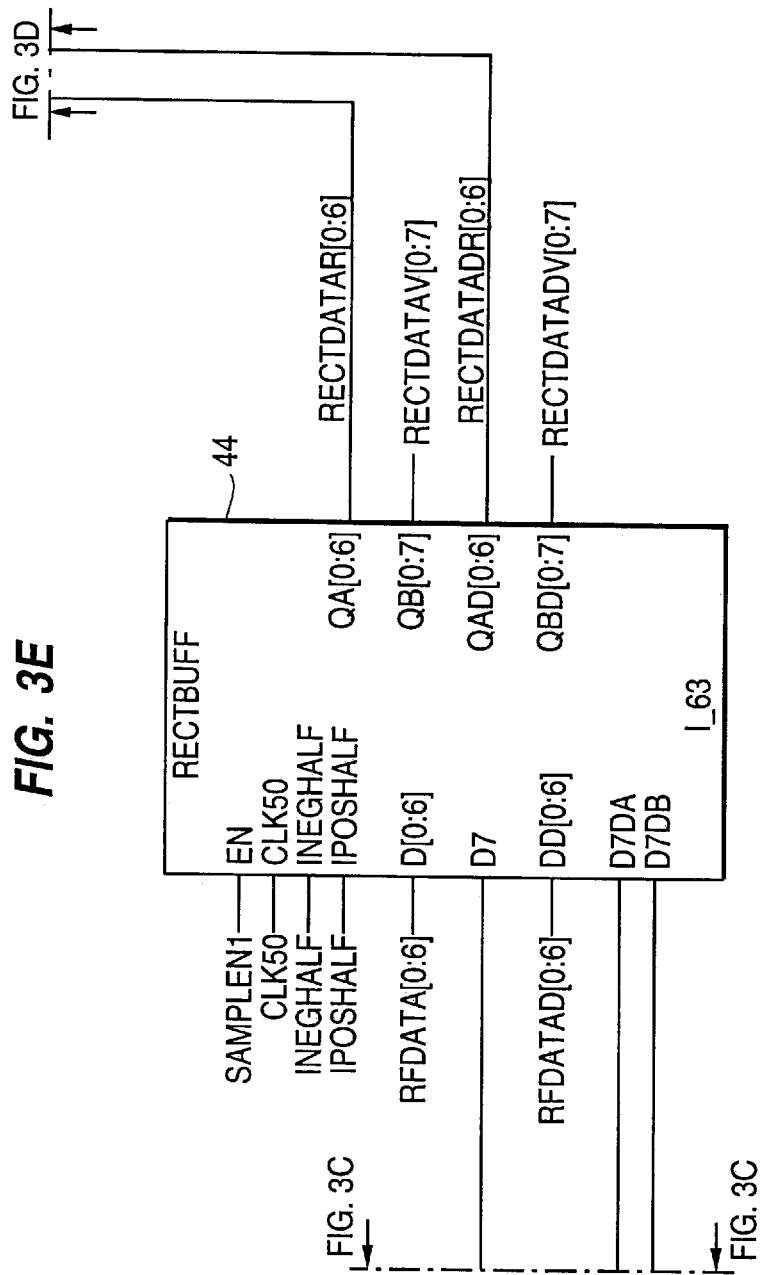
Figure 3F:
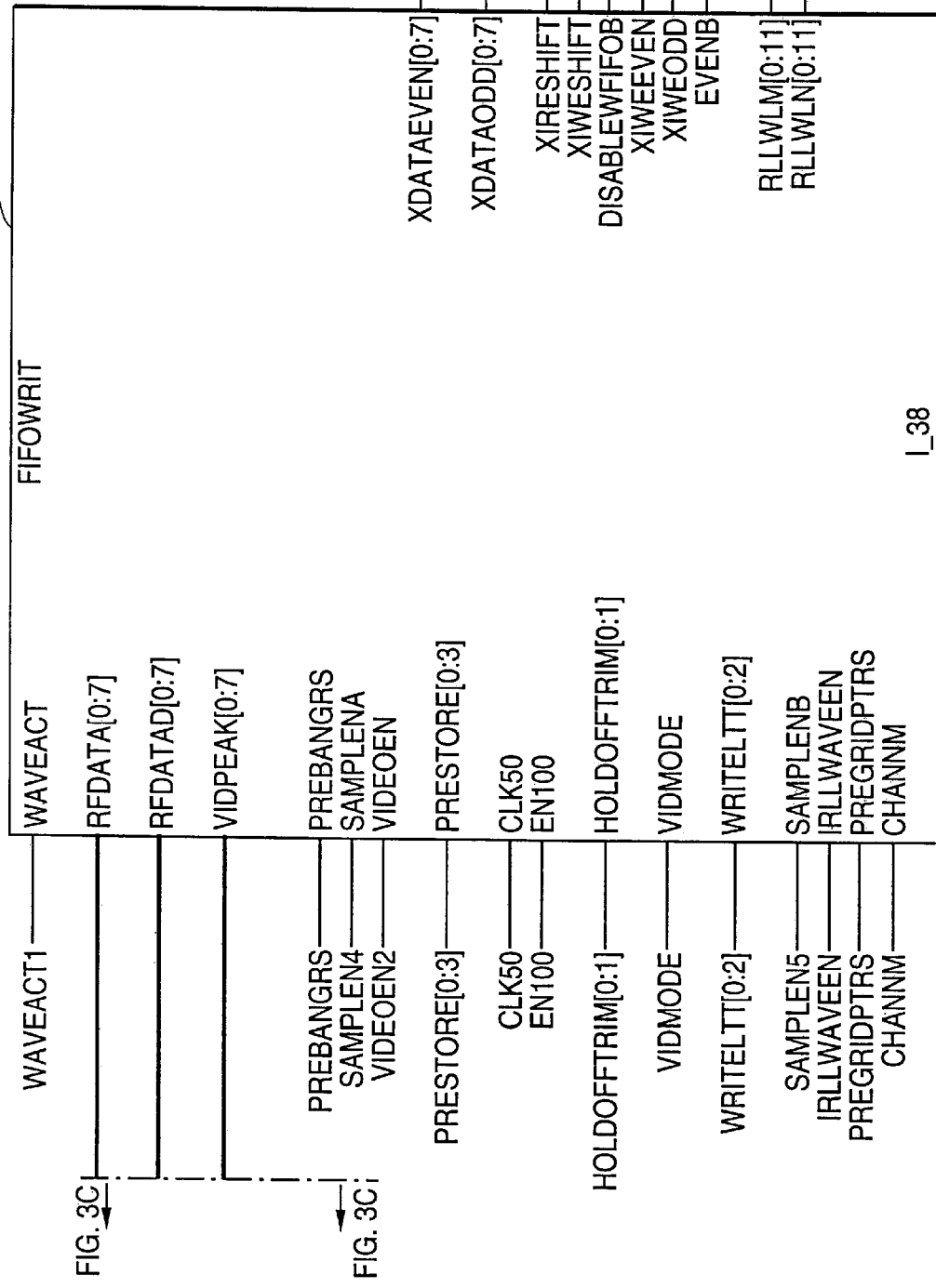

A more detailed diagram of the A-to-D converter 18 is shown in FIG. 2. With reference to FIG. 2, the RF input signal RF IN from the amplifier 16 is passed through an op-amp 20 which level shifts and amplifies the RF input signal. The output of the op-amp 20 is supplied to both analog inputs of an A/D converter 21. The A/D converter 21 is a dual 8-bit monolithic 50 MS/s A/D converter. When only an A section output is used, the A/D converter 21 has a sampling rate of 50 MS/s or less. To achieve a sampling rate of 100 MS/s, outputs on both the A section as well as a B section are used. Both the A and B sections of the A/D converter 21 receive a 50 MHz sample clock, with the B section sample clock being delayed by 10 ns by the use of analog delay circuits 22 and 23. As a result, the B section of the A/D converter 21 samples the RF input signal RF IN at a time which is midway between the sampling times of the A section of the A/D converter 21. By combining the two 8-bit data streams output from the A and B sections, a data stream at 100 MS/s can be formed. In the A/D converter 21, the two sections A and B have matched transfer characteristics and use the same 2 volt reference.

The two 8-bit data streams DA(0:7) and DB(0:7) output from the A/D converter 21 are supplied to a wave field programmable gate array (FPGA) 25. At the wave FPGA 25, video filtering and threshold-based run-length encoding (TRLE) are performed on the data DA and DB. A pair of first-in-first-out (FIFO) memories 26 and 27 prestore some of the data for the threshold-based run-length encoding and a circuit 28 injects "00h" control codes into the data stream for the threshold-based run-length encoding. A second pair of FIFO's 29 and 30 are used in high speed storage of the waveform data and are read out by the ISA bus interface circuit 13 after the waveform storage is complete.

A comparator FPGA 32 receives both the undelayed DA and the delayed DB data streams from the A/D converter 21 in parallel with the wave FPGA 25. The comparator FPGA 32 does not output data streams but rather determines peak values in the data streams DA and DB received from the A/D converter 21. This peak data may be read out by the CPU 9 through a data port DATA(0:7). The comparator FPGA 32 also supplies control signals to a timer FPGA 33 in order to control the storing of time-of-flights (TOF) associated with the peak values.

In addition to storing the time-of-flights (TOF), the timer FPGA 33 has several other purposes. The 50 MHz system clock runs continuously and the rate at which the ultrasonic signal is sampled and processed may be varied by selectively pulsing a sample enable signal (SAMPLEN) so as to enable storage and processing during only one of N clock periods. The timer FPGA 33 is also used in conjunction with two 8K by 8-bit static random access memories (SRAM) 35 and 36 to define a waveform acquisition interval and a hardware gate search interval, both of which will be described in more detail below. The timer FPGA 33 includes a hardware gate time-of-flight counter, time-of-flight registers, and multi-channel control circuitry, which will also be described in more detail below.

The video rectifier and filter portion of the wave FPGA circuit 25 can compress the data received from the ultrasonic transducer by a fixed ratio of up to 16:1. The FPGA circuit 25 stores the value of the sample having the highest amplitude in an 8-bit register with the lower 7 bits representing the amplitude and the most-significant representing the sign of the data. The wave FPGA 25 can recover faster than analog versions since the next "bin" is not obscured by the usual analog peak-detector discharge tail.

With reference to FIG. 3 the wave FPGA 25 comprises a pair of registers 41 and 42 with the undelayed A-to-D data DA passing through register 41 and the delayed data DB passing through register 42. From the two registers 41 and 42, the data is input into a TEST circuit 43 and then to a rectifier and buffer circuit RECTBUFF 44 where the data is rectified.

The A/D converter 21 provides the data DA and DB in an offset binary format so that 00h and 01h represent the most negative inputs, 80h represents the middle of the data range, and FEh and FFh represent the most positive input.

Figure 4:
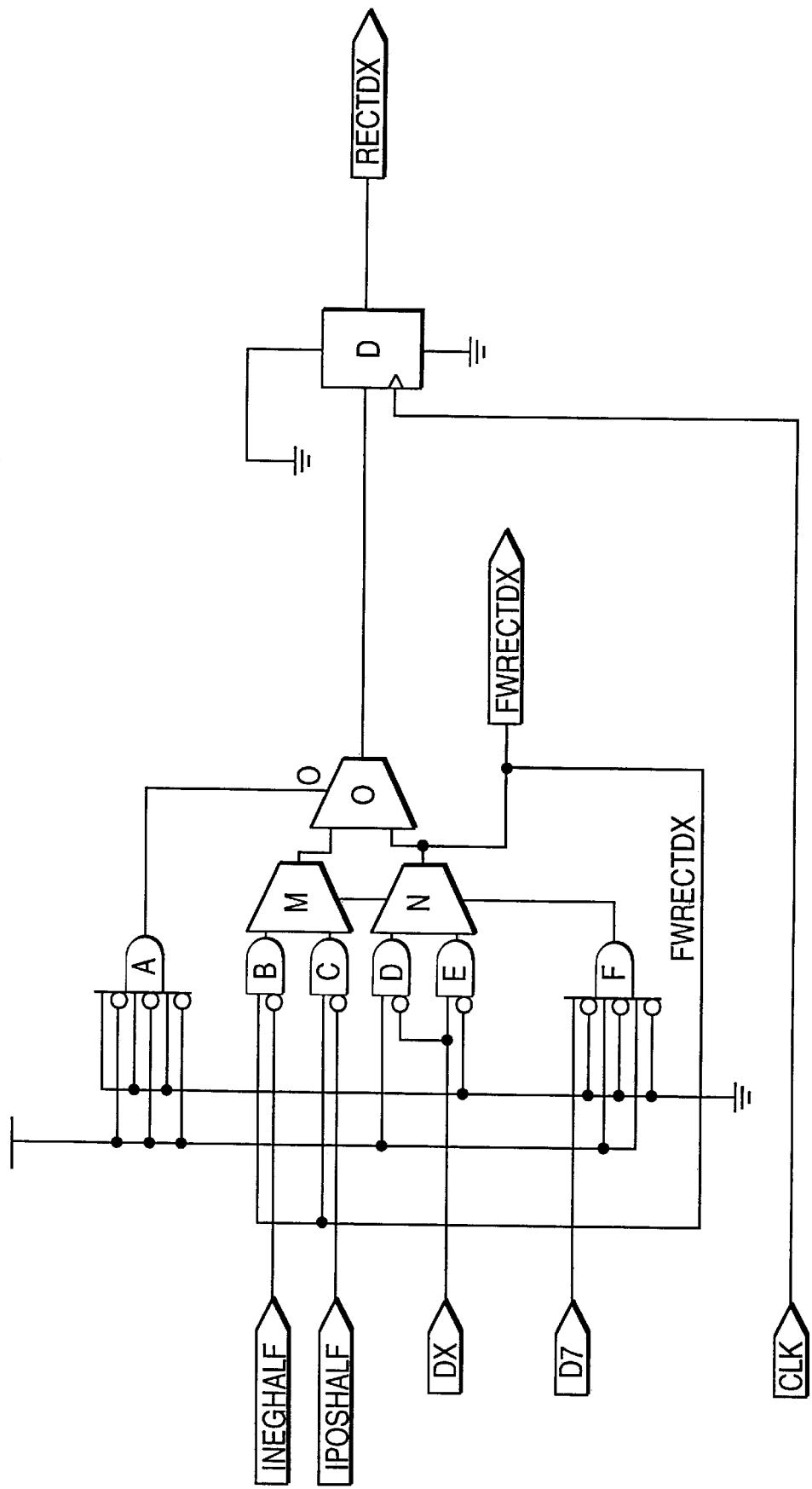
FIG. 4 is a schematic of a rectifying circuit.
Figure 5A:
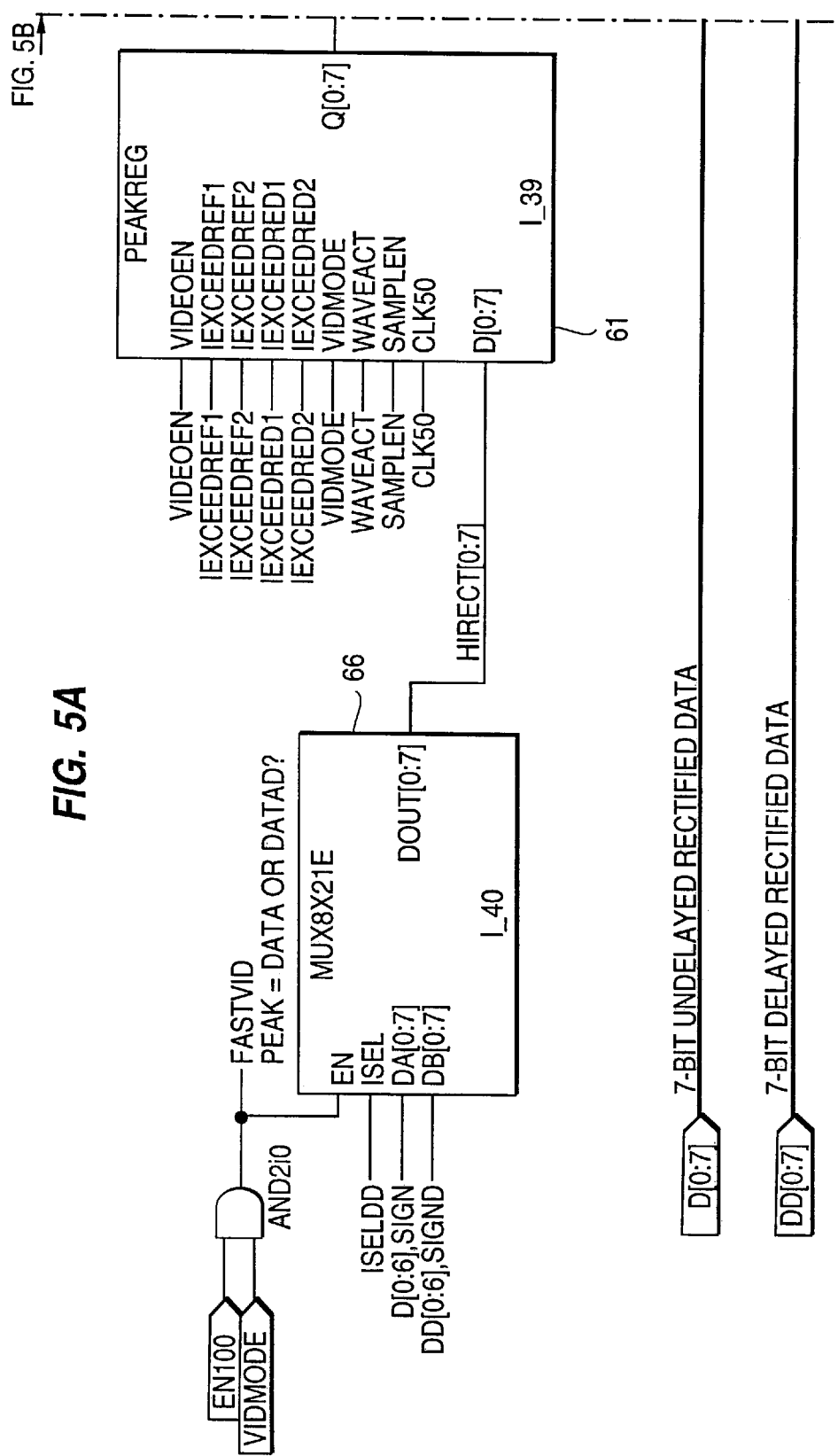
FIG. 5 (comprising FIGS. 5A, 5B, 5C and 5D) is a block diagram of a VIDEO circuit shown in FIG. 3.
Figure 5B:
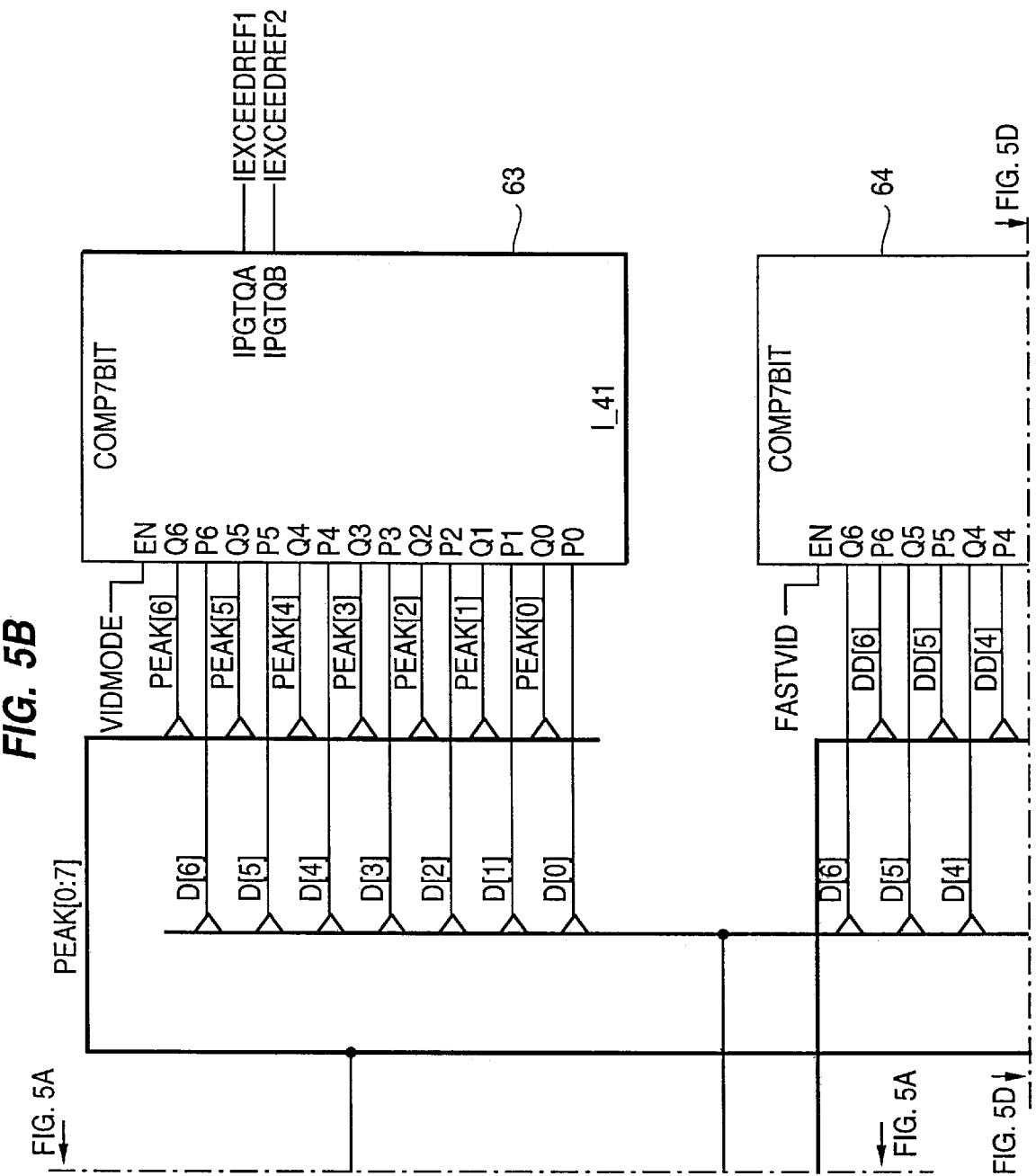
Figure 5C:
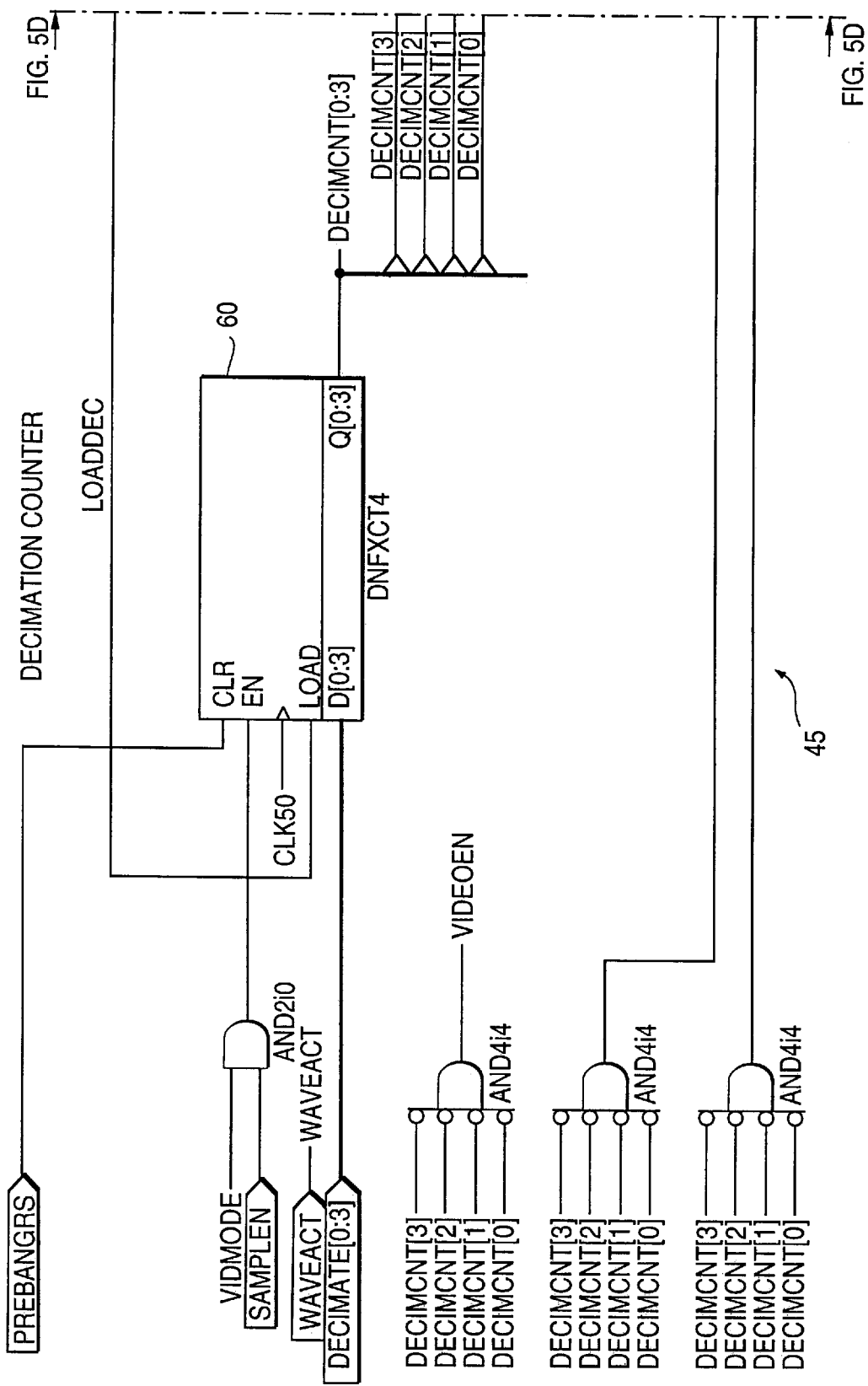
Figure 5D:
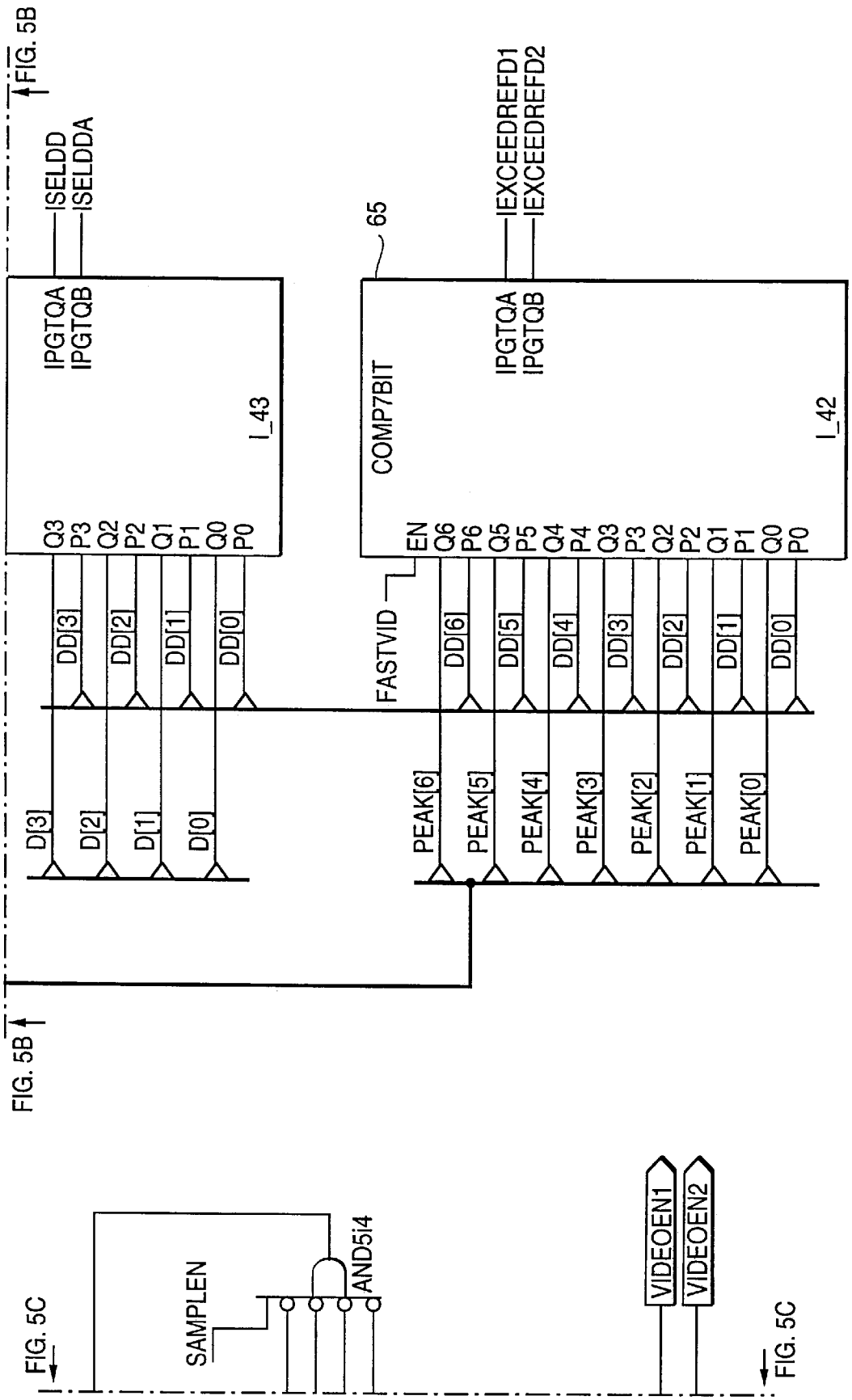
Figure 6A:
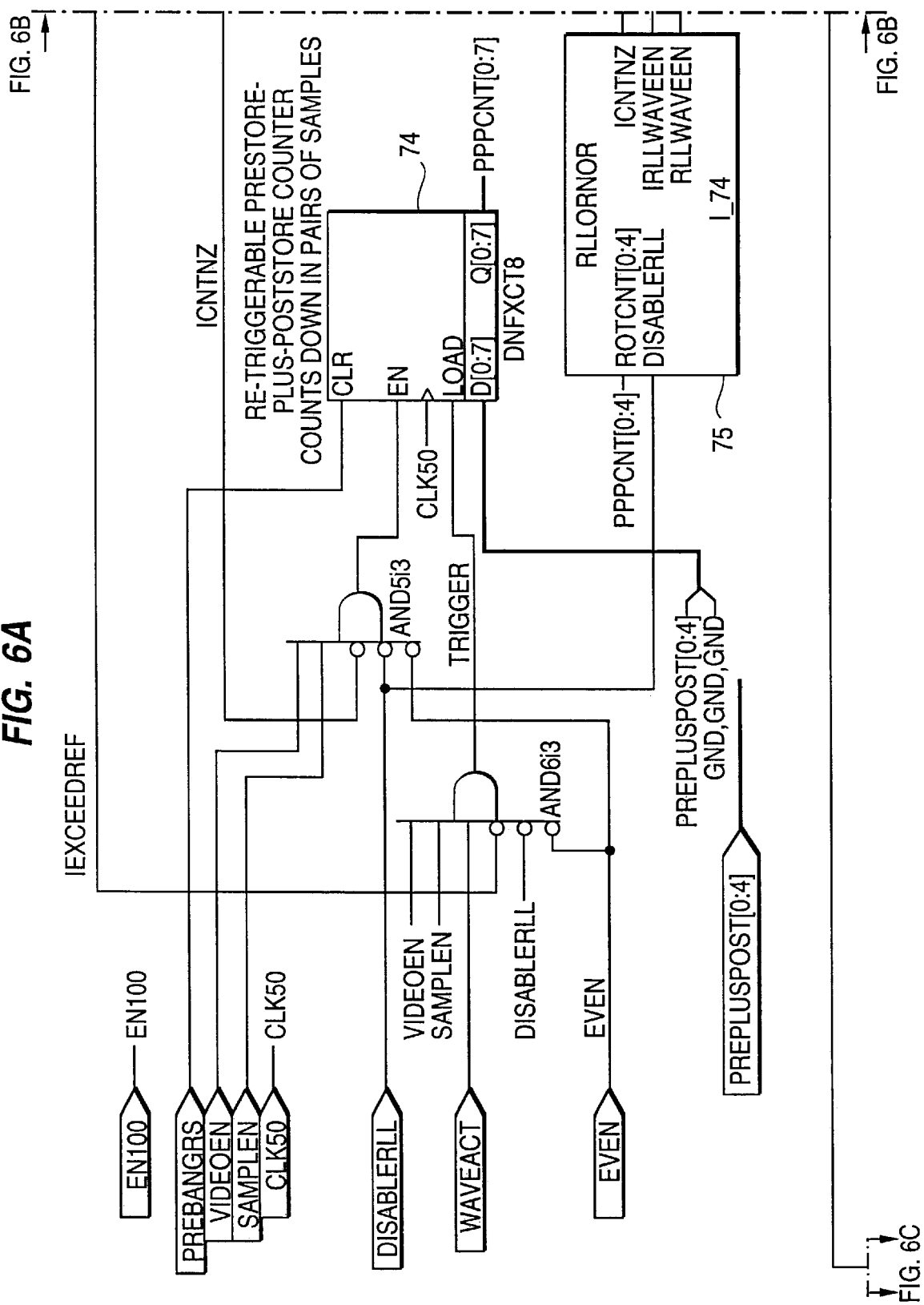
FIG. 6 (comprising FIGS. 6A, 6B, 6C, 6D, 6E and 6F) is a block diagram of an RLL circuit shown in FIG. 3.
Figure 6B:
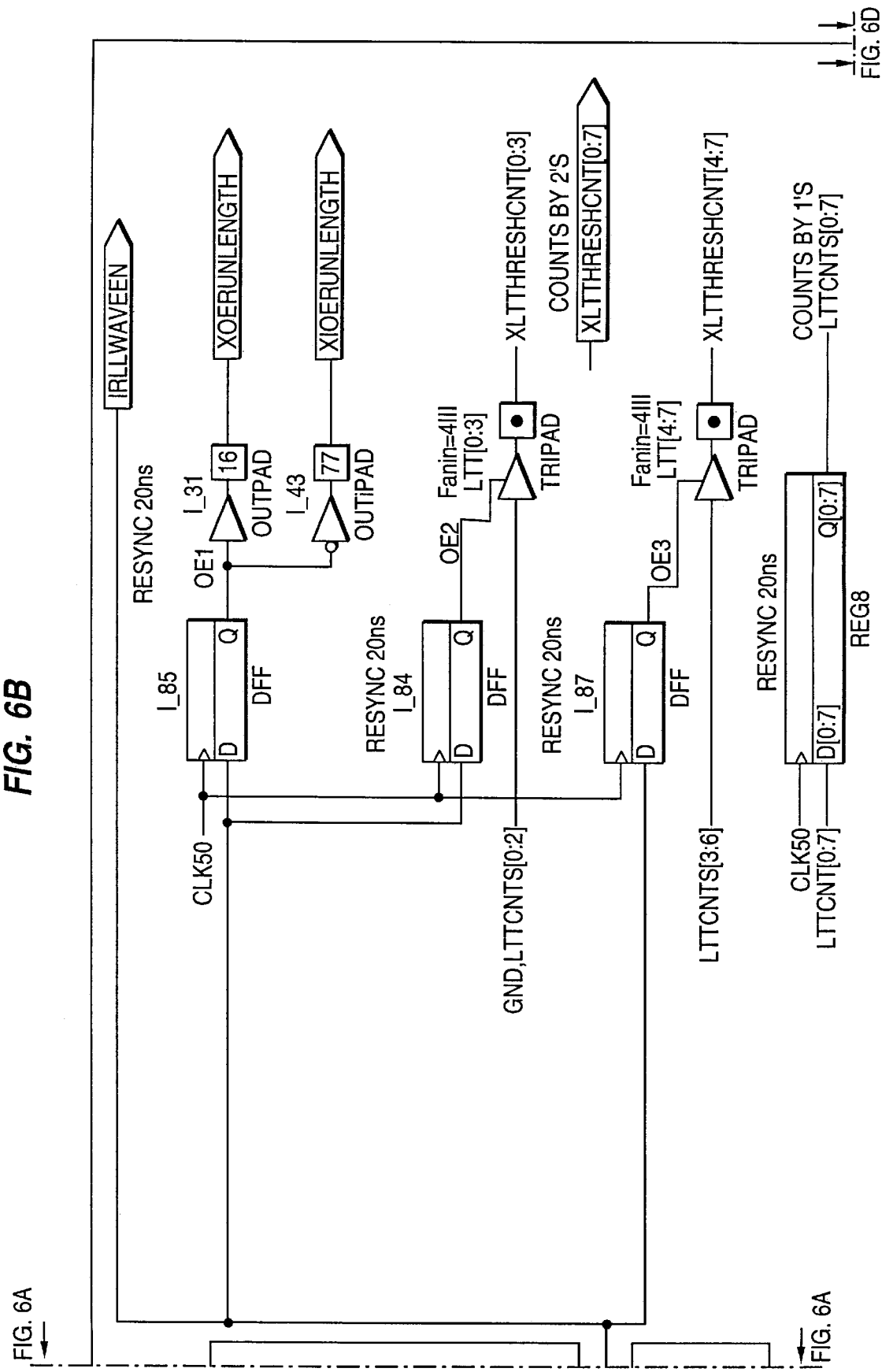
Figure 6C:
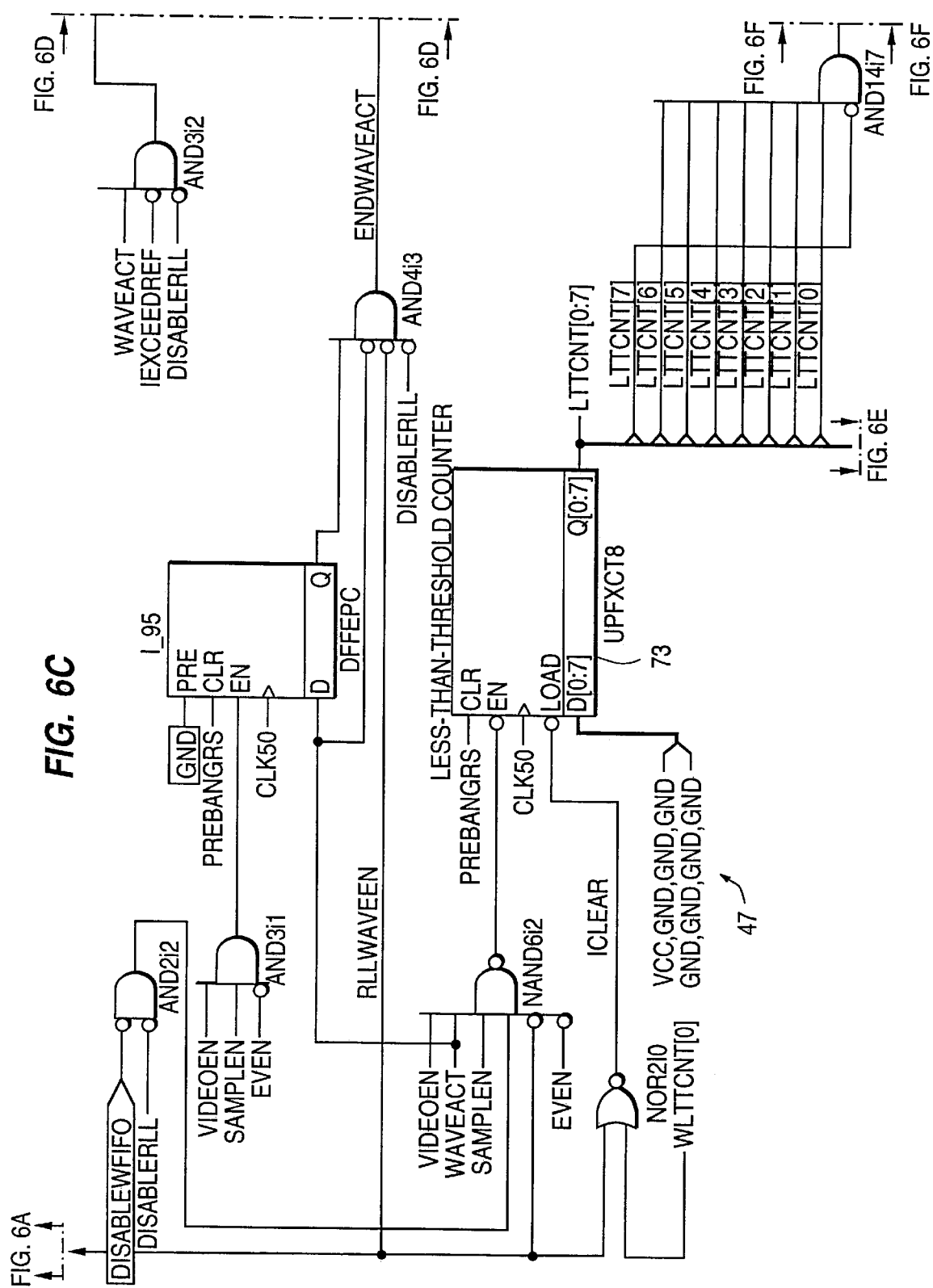
Figure 6D:
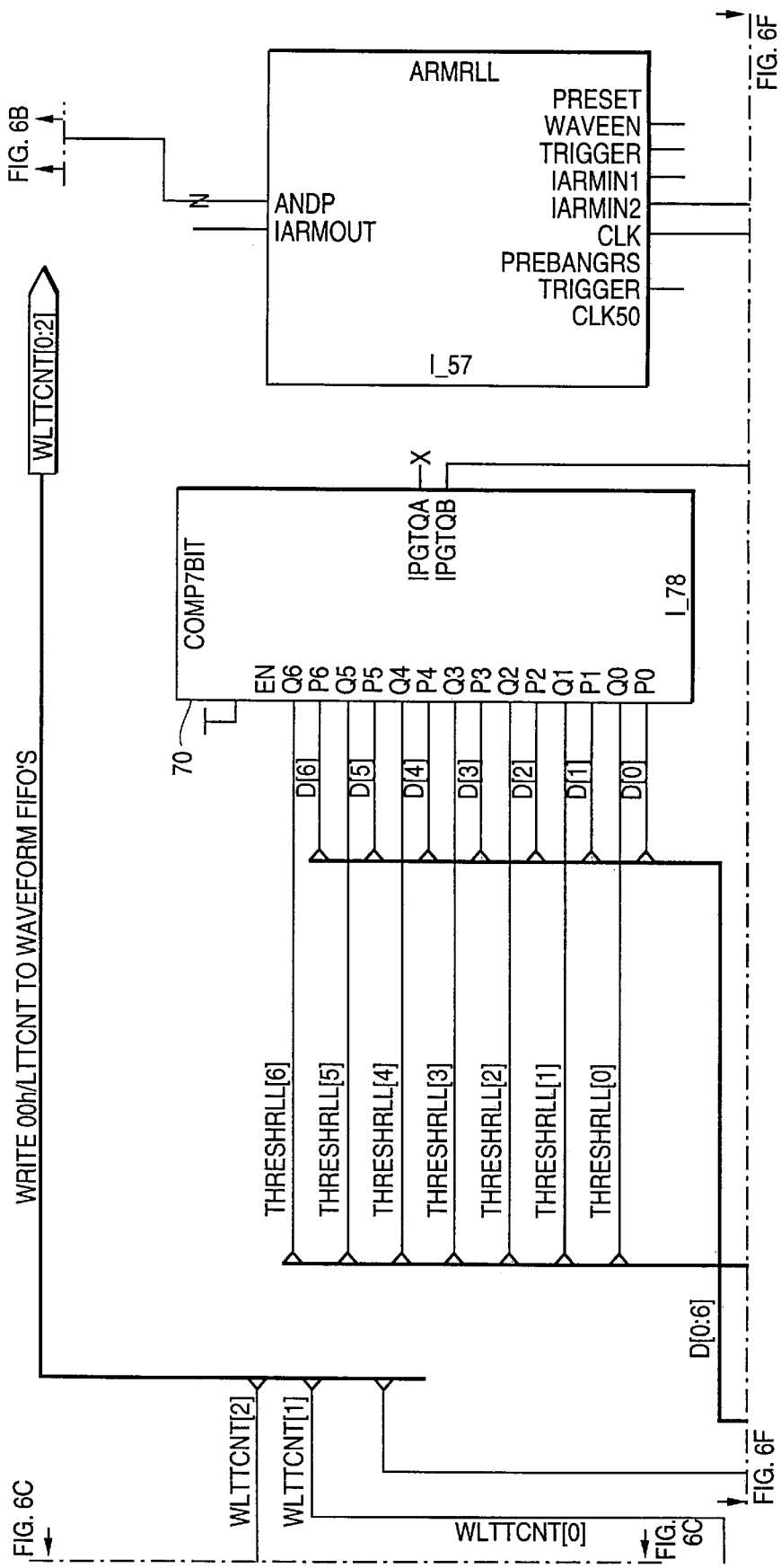
Figure 6E:
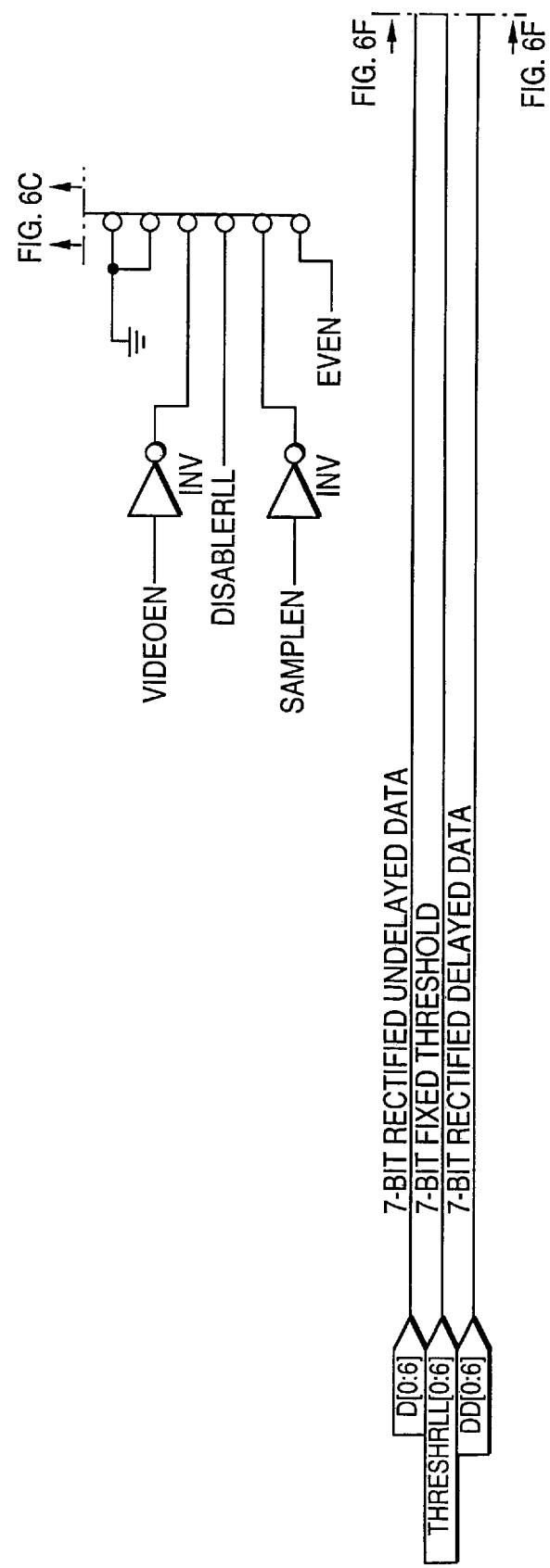
Figure 6F:
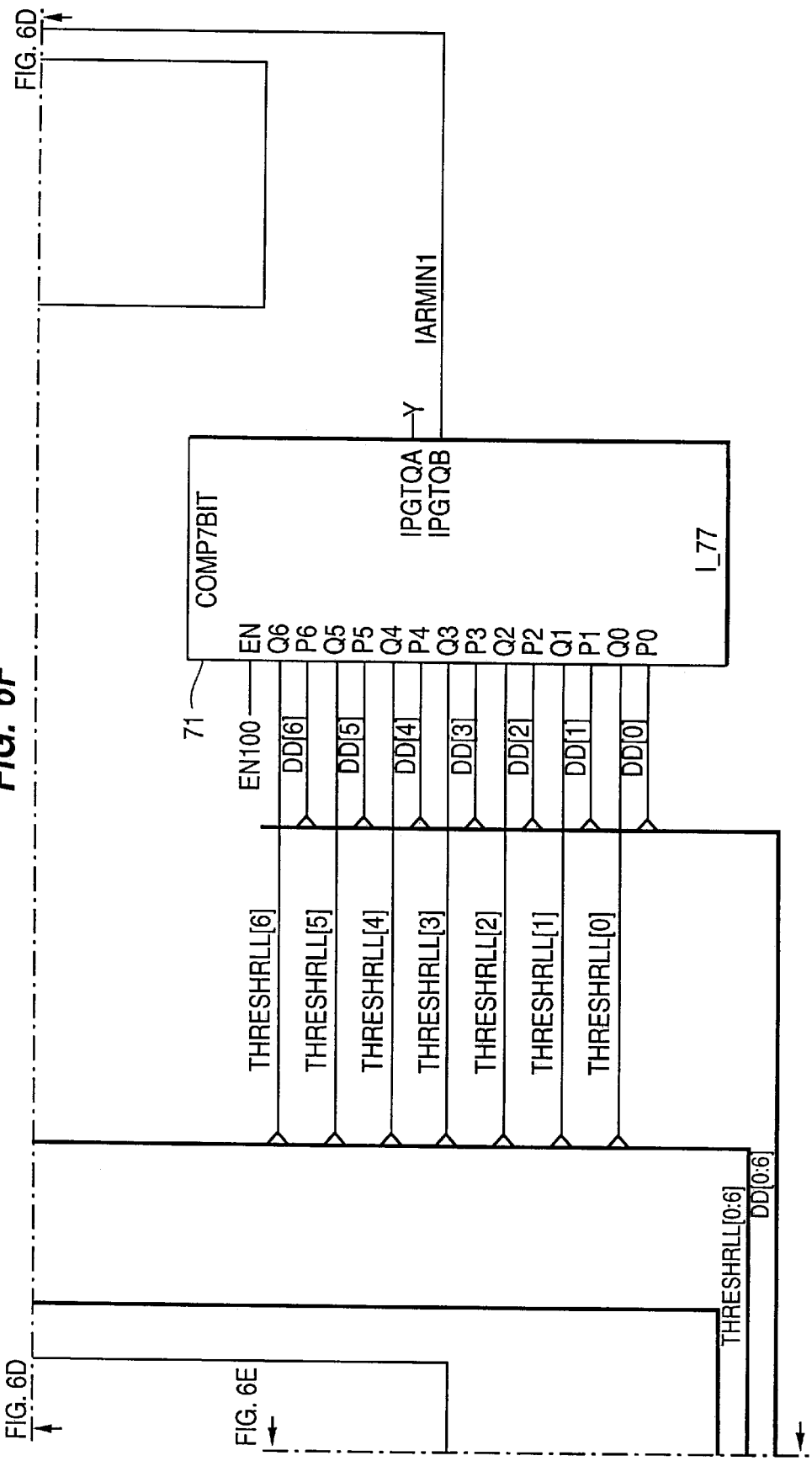
Figure 7A:
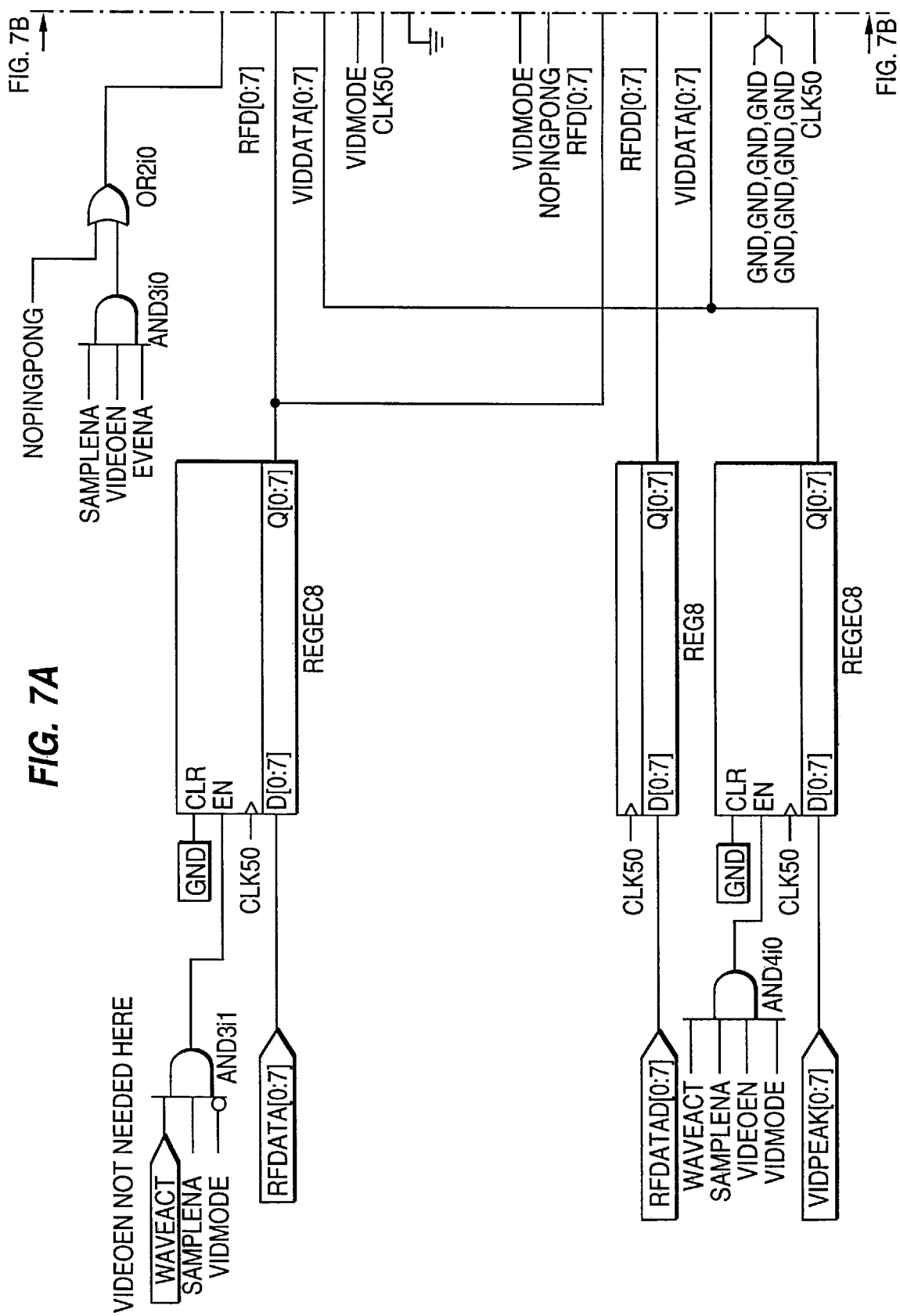
FIG. 7 (comprising FIGS. 7A, 7B, 7C, 7D, 7E and 7F) is a block diagram of a FIFOWRIT circuit shown in FIG. 3.
Figure 7B:
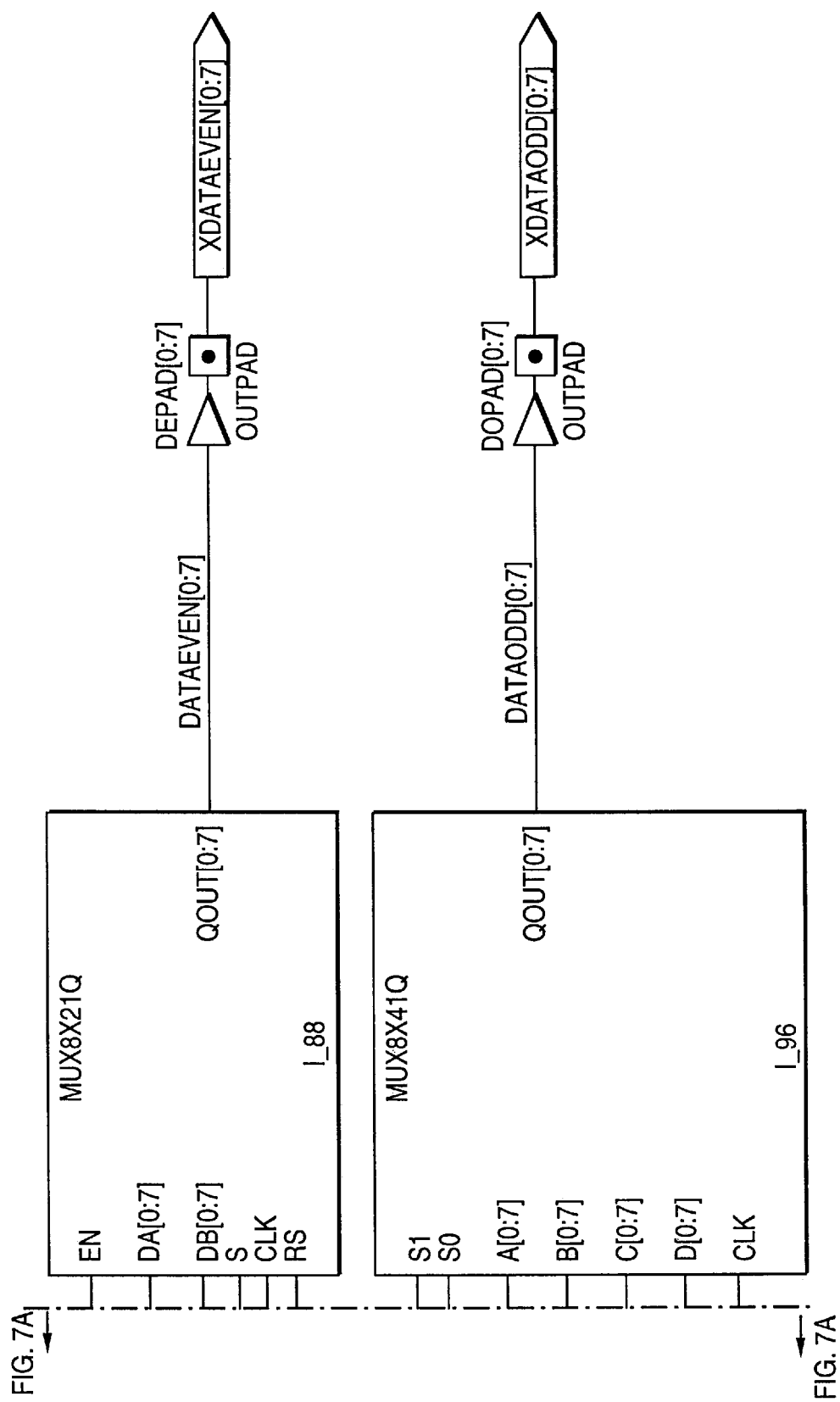
Figure 7C:
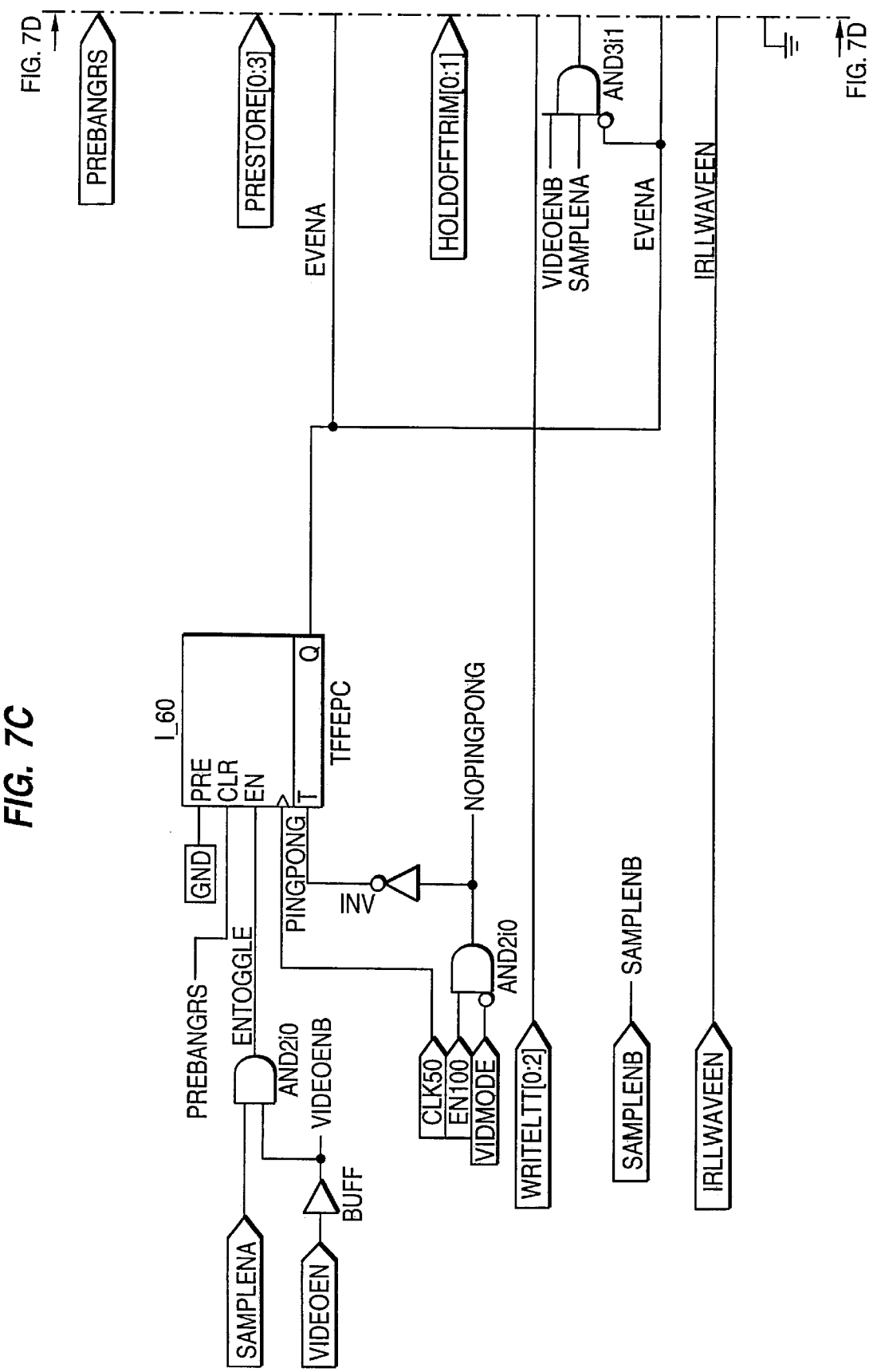
Figure 7F:
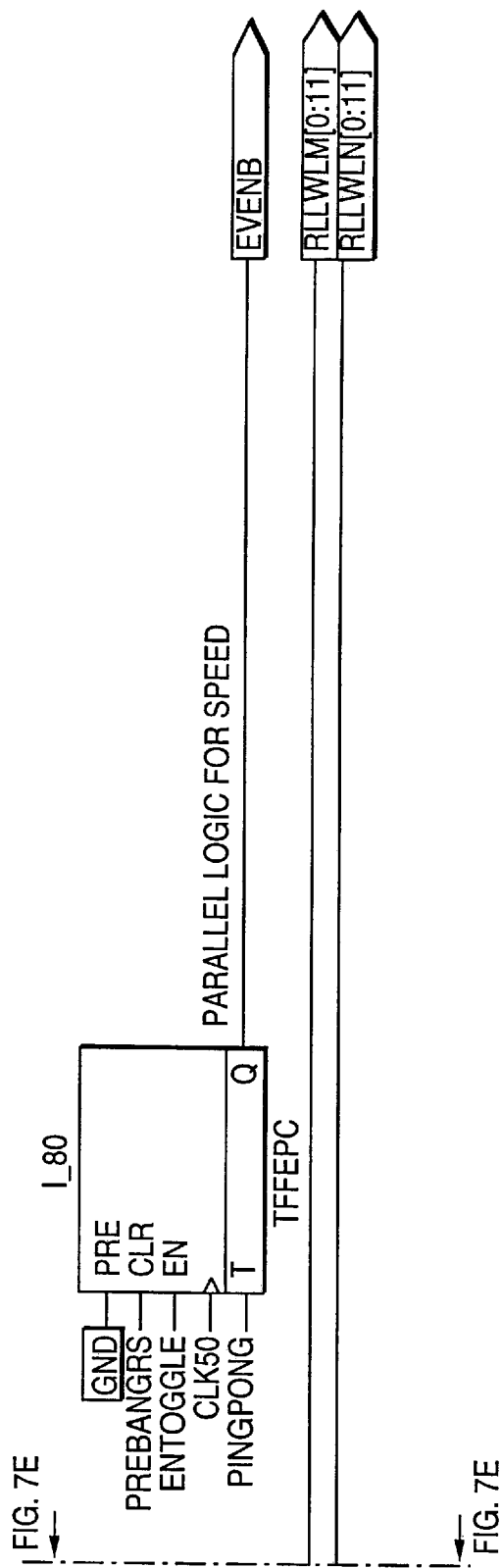

FIG. 4 illustrates an example of a rectifying circuit for one bit of the data signals DA and DB. With reference to FIG. 4, a first stage of the rectifier is a 1's complement full-wave rectifier and comprises logic gates D, E, F, and N. If the input sign determined by data bit D7 is low, indicating that the sample is a negative number, a multiplexer N selects a complemented version of the input data. On the other hand, if the input sign determined by data bit D7 is high, indicating that the sample is a positive number, the multiplexer N selects the unmodified input data.

The second stage of the rectifier allows for positive or negative half-wave rectification instead of just full-wave rectification. The second stage comprises a multiplexer 0 for always selecting output of a multiplexer M. The output from the multiplexer 0 is fed back into non-inverting inputs of AND gates B and C. The AND gates B and C also respectively receive control signals INEGHALF and IPOSHALF. When both of the control signals INEGHALF and IPOSHALF are equal to zero, a full-wave rectified data passes unchanged through the second stage of the rectifier. If on the other hand, the control signal INEGHALF is equal to 1 and the control signal IPOSHALF is equal to 0, then the data bit is replaced by a zero when the input sample is negative. Conversely, if the control signal IPOSHALF is equal to 1 and the control signal INEGHALF is equal to 0, then the data bit is replaced by 0 when the input sample is positive. In this manner, a positive or negative half-wave rectification of the input signal may be accomplished. The sign bit for the data is preserved by passing through the most significant bit, which is D7, of the original input sample. The data streams are re-synchronized with the clock signal CLK through the D flip-flop register.

After being rectified within the rectifier and buffer circuit 44, the two 8-bit data streams flow into a VIDEO circuit 45. The VIDEO circuit 45, as shown in more detail in FIG. 5, comprises a counter 60 for counting a programmable number of sample periods to define a video enable period (VIDEOEN). The video enable period is the interval over which the rectified signal is searched for a maximum amplitude.

In operation, the first input data sample in a video enable period, or sample bin, is always stored in an 8-bit register PEAKREG 61. Since the VIDEO circuit 45 receives two data samples per clock period when the ultrasonic testing system 10 operates at a sampling rate of 100 MS/s, magnitudes of the delayed and undelayed data samples are compared by a middle comparator 64 which signals a multiplexer 66 which of the two samples to select for storage.

During the second and subsequent sample times of the video enable period, magnitudes of the second or subsequent undelayed and delayed samples are compared to that of the present peak value by comparators 63 and 65, respectively. If either the delayed data or the undelayed data is larger than that stored in the peak register 61, comparator 63 or 65 will respectively signal the peak register PEAKREG 61 to store that sample. When both the delayed and undelayed data are larger than the data stored in the peak register 61, the comparator 64 will signal the multiplexer 66 to supply the peak register PEAKREG 61 with the larger of the two samples. This process of comparing the data samples stored in the peak register 61 with the incoming data samples continues until the first sample time in the next video enable period at which time the value from the peak register 61 is transferred out of the VIDEO circuit 45 to a FIFOWRIT circuit 46 so that this value can be recorded as part of the processed waveform.

As a result, the wave FPGA circuit 25 can output a data stream having a data rate which is reduced from the input data rate by a factor of N, where N is equal to the ratio of the video enable period over the sample period. The measured time resolution is therefore coarser by a factor of N since each video enable peak is assigned arbitrarily to a sample period bin with the peak amplitudes being preserved. The wave FPGA circuit 25 performs the logic functions described above at the requisite speed by pipelining the data, by using short critical paths, by employing parallel logic and by selective buffering.

To achieve a higher resolution, the exact time-of-flight may be preserved by storing one byte or a fraction of one byte of timing information per waveform sample. The timing information is actually a time-of-flight off-set which is generated by an extra counter which counts sample enable SAMPLEN periods during each video enable VIDEOEN period. The time-of-flight TOF offset is inserted into the data stream together with the peak data.

As stated above, the wave FPGA circuit 25 is also used for threshold-based run-length encoding and can compress the data received from the ultrasonic transducer 7 by a variable ratio of up to 128:1, with ratios of 5:1 to 20:1 being common. The wave FPGA 25 performs threshold-based run-length encoding by storing only that data having an amplitude which exceeds a user-selectable threshold along with a user selectable number of samples before and after the below-to-above and above-to-below threshold crossings, respectively. The length of the intervals of less-than-threshold (LTT) data are signaled by the injection of control codes 00h and LTT counts directly into the data stream.

With reference to FIG. 3, an RLL circuit 47 receives the rectified data from the rectifier and buffer circuit 44 and performs most of the control logic specific to threshold-based run-length encoding. The rectified data stream from the rectifier and buffer circuit 44 contains no 00h values and any naturally occurring 00h values in the data stream are removed by the TEST circuit 43 and replaced with 01h. The value of 00h is reserved for use as a control code to signal that a less-than-threshold count will follow.

FIG. 6 illustrates the RLL circuit 47 in more detail. In this diagram, a signal WAVEACT reflects a waveform acquisition interval requested by the user. When this signal WAVEACT is equal to 1, the data samples for the waveform are recorded and/or compressed by the wave FPGA circuit 25. More specifically, during the interval when the signal WAVEACT is equal to 1, magnitudes of the rectified waveform samples received from the rectifier and buffer circuit 44 are compared to a user programmable threshold THRESH-RLL by a pair of comparators 70 and 71. If the amplitudes of the samples are less than the specified threshold THRESHRLL, then most of the samples are not stored in the waveform FIFO's 29 and 30. A less-than-threshold counter 73 counts the number of samples which are not stored by the FIFO's 29 and 30. When the waveform amplitude exceeds the threshold THRESHRLL, the control code 00h and a less than threshold count byte LTTCNT, indicating how many below threshold samples were not recorded, are injected into the data stream and waveform storage begins.

The minimum number of waveform samples to be stored in a group is set by a re-triggerable prestore-plus-poststore counter 74. During the less-than-threshold intervals, and after post-store is finished, the output of the counter 74 is 00h. As soon as waveform storage is resumed, the output of the counter 74 is loaded with a data value of PREPLUSPOST(0:4) and the pre-plus-post count PPPCNT (0:7) begins counting down towards 00h. If the counter 74 reaches 00h, an RLLORNOR circuit 75 causes the pre-plus-post count to wait for the next above threshold excursion. If, on the other hand, an above threshold excursion is detected before reaching 00h, the counter 74 is immediately reloaded with the count of PREPLUSPOST. As long as the output of the counter 74 is not equal to 00h, the value of the signal IRLLWAVEEN is equal to 0 and the waveform is allowed to be stored in the waveform FIFO's 29 and 30. Thus, in summary, the wave FPGA circuit 25 will store waveform samples in the FIFO's 29 and 30 in a number equal to, or greater than, the pre-plus-post count PPCPNT for each excursion above the user defined threshold THRESHRLL.

Figure 8A:
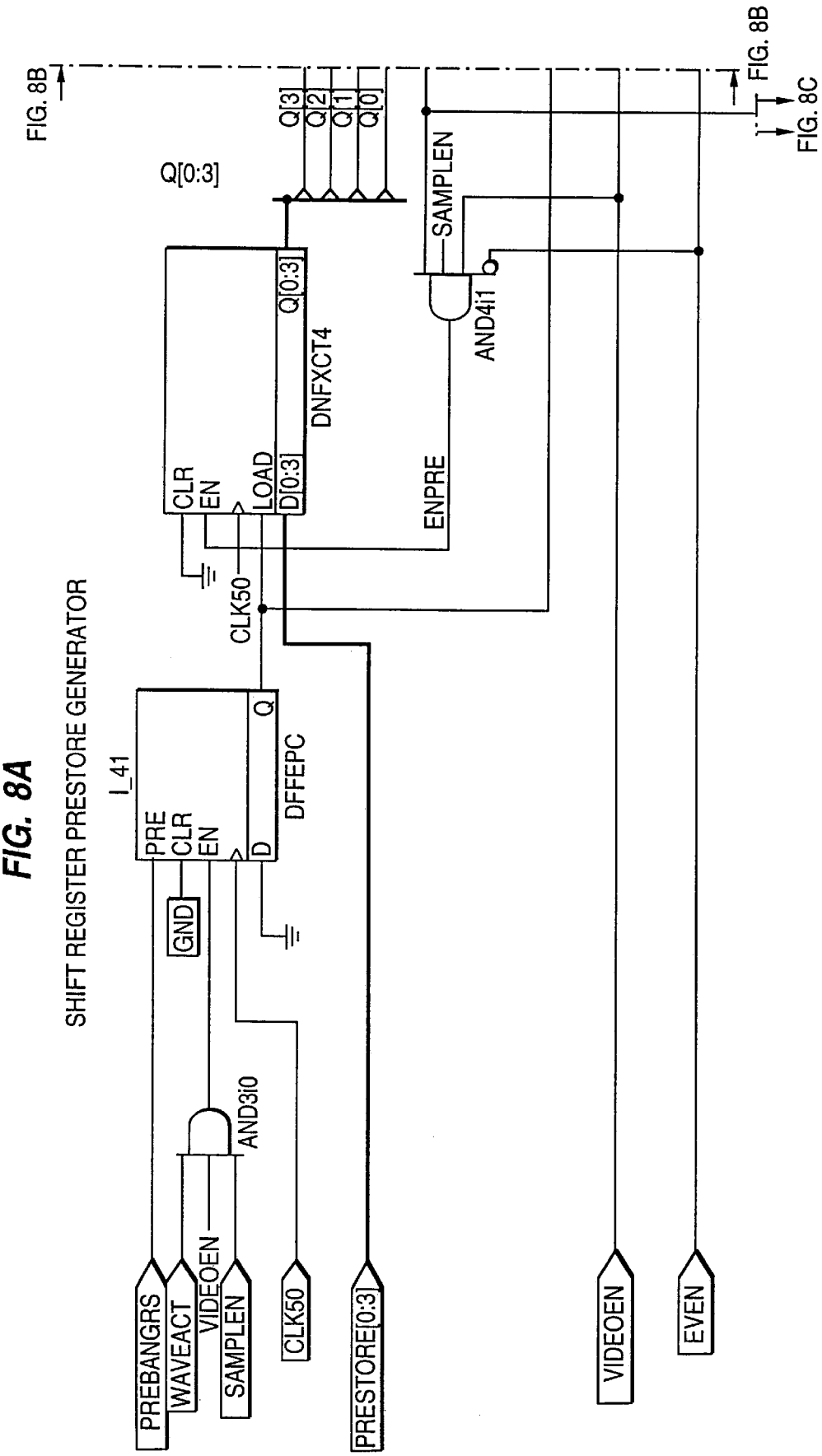
FIG. 8 (comprising FIGS. 8A, 8B, 8C and 8D) is a block diagram of a PRESTORE circuit shown in FIG. 7.
Figure 8B:
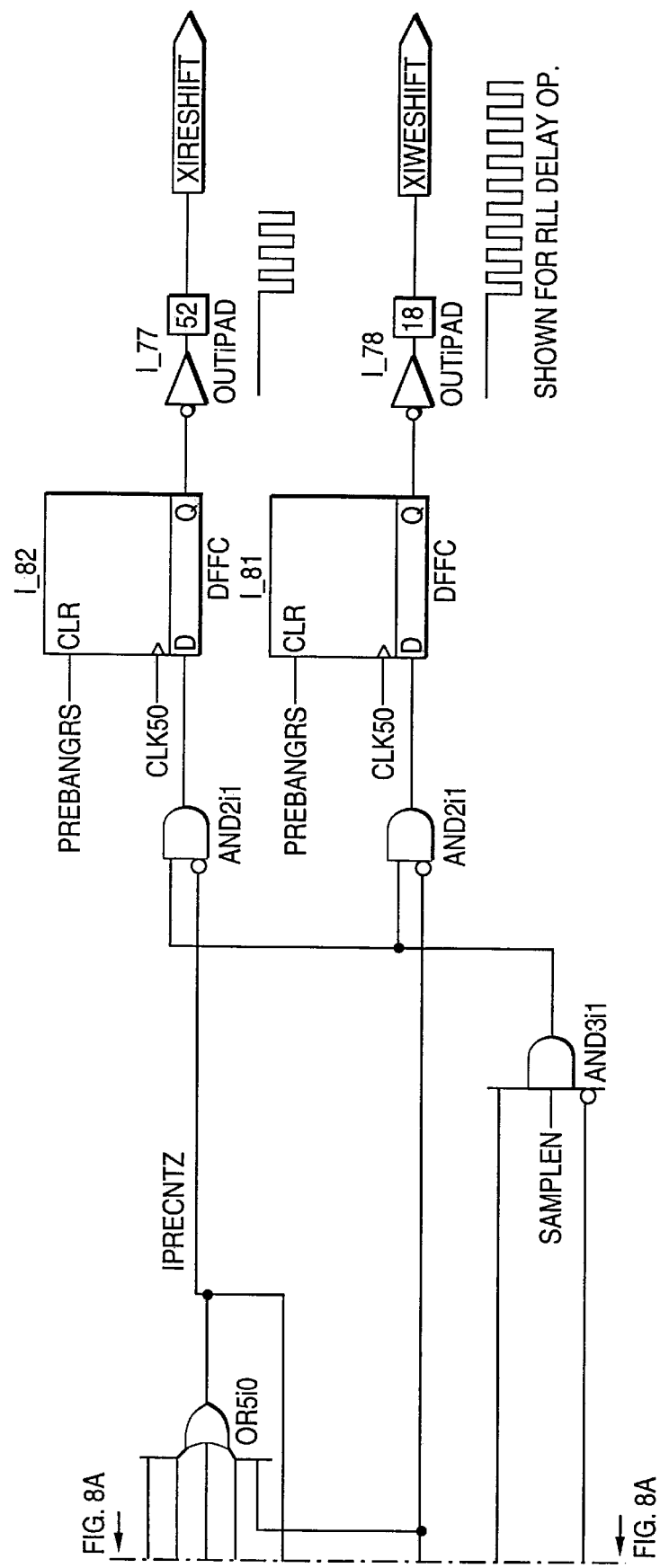
Figure 8C:
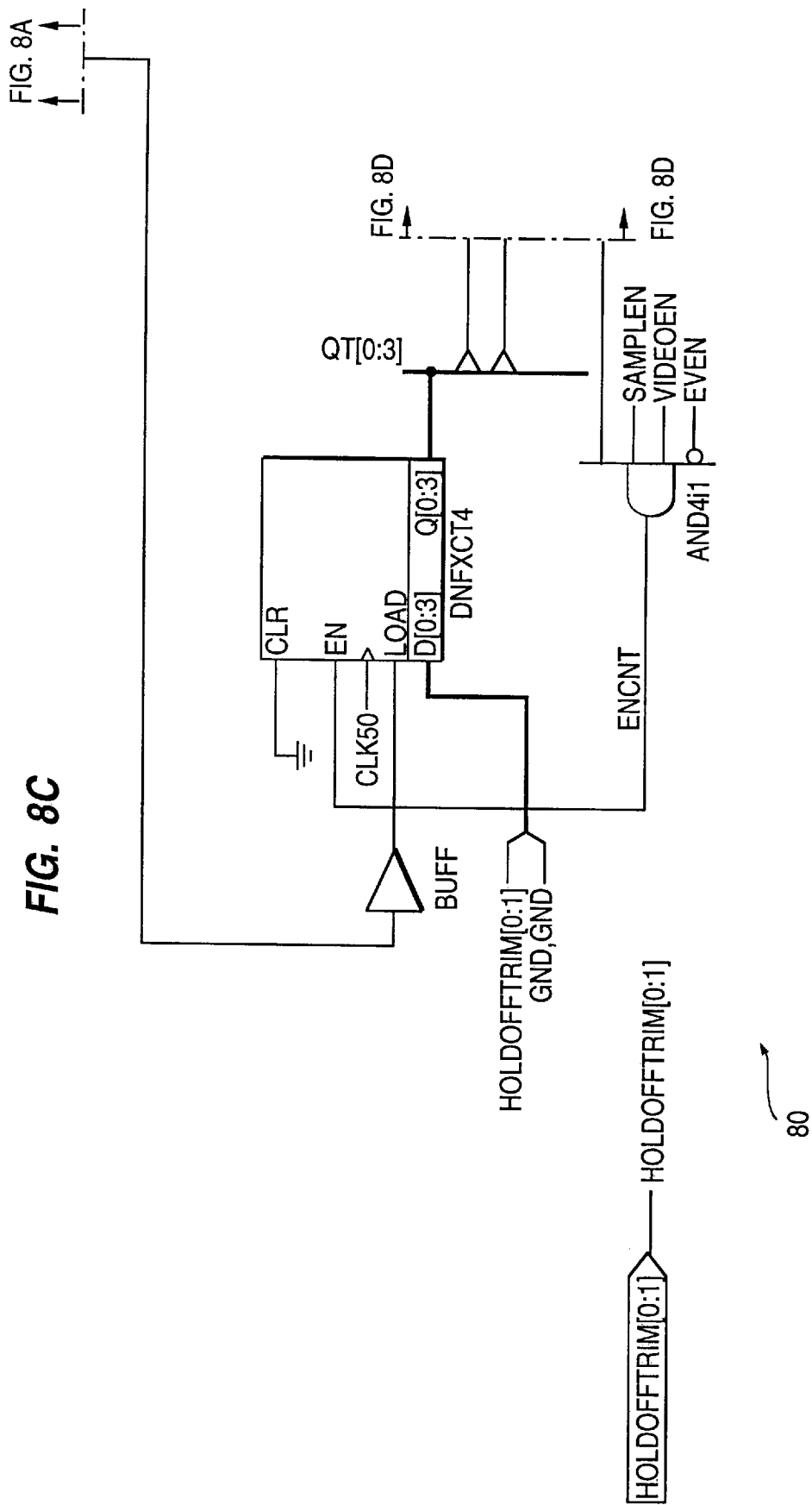
Figure 9A:
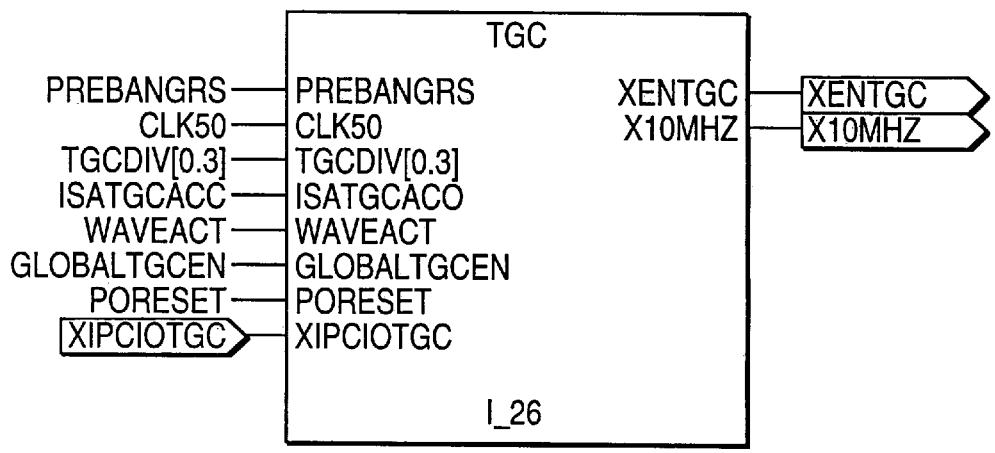
FIG. 9 (comprising FIGS. 9A, 9B, 9C, 9D, 9E and 9F) is a block diagram of a comparator FPGA shown in FIG. 2.
Figure 9A:
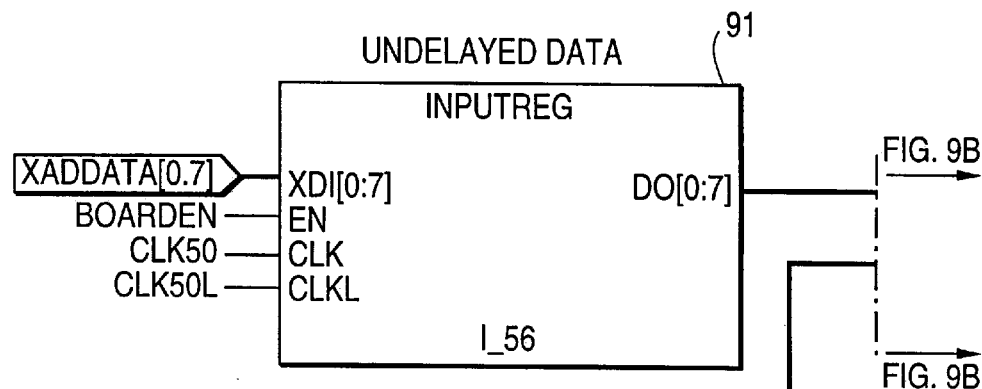
Figure 9A:
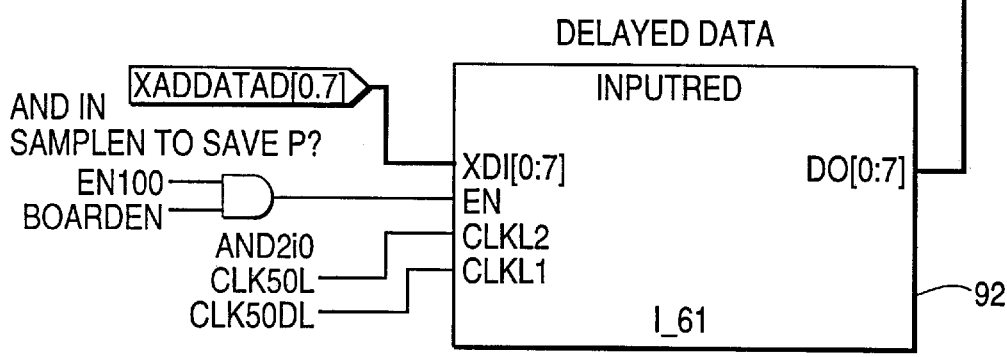
Figure 9B:
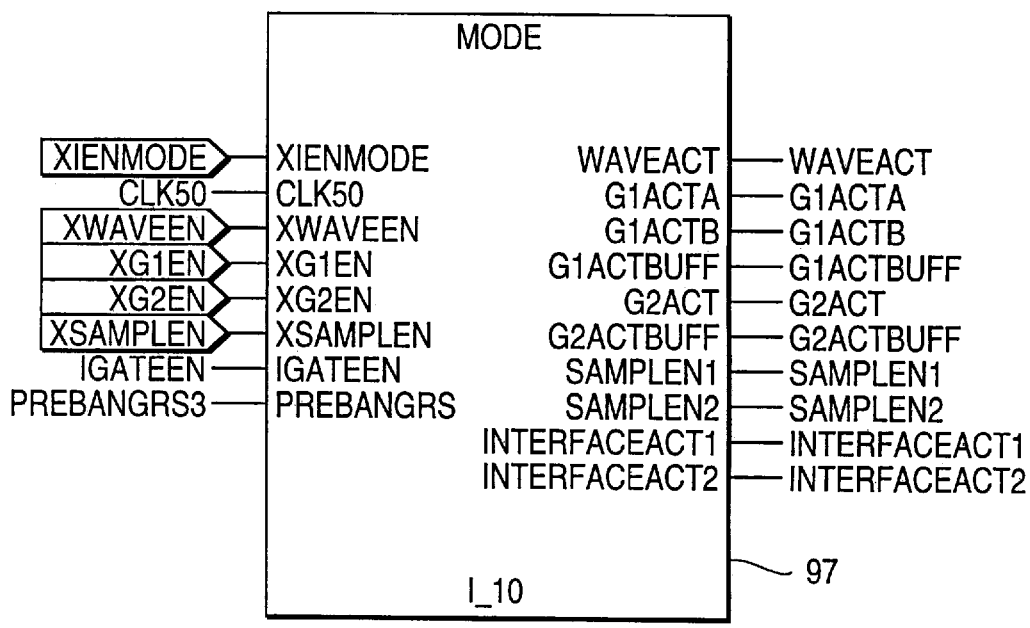
Figure 9B:
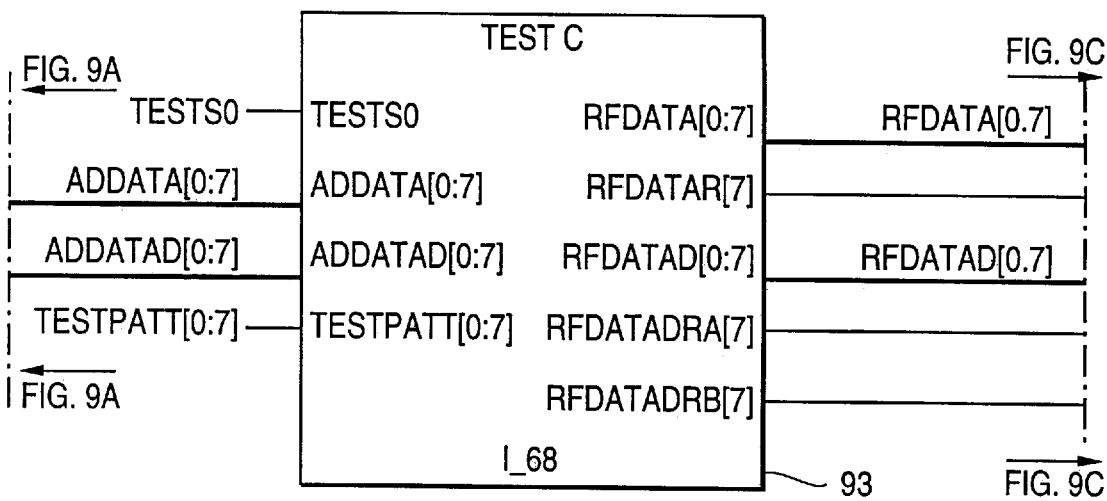
Figure 9C:
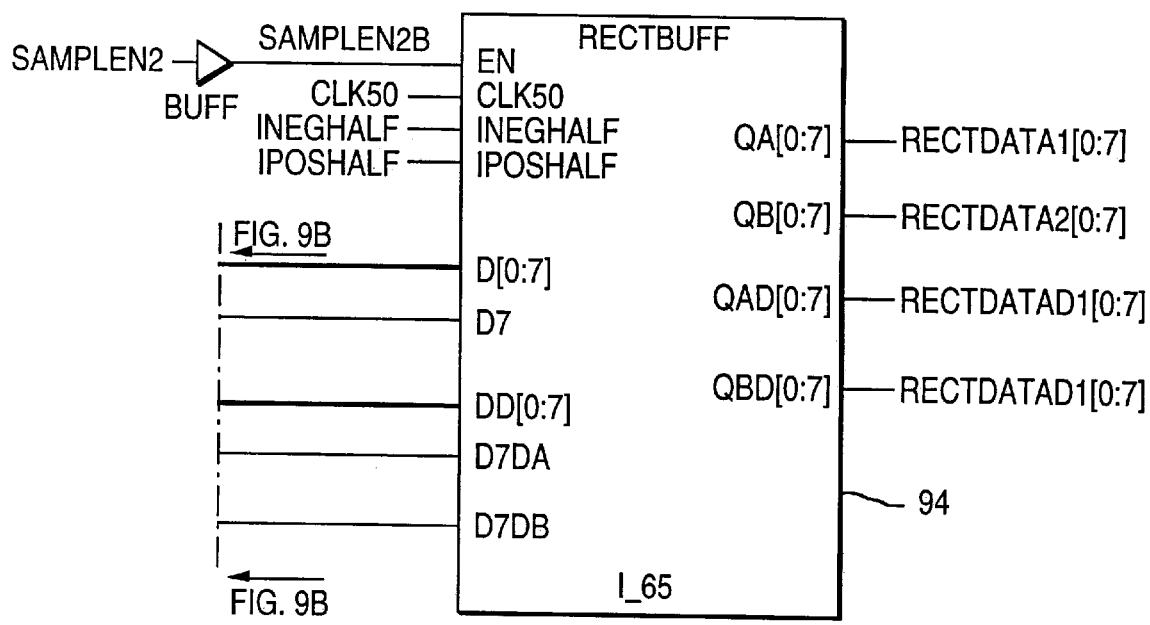
Figure 9D:
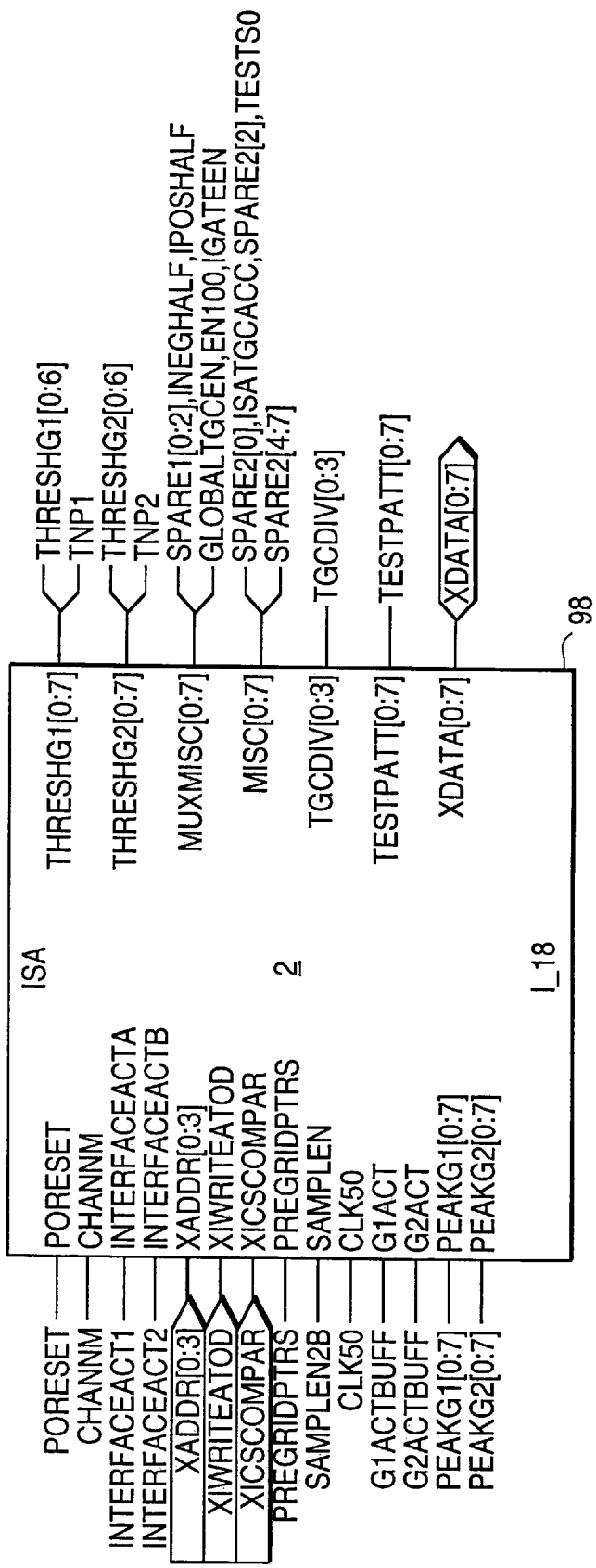
Figure 9E:
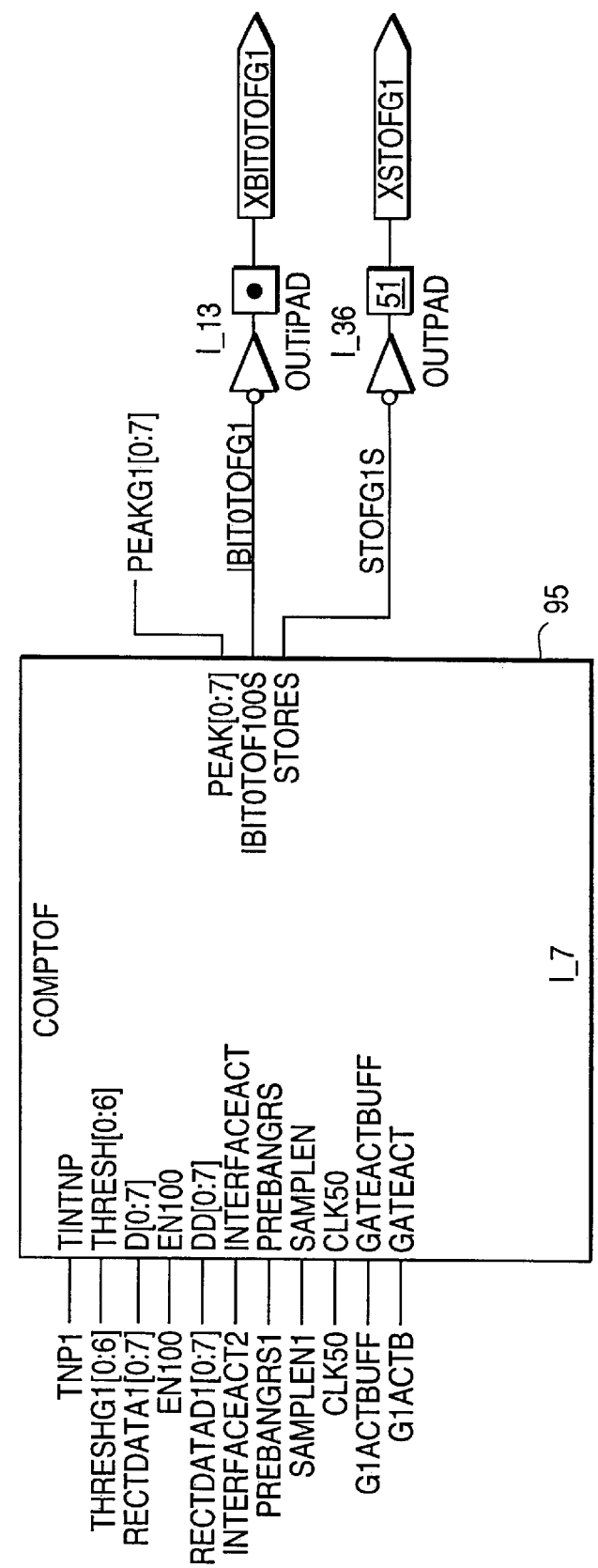
Figure 9F:
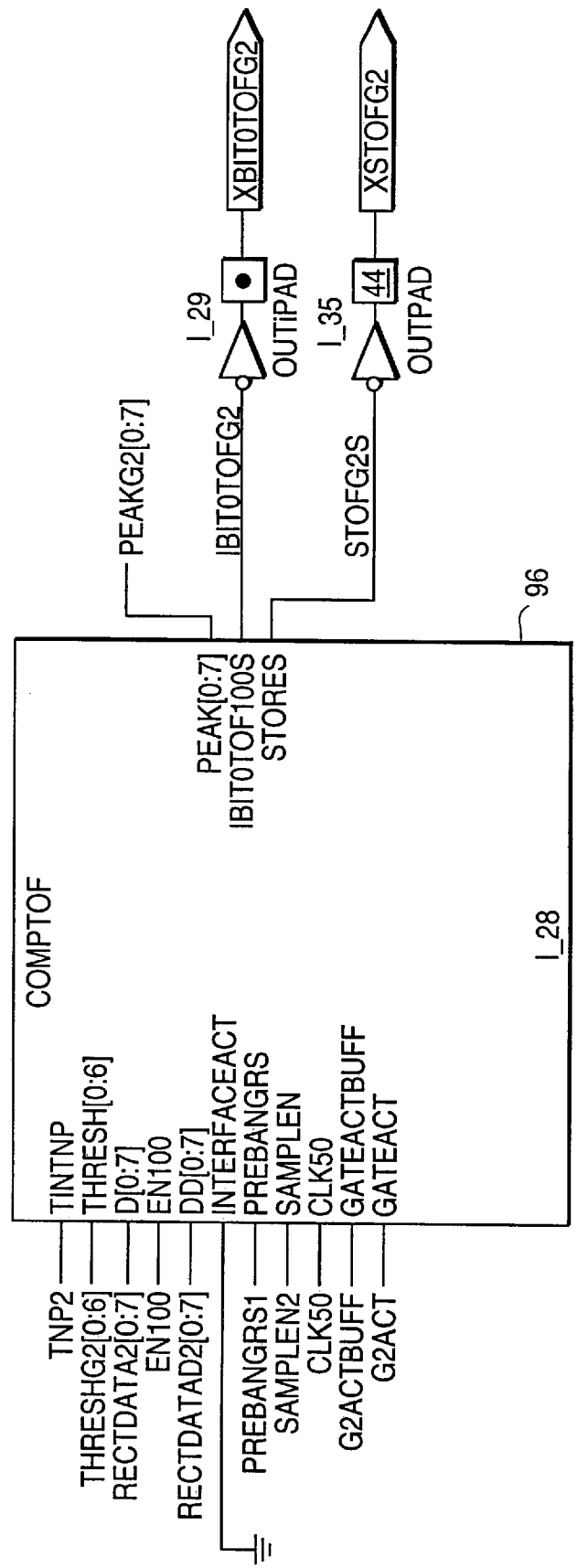
Figure 10A:
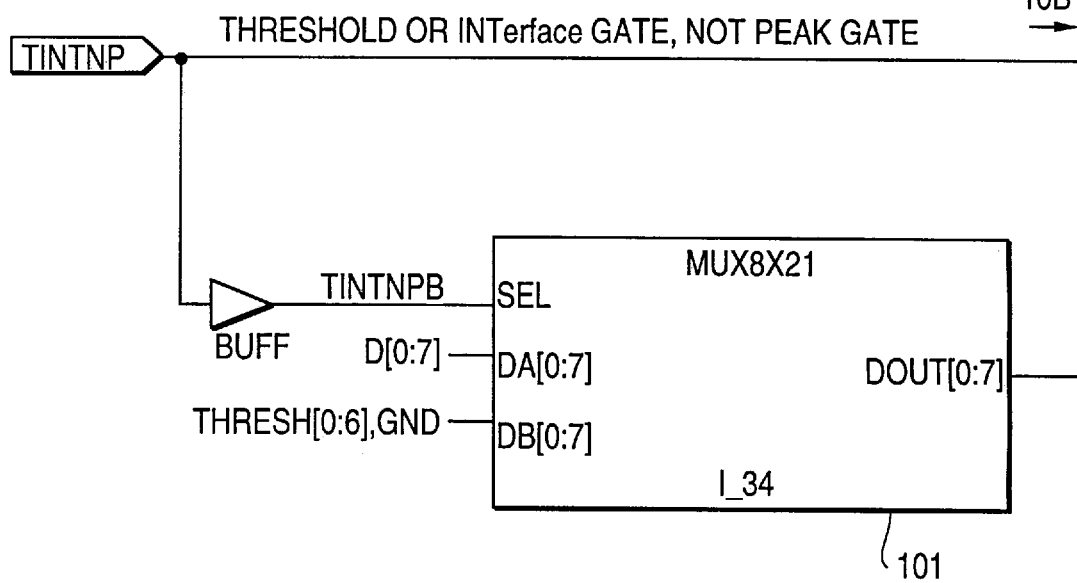
FIG. 10 (comprising FIGS. 10A, 10B, 10C, 10D, 10E and 10F) is a block diagram of a compare time-of-flight COMPTOF circuit shown in FIG. 9.
Figure 10A:
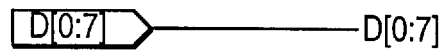
Figure 10A:
Figure 10A:
Figure 10B:
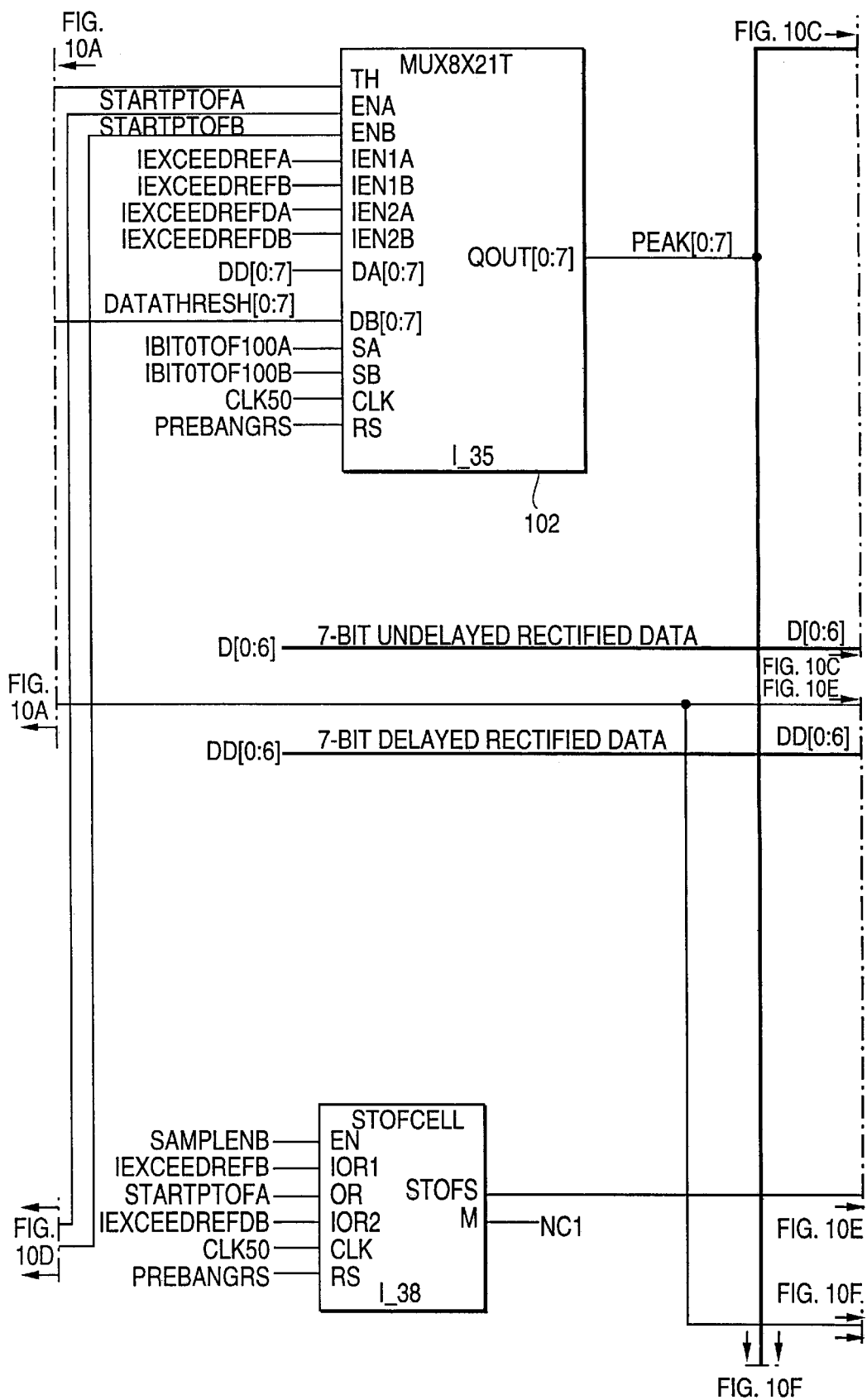
Figure 10C:
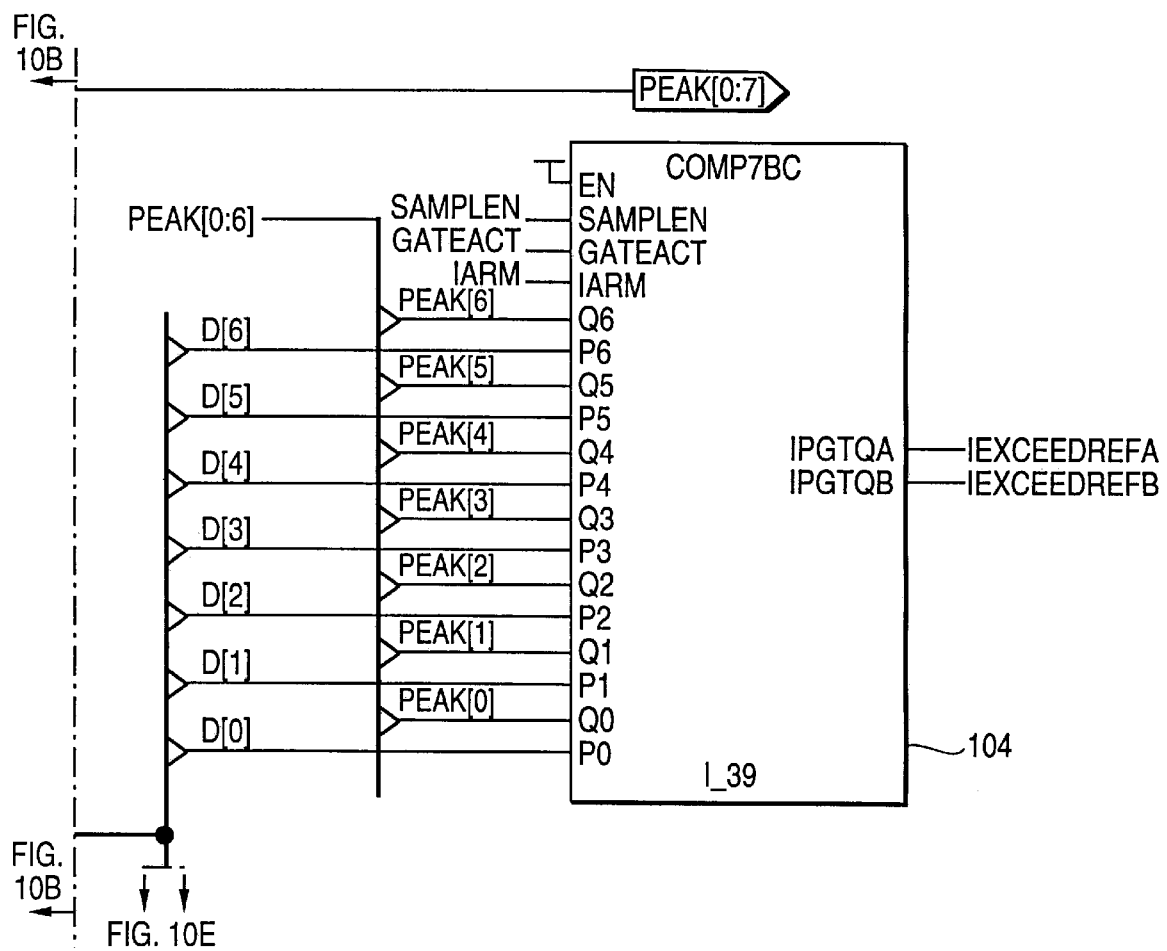
Figure 10D:
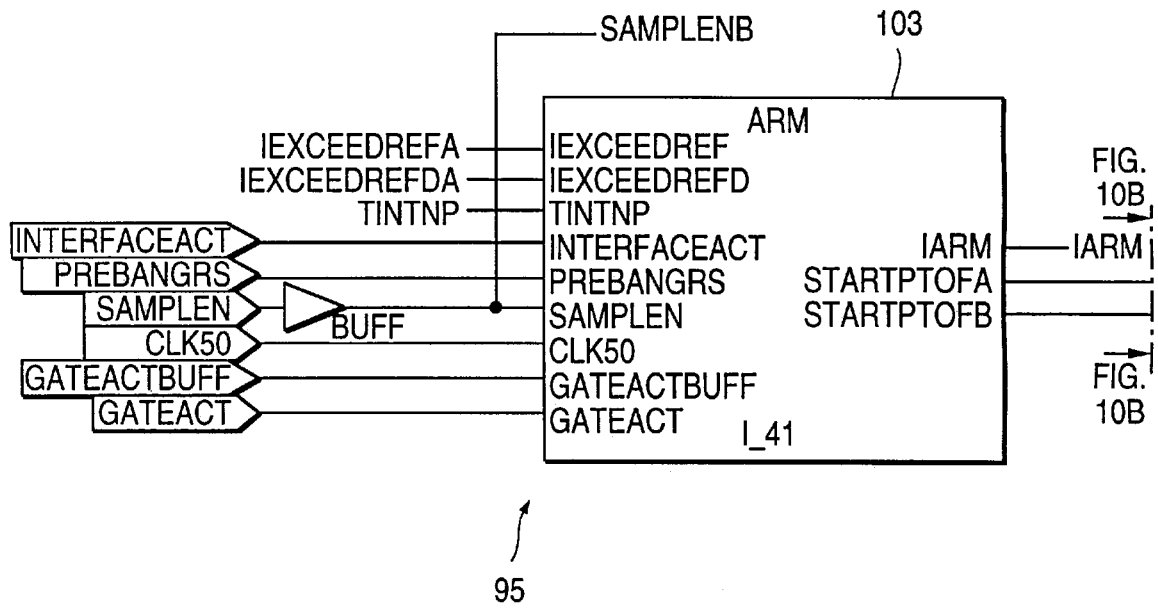
Figure 10E:
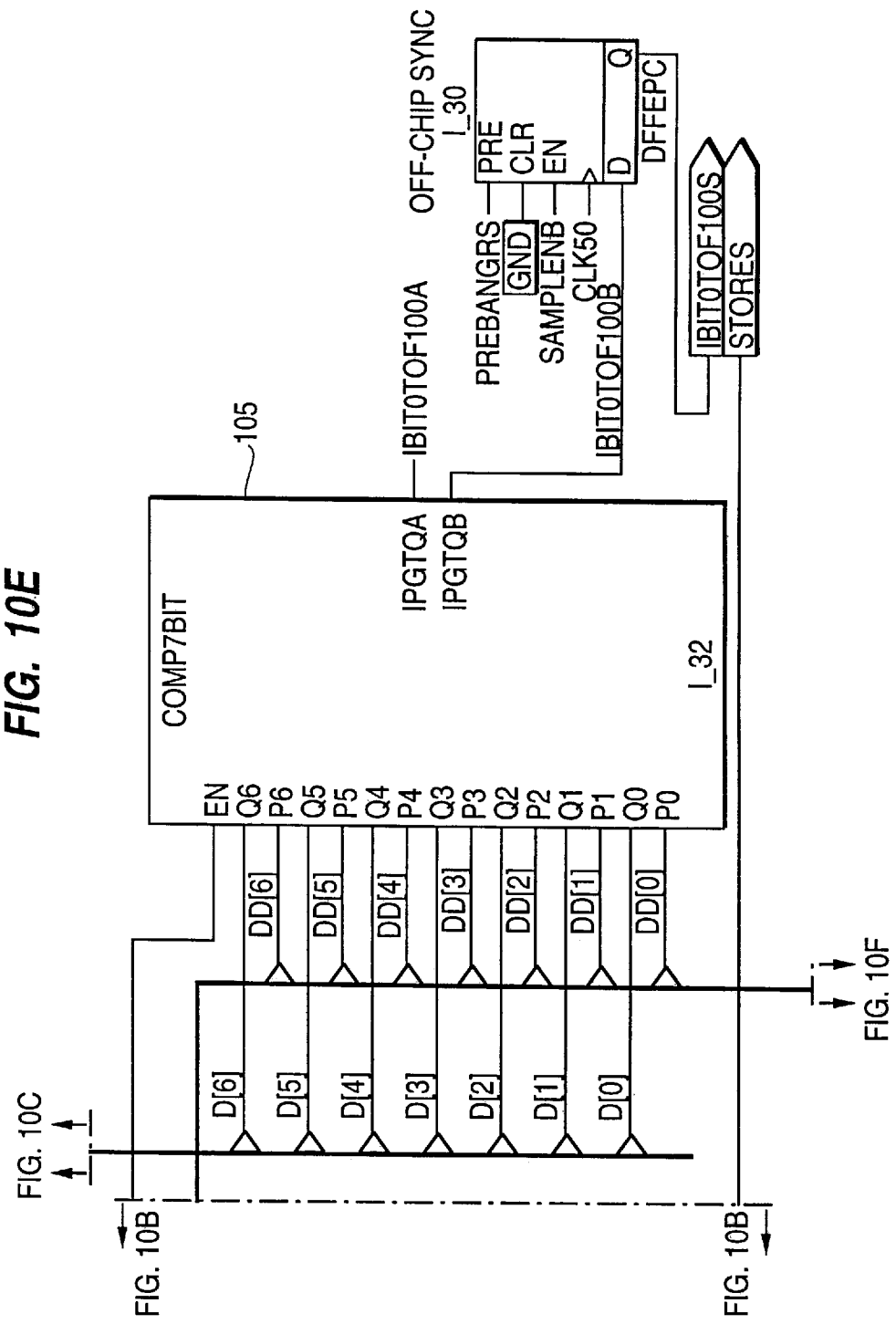
Figure 10F:
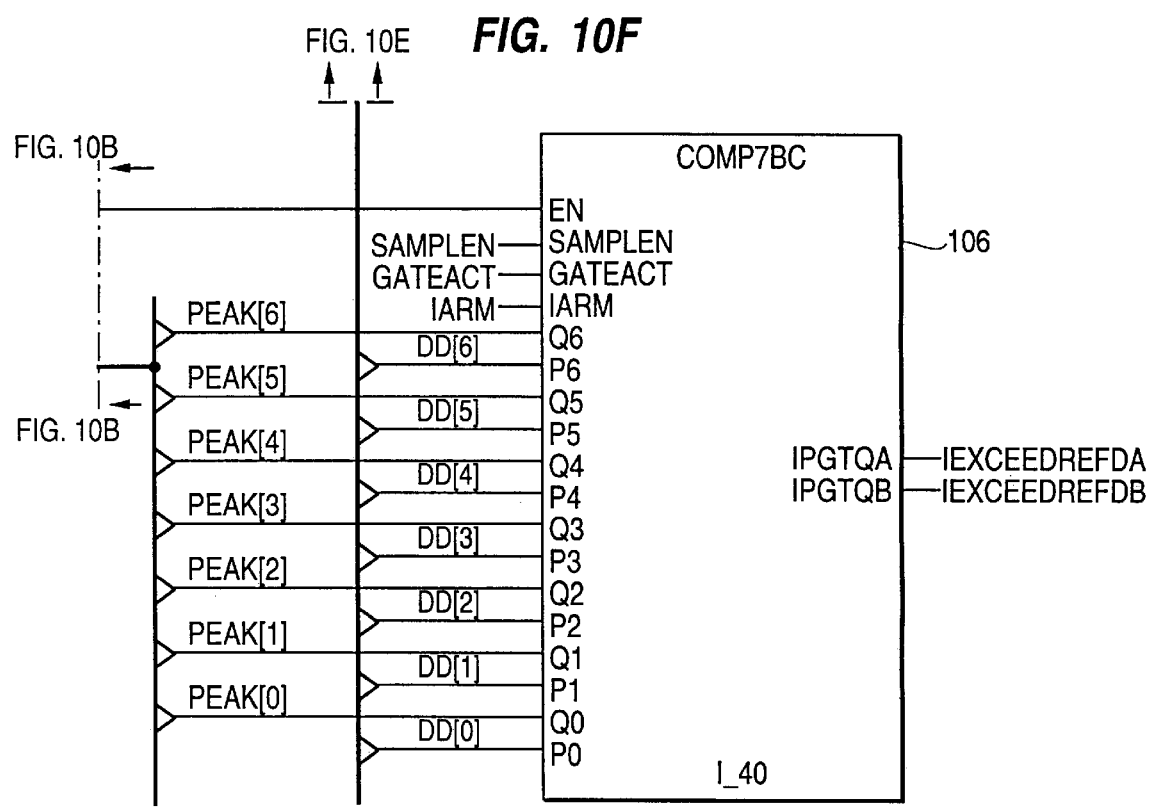
Figure 11A:
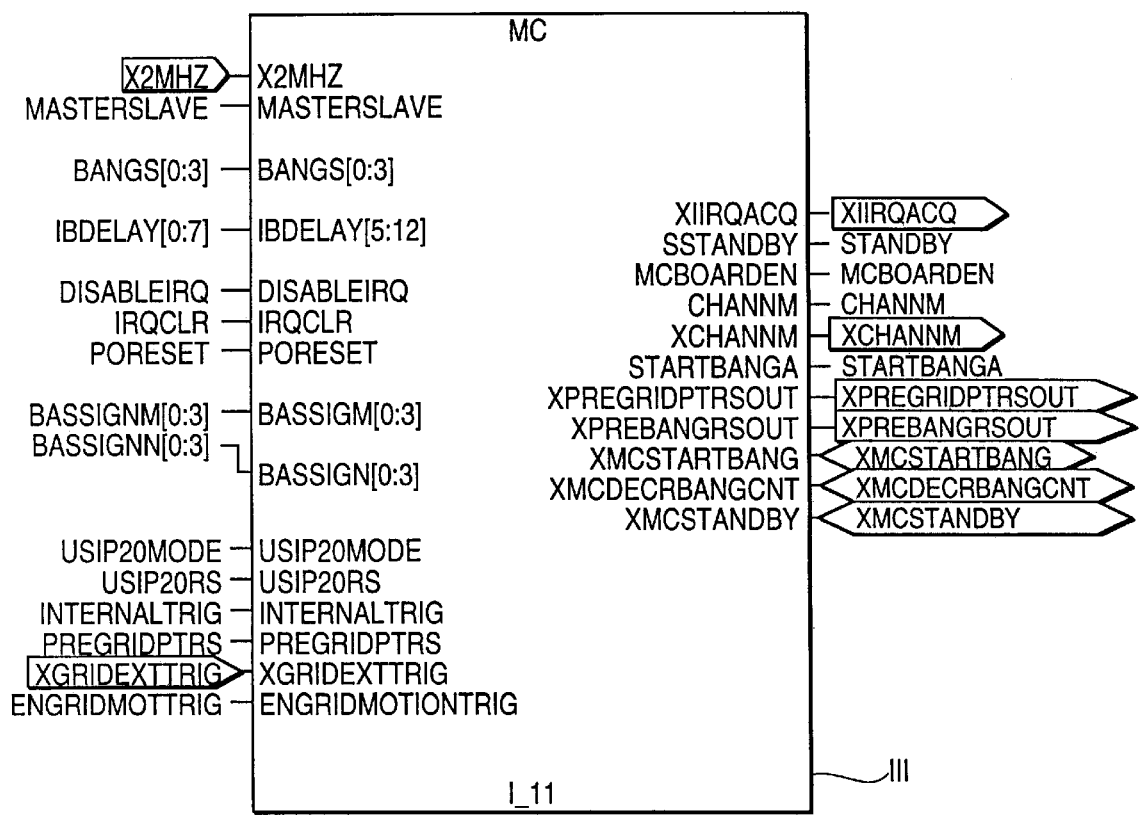
FIG. 11 (comprising FIGS. 11A, 11B, 11C and 11D) is a block diagram of a timer FPGA shown in FIG. 2.
Figure 11A:
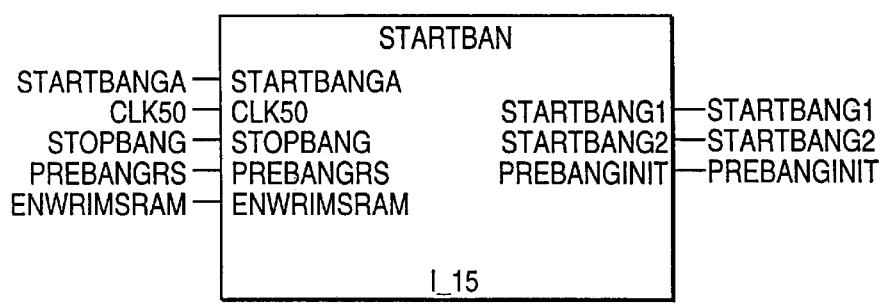
Figure 11A:
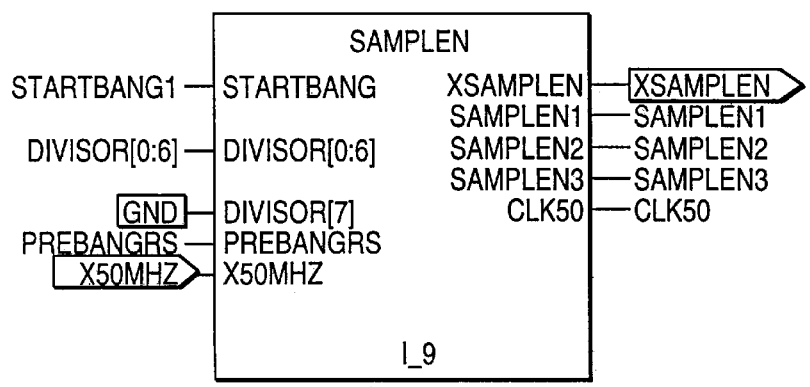
Figure 11B:
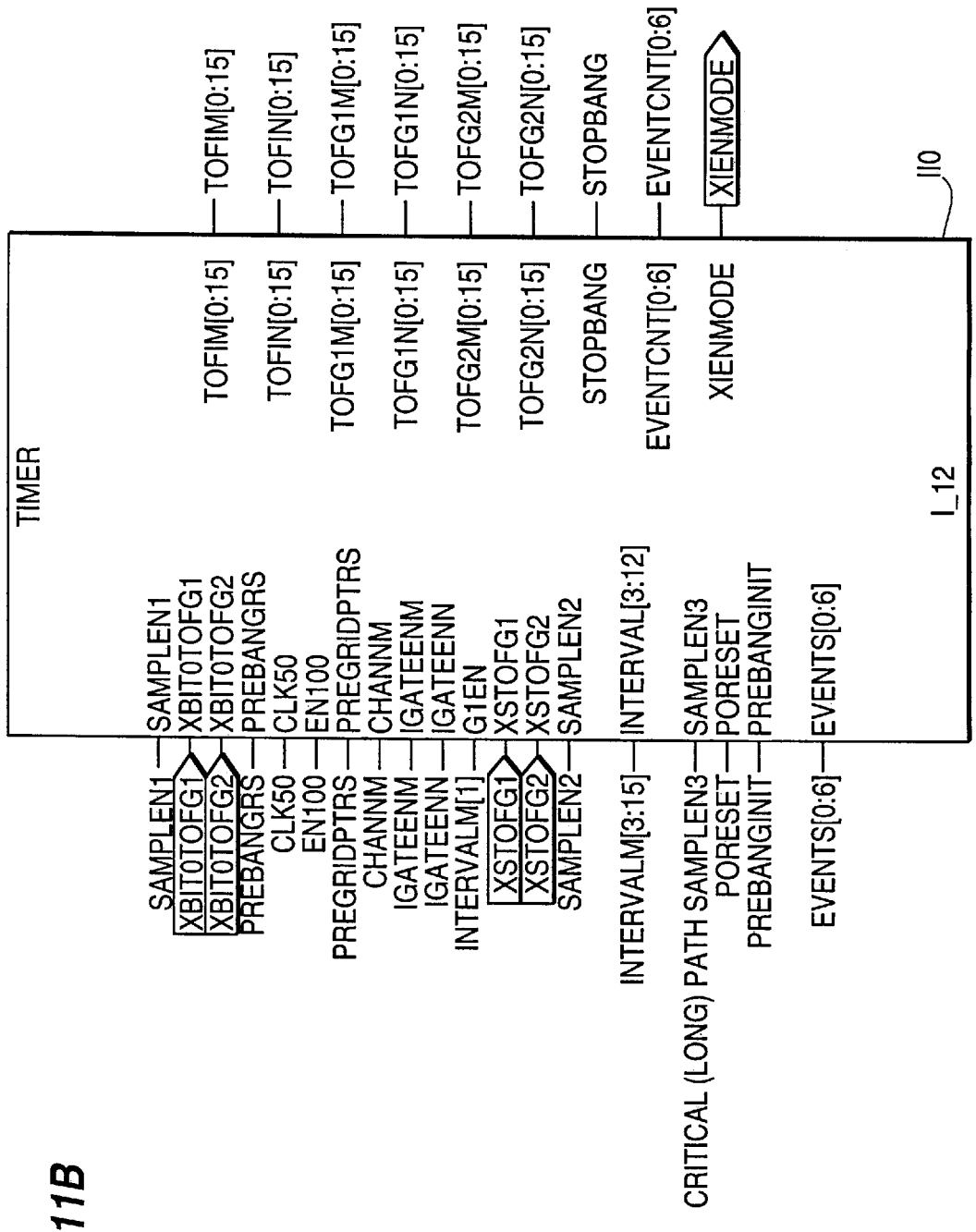
Figure 11C:
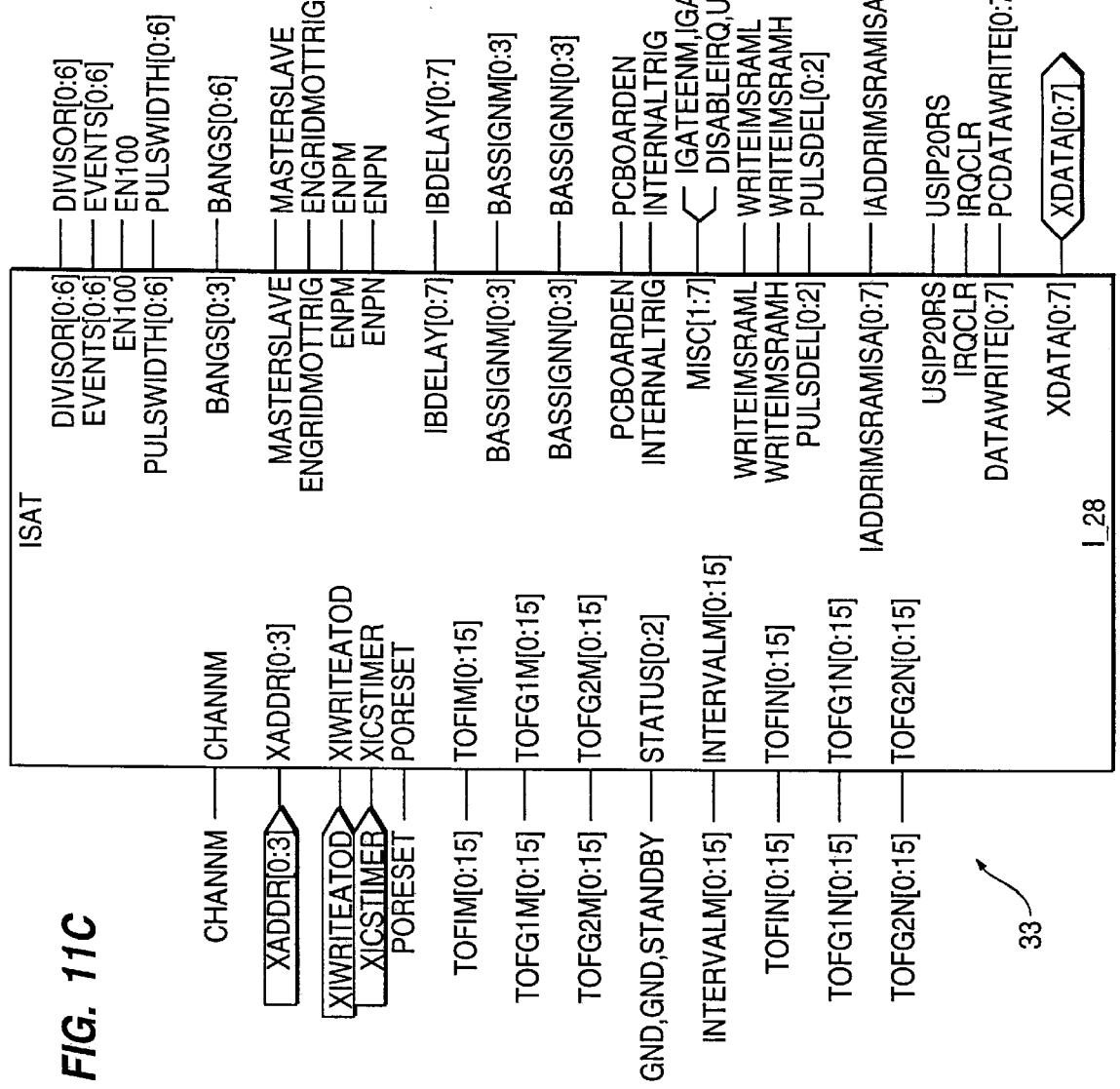
Figure 11D:
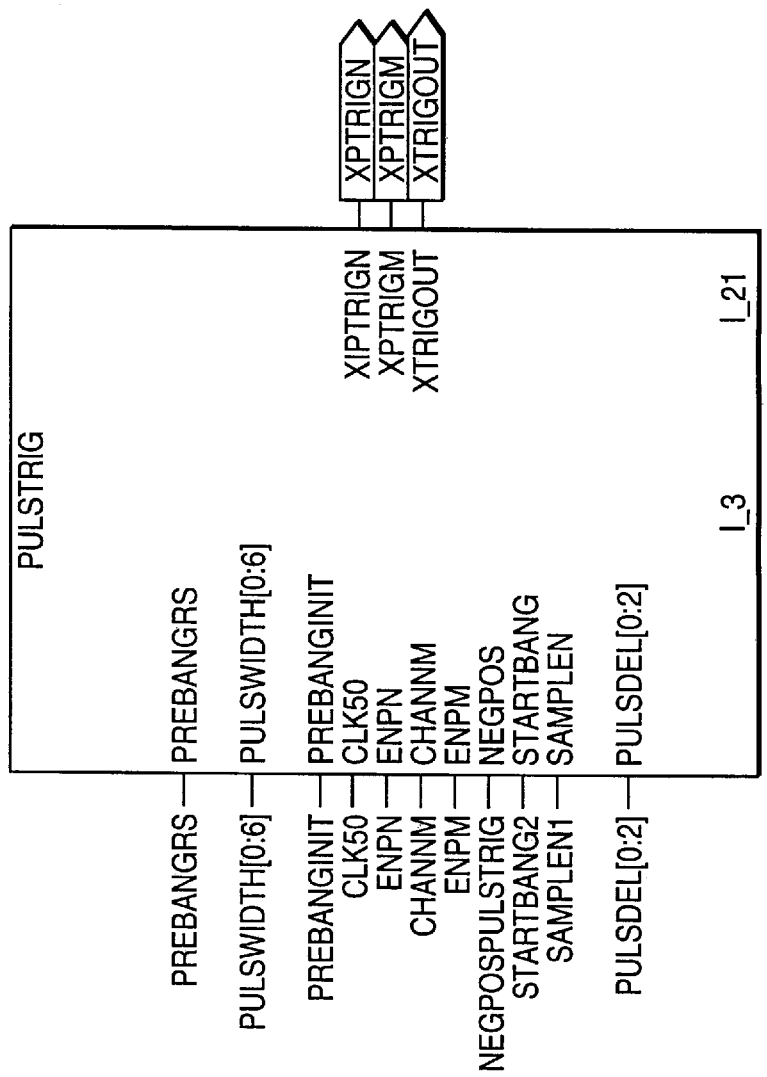

With reference to FIG. 3, a control signal bus WRITELTT (0:2) signal, which is supplied to the FIFOWRIT circuit 46 from the RLL circuit 47, controls the writing of 00h control codes in less-than-threshold counts LTTCNT to the waveform FIFO's 29 and 30. The signal IRLLWAVEEN controls the writing of unmodified waveform data to the waveform FIFO's 29 and 30 with waveform data passing through the FIFOWRIT circuit 46 before being input to the shift-register FIFO's 26 and 27. As stated above, while the signal WAVE-ACT is equal to 1, waveform data flows continuously through the prestore FIFO's 26 and 27. The FIFOWRIT circuit 46 is shown in more detail in FIG. 7 with a PRE-STORE circuit 80 within the FIFOWRIT circuit 46 being shown in further detail in FIG. 8. The PRESTORE circuit 80 generates outputs which control the read-enable and write-enable lines of the prestore FIFO's 26 and 27 so that data is written to the FIFO's 29 and 30 for four to sixteen sample time pairs before the data is read out of them by the waveform FIFO's 29 and 30. By storing the data for a number of samples time pairs in the shift register FIFO's 26 and 27 before the data is read, the waveform FIFO's 29 and 30 are able to store data that is relatively old with respect to the time of the threshold crossing and can thereby prestore the data.

A WAVELENG circuit 81 shown in FIG. 7 counts the total number of words stored during a single waveform acquisition. The total number of words stored during a single waveform acquisition is needed since the exact number of words stored to the waveform FIFO's 29 and 30 depends to a great extent on the exact nature of the ultrasonic signal being processed. With this count for the total number of words, the CPU 9 in the ultrasonic testing system 10 can determine how many words to read and attribute to the various channels.

As discussed above, the ultrasonic testing system 10 can perform as a video rectifier and filter and also a threshold-based run-length encoder. Additionally, the ultrasonic testing system 10 can combine the function of a video rectifier and filter with a threshold-based run-length encoder to achieve compression ratios which are approximately the product of the ratios for the individual functions. To combine these functions, the video rectifier and filter function is enabled and then the RLL circuit 47, FIFOWRIT circuit 46, and the PRESTORE circuit 80 are each provided with a copy of the video enable signal VIDEOEN so that instead of processing a new wave-form sample each sample enable period, these circuits process a new sample only once for each video enabled period.

The comparator FPGA 32 incorporates a signed peak and time-of-flight (P+TOF) flaw gate for searching a received ultrasonic transducer signal and storing a single peak amplitude and polarity of the signal and the time-of-flight corresponding to that peak for a user defined search time interval. The comparator FPGA 32 can compress the essential information present in the wave-form into just 3 bytes in those cases where an actual waveform record is not required.

With reference to FIG. 9, which represents a more detailed diagram of the comparator FPGA 32, the digital data from the A/D converter 21 is routed through a pair of input registers 91 and 92 with register 91 receiving the undelayed data and register 92 receiving the delayed data. The data from registers 91 and 92 are supplied to a TEST circuit 93 and then to a rectifier and buffer circuit RECT-BUFF 94, whose operation is similar to that of rectifier and buffer circuit RECTBUFF 44 shown in FIG. 3. The rectifier and buffer circuit RECTBUFF 94 supplies its outputs to a comparator/time-of-flight circuit COMPTOF 95 and to a comparator/time-of-flight circuit COMPTOF 96. The COMPTOF circuits 95 and 96 perform most of the logic for determining the peak and time-of-flight of the data signal. The COMPTOF circuits 95 and 96 output the peak value of the data signal as a data signal PEAKx(0:7), output a signal BITOTOFGx for selecting the odd or even sample time when the ultrasonic testing system 10 is operating at 100 MS/s, and output a signal STOFGX for signaling that the time-of-flight should be stored.

A MODE circuit 97 generates a group of signals having a general format of GxACT which define hardware gate search intervals requested by the user. When GxACT is equal to 1, the waveform data is searched for the peak amplitude value. With reference to FIG. 10, a multiplexer 102 is set to select the undelayed rectified data from the rectifier and buffer circuit 94. With each transition of a signal GxACT from 0 to 1, which defines the beginning of signed peak and time-of-flight interval (P+TOF), an ARM circuit 103 causes the first waveform sample to be stored in a peak register included within the multiplexer 102.

The rectified waveform samples which follow have their magnitudes compared to the present peak values stored in the multiplexer 102 with this comparison being performed by a pair of comparators 104 and 106. The comparator 104 is used to determine whether the new data is greater than the peak value stored in the multiplexer 102 and the comparator 106 is used to determine whether the new delayed data is greater than the peak value stored in the multiplexer 102. At sampling rates less than 100 MS/s, only the upper comparator 104 is used. If the amplitudes of the new delayed data and undelayed data are both less than the present peak value, then no action is taken. On the other hand, if the amplitude of either the delayed data or undelayed data is greater than the peak value stored in the multiplexer 102, then the current waveform sample overwrites the peak value stored in the multiplexer 102. Since both the delayed data and the undelayed data may be greater than the peak value stored in the multiplexer 102, the comparator 105 compares the magnitude of the delayed data to that of the undelayed data and signals the multiplexer 102 to select the larger of the two data samples for storage. At the end of each search interval, the peak value stored in the multiplexer 102 is recorded in one of several 8-bit registers in the ISAIN circuit shown in FIG. 4 according to the gate number and channel number. These registers may be read and displayed by the CPU 9 using the ISA bus interface circuit 13. The sign bit of each peak value is preserved by passing through the most-significant bit (D7) of the original input sample.

Figure 12A:
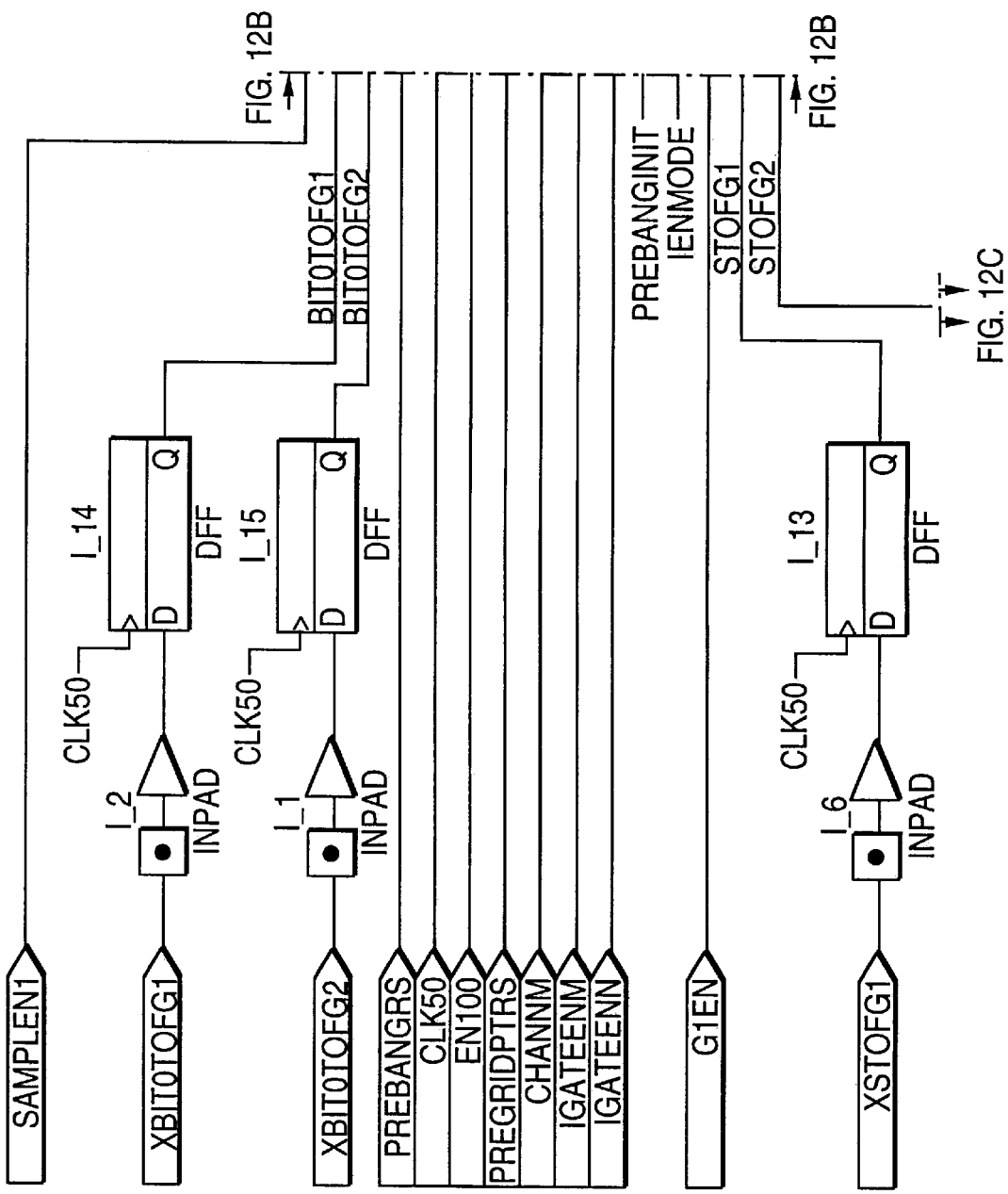
FIG. 12 (comprising FIGS. 12A, 12B, 12C and 12D) is a block diagram of a TIMER circuit shown in FIG. 11.
Figure 12D:
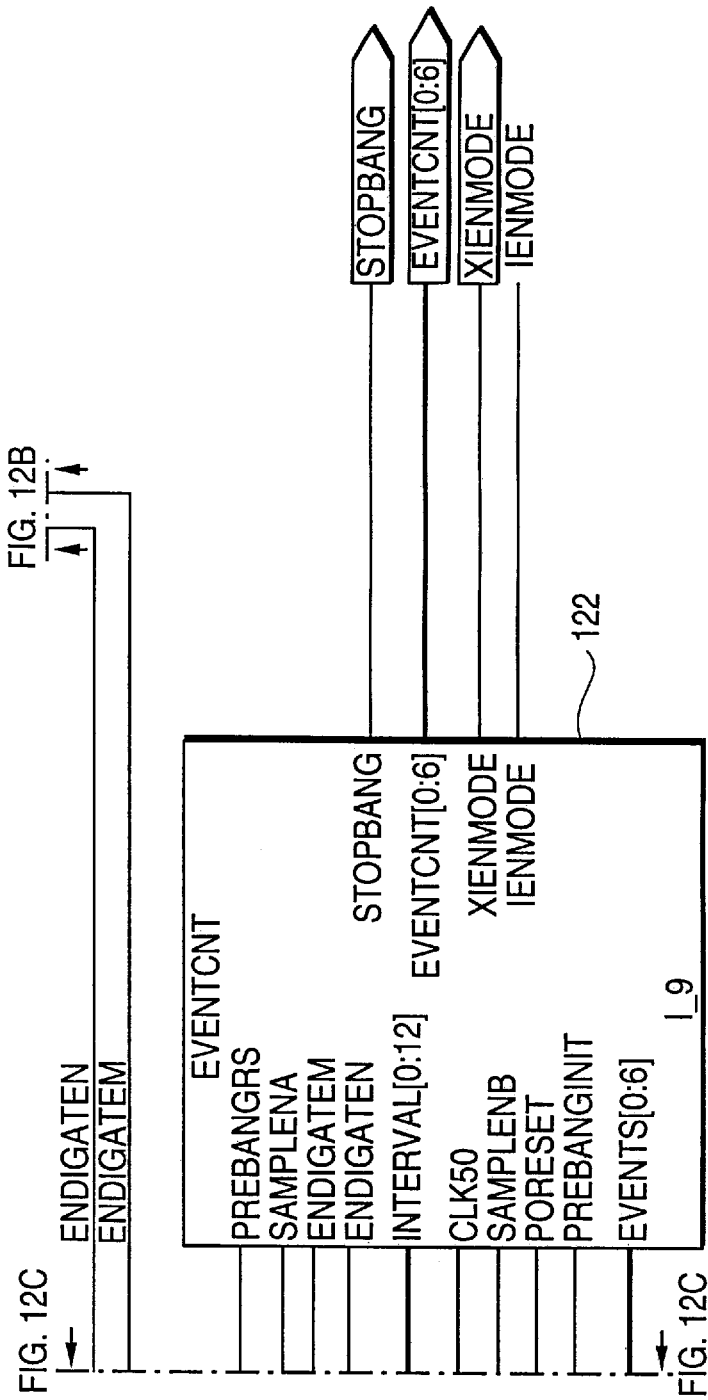
Figure 13A:
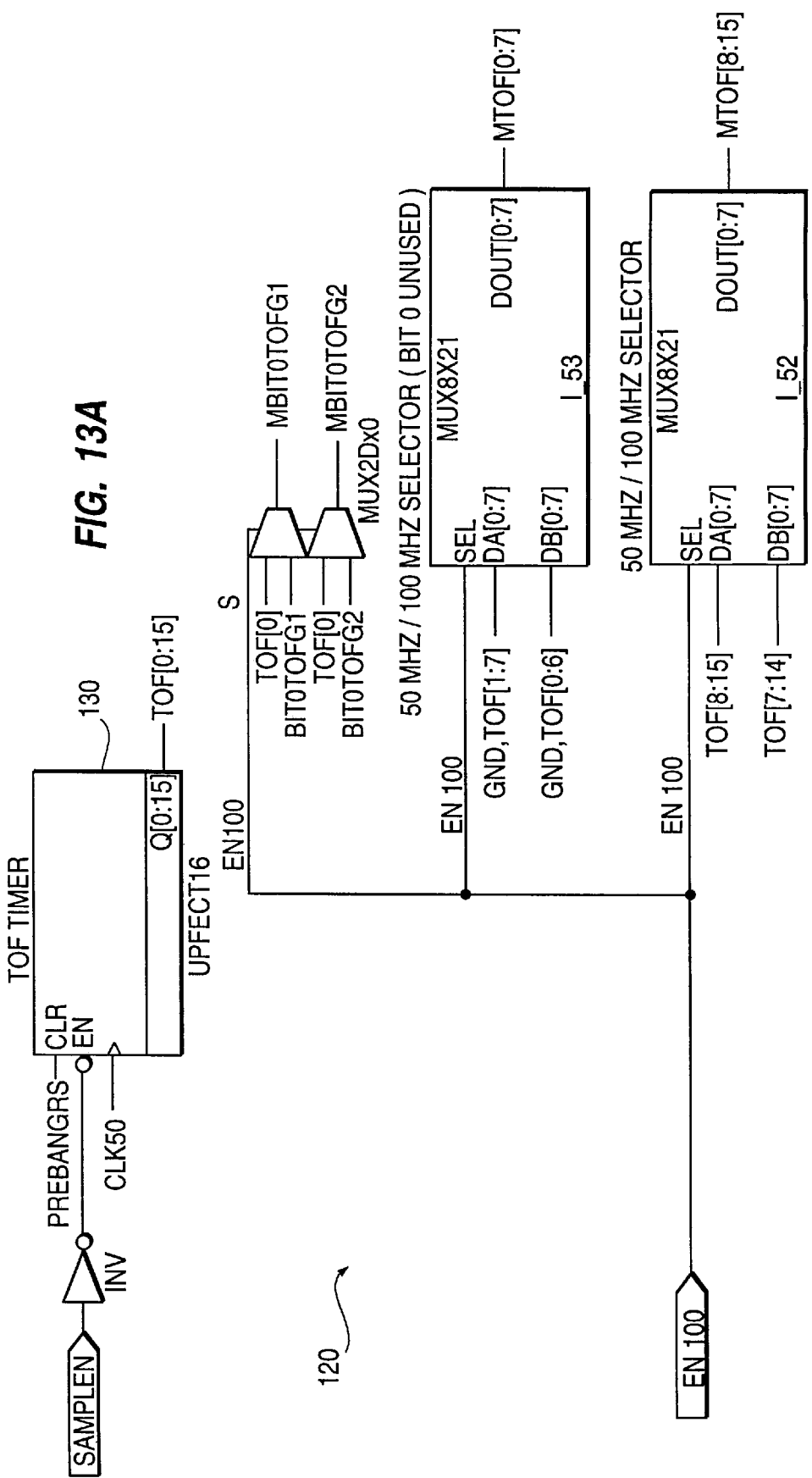
FIG. 13 (comprising FIGS. 13A, 13B, 13C and 13D) is a block diagram of a time-of-flight TOF circuit shown in FIG. 12.
Figure 13B:
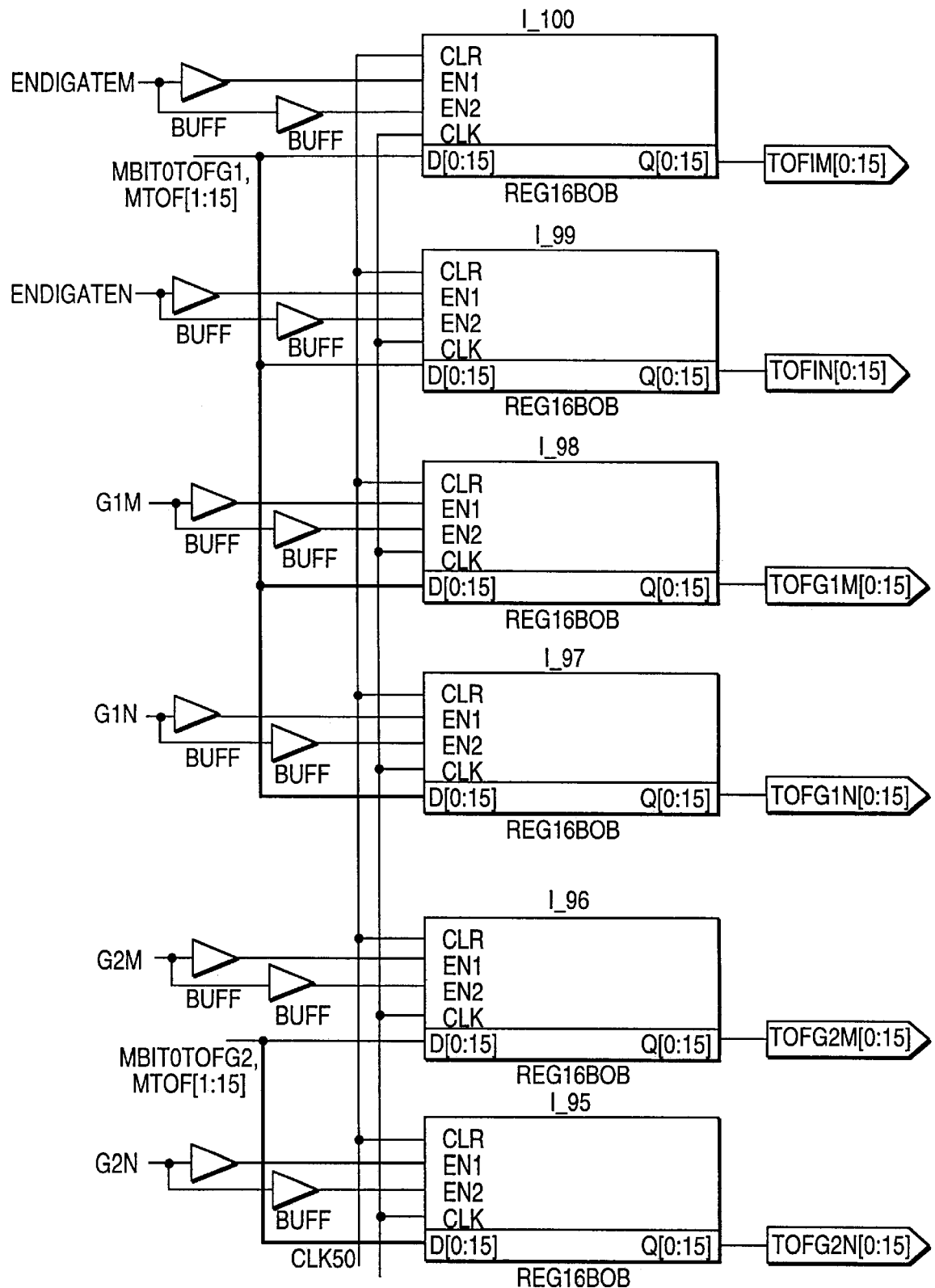
Figure 13C:
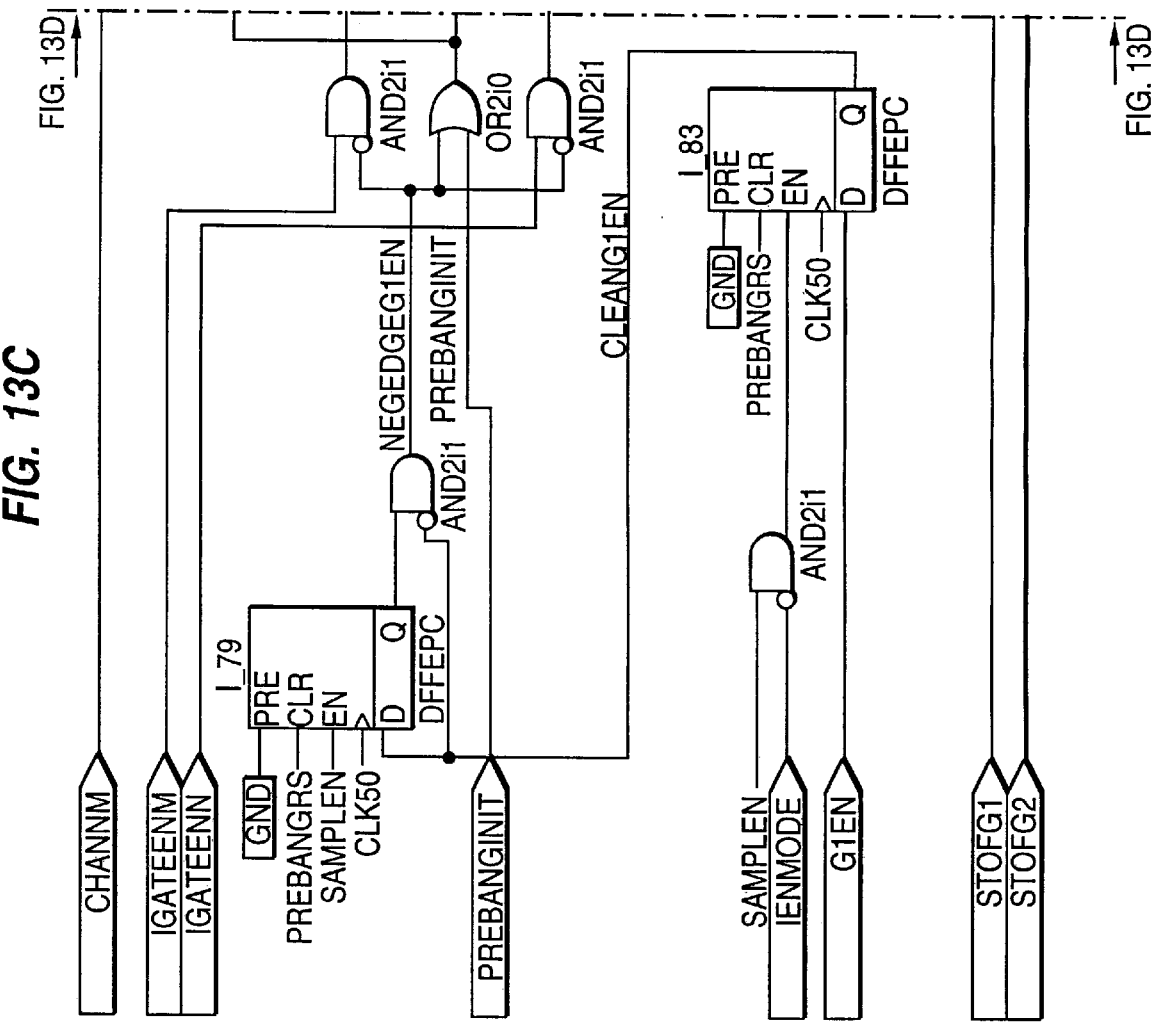
Figure 13D:
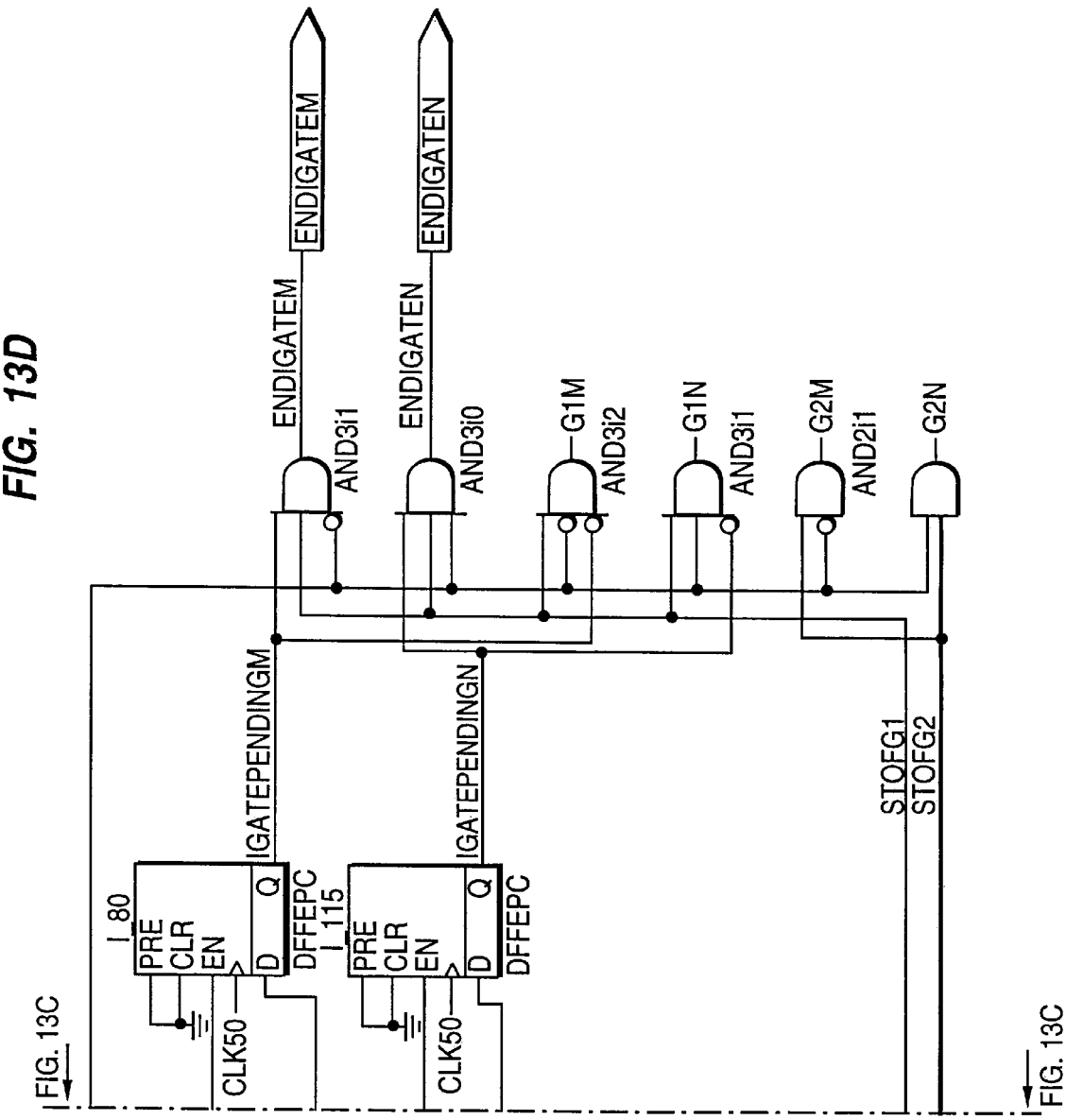

As shown in FIG. 2, the comparator FPGA 32 transmits the STOFGX signals and the BITOTOFGx signals to the timer FPGA 33 which includes time-of-flight counters. FIG. 11 provides a more detailed diagram of the timer FPGA 33 and FIG. 12 provides a more detailed diagram of a TIMER circuit 110 which is shown in FIG. 11. FIG. 13 further illustrates the time-of-flight circuit 120 shown in FIG. 12. As shown in FIG. 13, a time-of-flight counter 130 is a 16-bit counter for counting the number of sample enable periods after the "main bang." The main bang refers to the high-voltage pulse which causes the initial output pulse of ultrasonic energy from the ultrasonic transducer 7. Whenever a store time-of-flight STOFx pulse is received, the present time-of-flight is stored in an appropriate 16-bit time-of-flight register REG16BOB according to channel number, gate number, and type of gate. Since, at a sampling rate of 100 MS/s, two data samples are received for each 50 MHz clock period, the signal BIT0TOFGX is used for TOFGxy(0), TOF(0:14) is used for TOFGxy(1:15), and TOF(15) is discarded. The time-of-flight registers TOFGxy may be read by the CPU 9 through the ISA bus interface circuit 13.

In addition to storing the time-of-flight associated with a peak value, the ultrasonic testing system 10 can also search an ultrasound-derived signal and store the time-of-flight corresponding to the first excursion of the signal through a user selected threshold for a user defined search time interval. With reference to FIG. 10, while the signal GxACT is equal to 1, the magnitude of the rectified waveform sample is compared to a threshold value THRESH(0:6) by the two comparators 104 and 106, with only the upper comparator 104 being operative at a sampling rate less than 100 MS/s. If the amplitude of the data sample is less than the specified threshold THRESH, then no action is taken. On the other hand, if the amplitude of the sample is greater than the threshold THRESH, a store time-of-flight signal STOF is issued to the timer FPGA 33.

The comparators 95 and 96 therefore command the timer FPGA 33 to store the time-of-flight according to the first excursion of the signal through the threshold THRESH in a manner similar to that for the signed peak and time-of-flight described above. One difference, however, is that the reference value for comparison is not a present peak value of the sampled data but rather is a user-selected threshold THRESH. As a result, the data signal PEAK(0:6) is a static symbol and is equal to the user-selected threshold THRESH. Another difference is a stored time-of-flight pulse (STOF) is not necessarily issued at the beginning of each flaw gate. Further, another difference is that once a single store time-of-flight (STOF) has been issued, no more stored time-of-flight pulses (STOF) will occur during the gate interval.

Figure 14A:
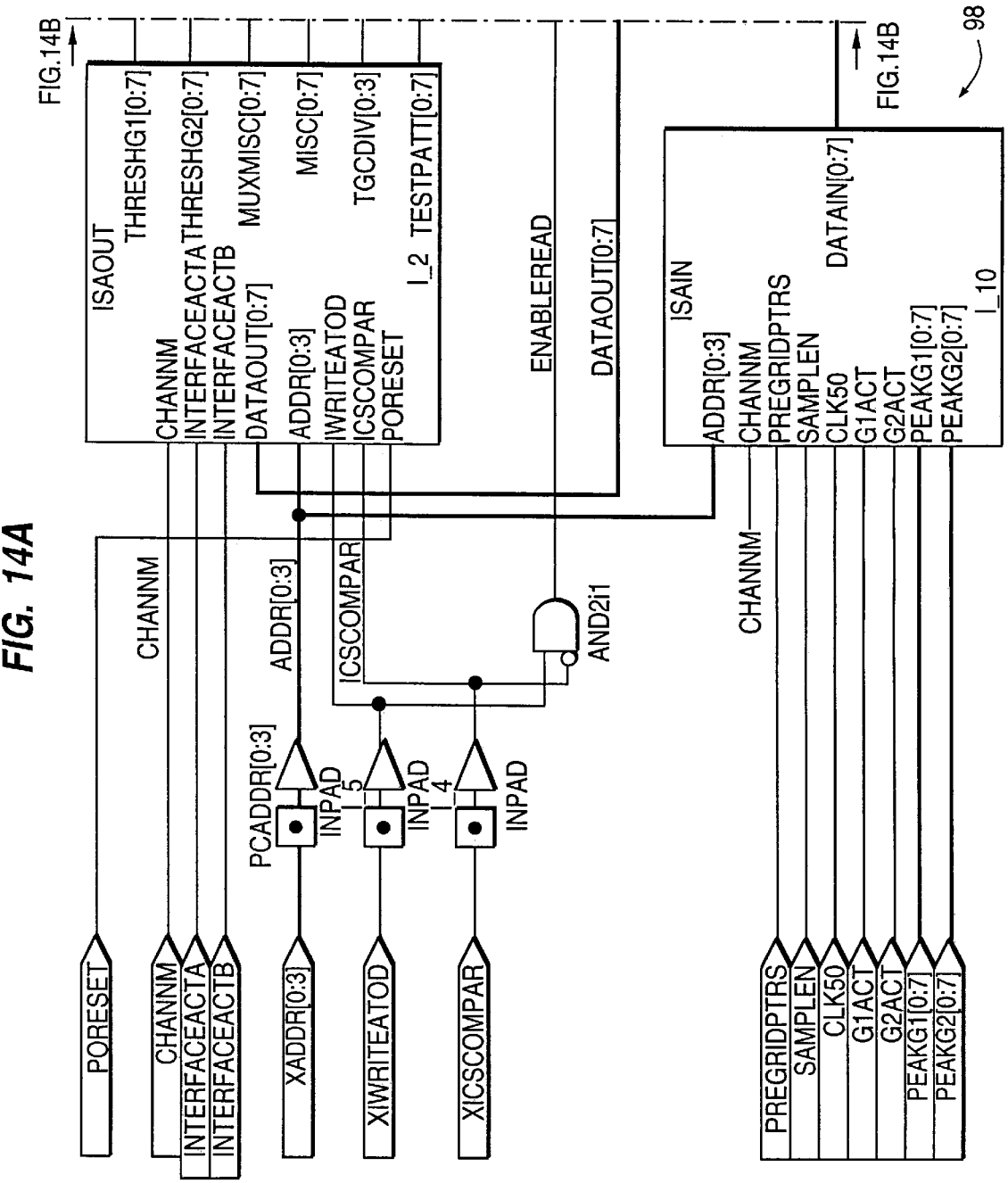
FIG. 14 (comprising FIGS. 14A and 14B) is a block diagram of an ISA circuit shown in FIG. 9.
Figure 14B:
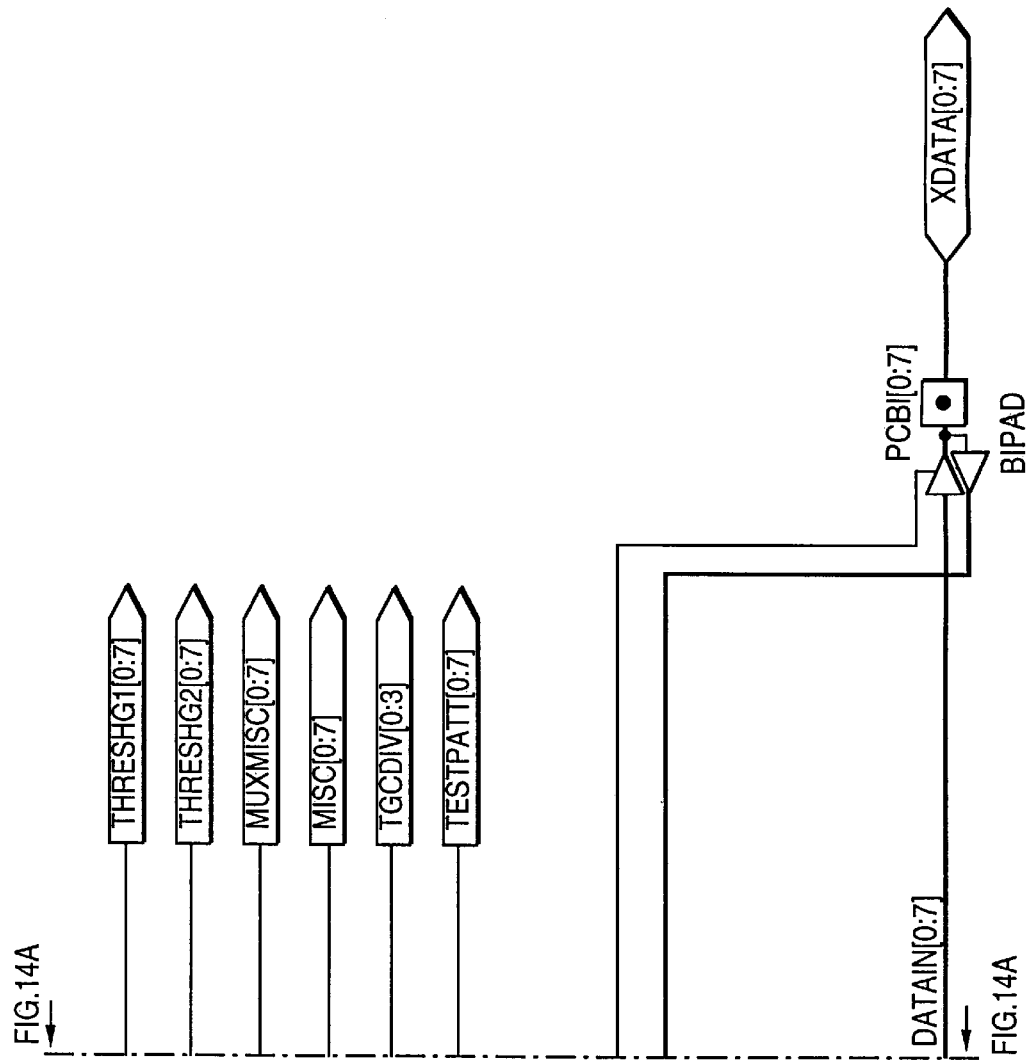
Figure 15B:
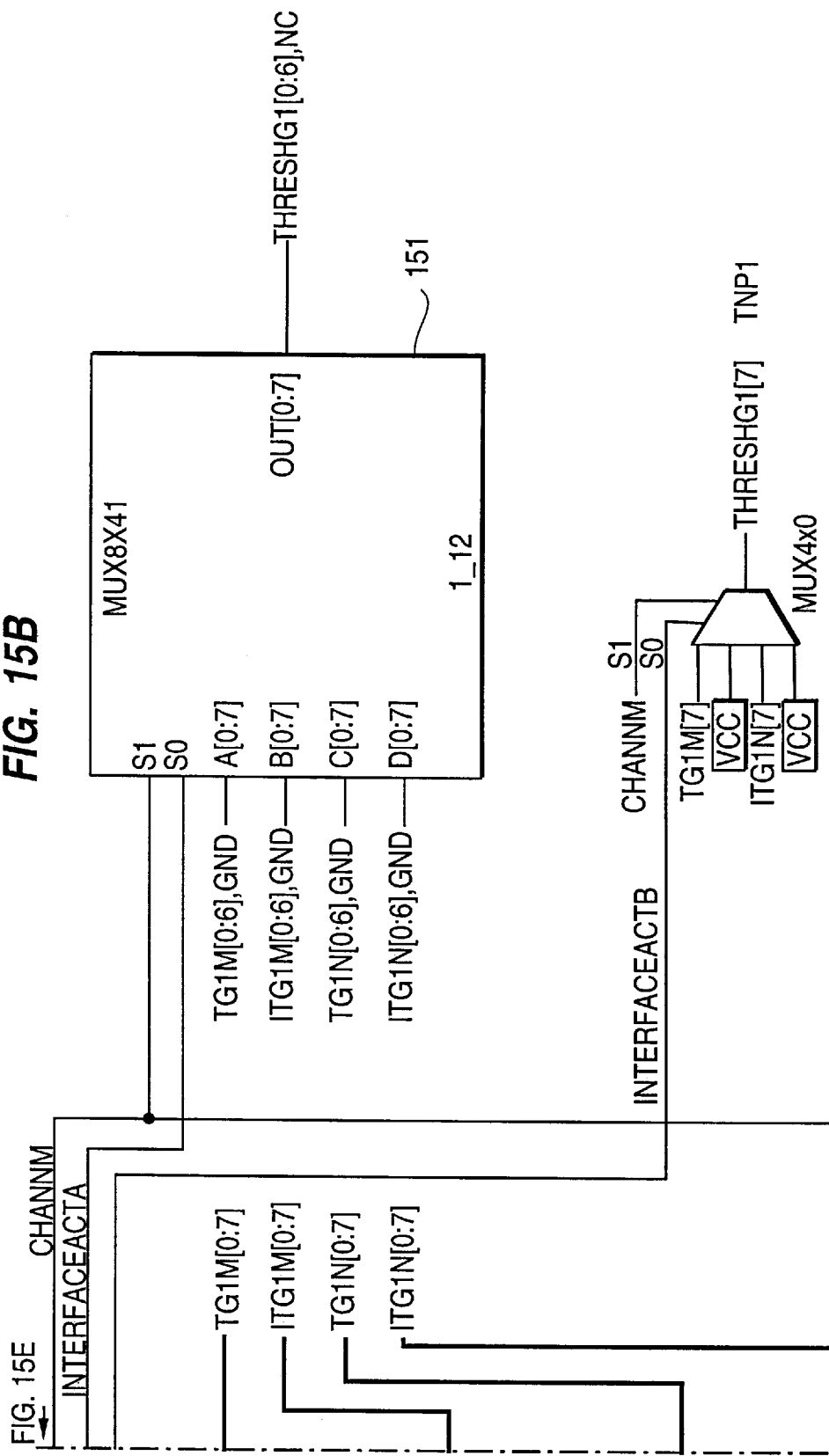
FIG. 15 (comprising FIGS. 15A, 15B, 15C, 15D and 15E) is a block diagram of an ISAOUT circuit shown in FIG. 14.
Figure 15C:
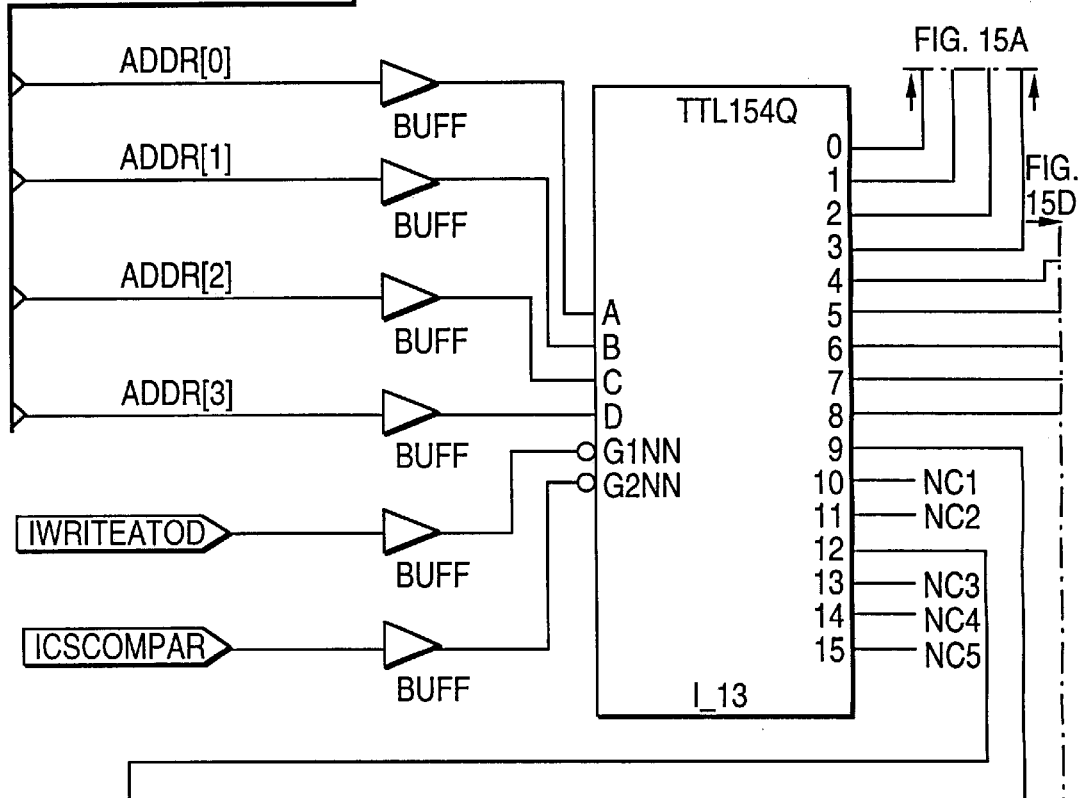
Figure 15C:
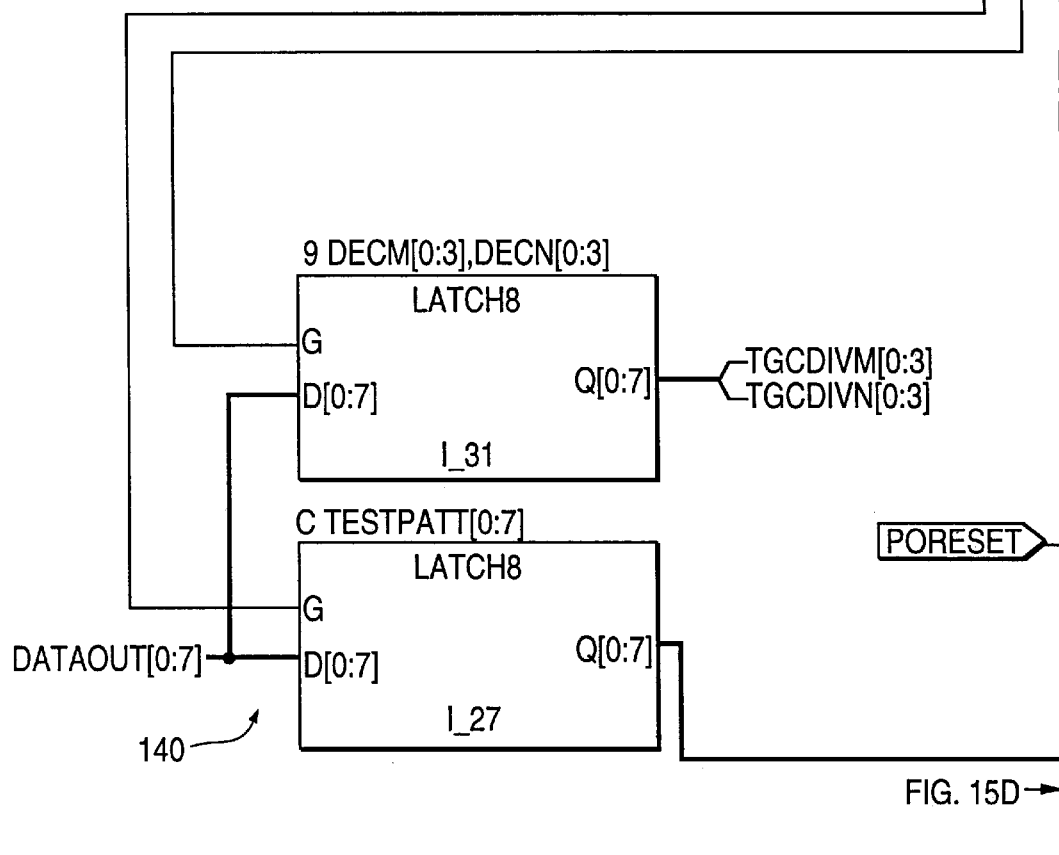
Figure 15D:
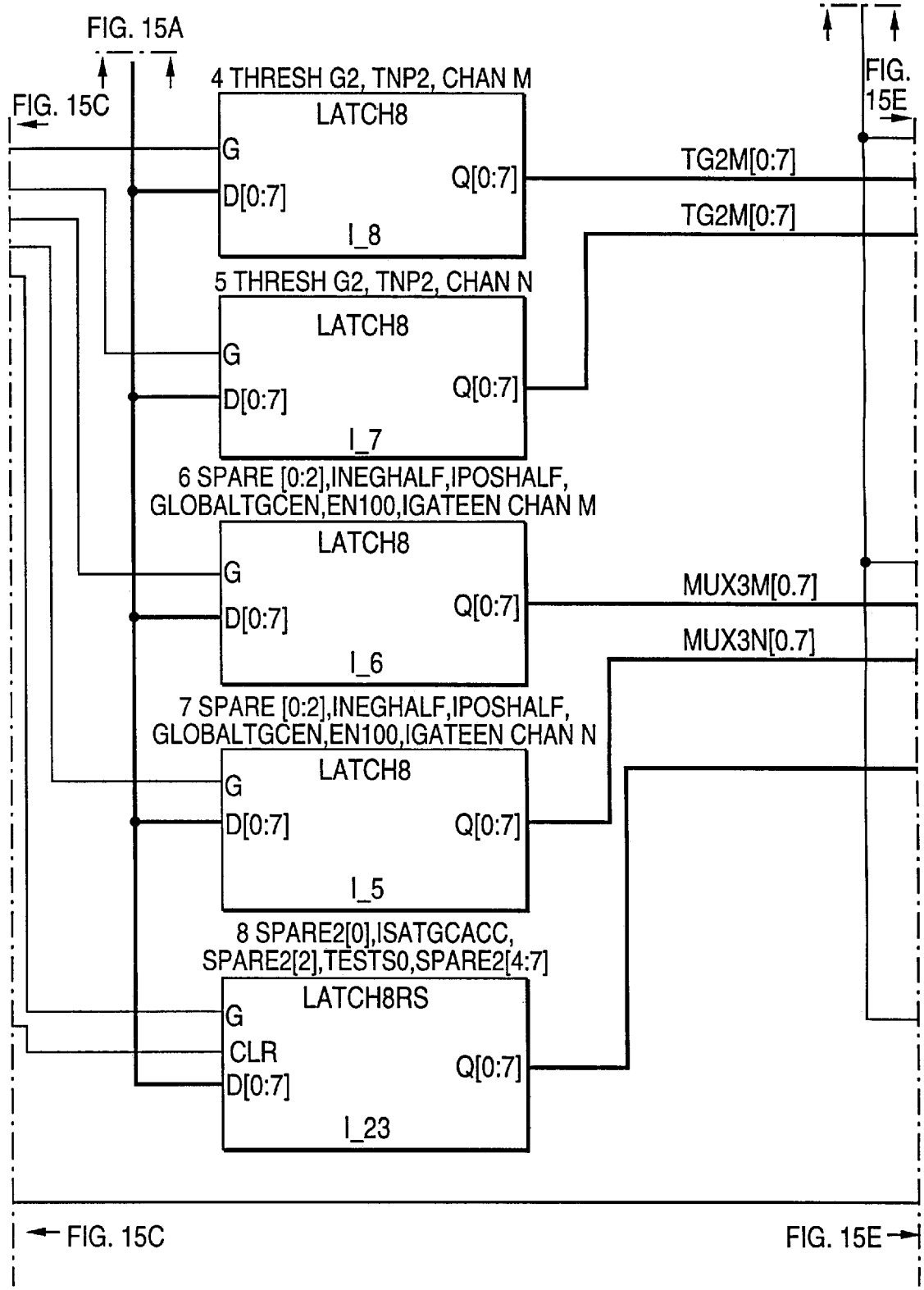
Figure 15E:
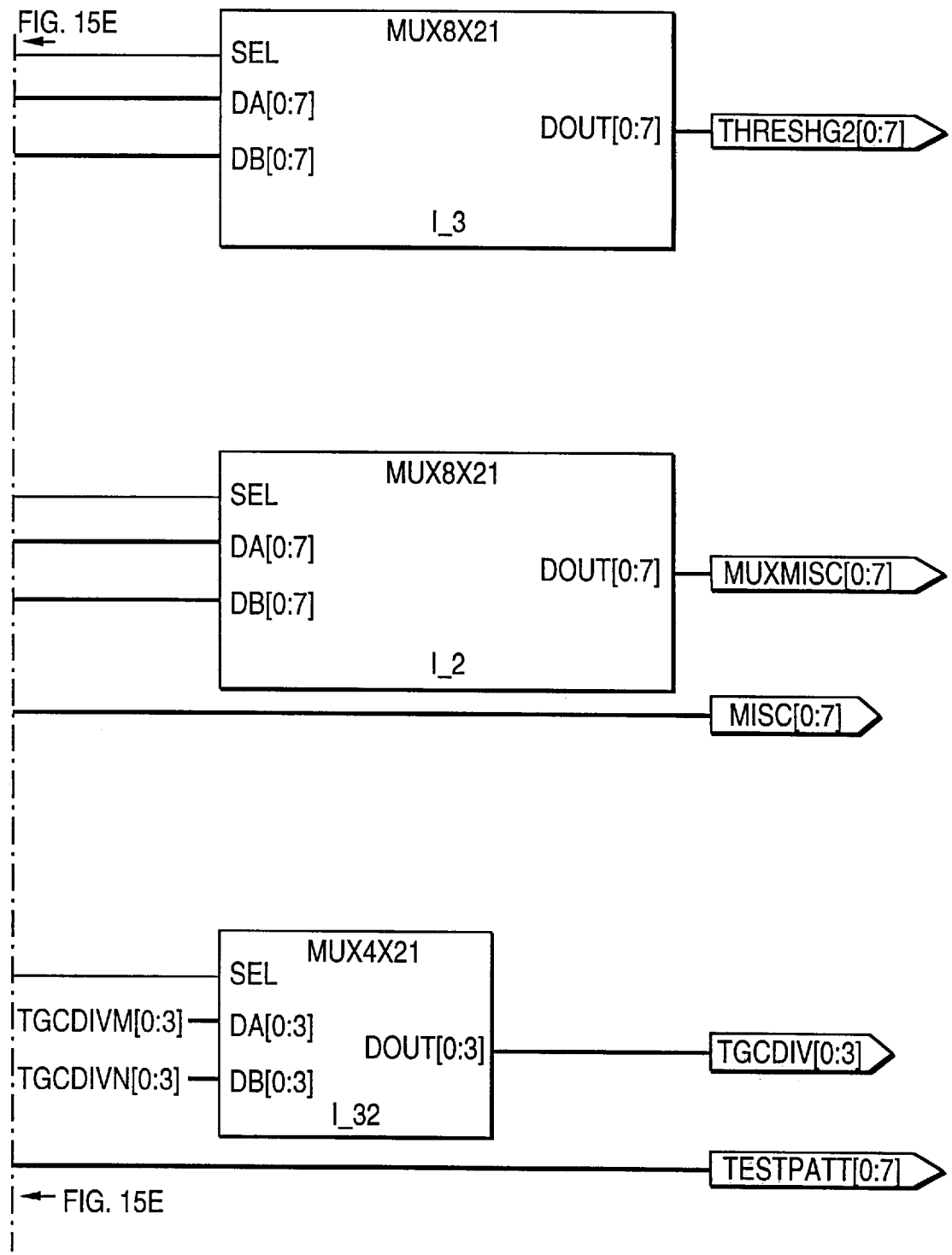

The ultrasonic testing system 10 can also operate in an interface gate mode in which a flaw gate search and/or waveform store process is delayed until the received ultrasonic transducer signal exceeds a user-selectable threshold during a user-selectable search time interval. With reference to FIG. 9, the comparator/time-of-flight circuit COMPTOF 95 used for flaw gate 1 is also used for the interface gate function. An interface gate search interval is defined as the first of two G1ACT intervals, which is signaled by an INTERFACEACT signal being equal to 1. The INTERFACEACT signal is generated by the MODE circuit 97. A unique threshold is available for the interface gate which is selected by a multiplexer 151 shown in FIG. 15, which is found within an ISAOUT circuit 140 shown in FIG. 14. The multiplexer 151 selects the unique threshold based on the INTERFACEACT signal being equal to 1. When the ultrasonic testing system 10 is placed in the interface gate mode, the timer FPGA 33 is also placed in an interface gate mode causing the timer FPGA 33 to end the first interface gate search interval G1ACT as soon as the first stored time-of-flight pulse STOF is received. This transition of the interface gate interval GIACT is caused by an ENDIGATEx signal, which is generated by the time-of-flight (TOF) circuit 120, shown in FIG. 13.

The ultrasonic testing system 10 may be placed in the interface gate mode in many different applications. For instance, in a water tank scan of a submerged part with a variable-height surface, the ending of an interface gate search interval after a threshold crossing can be used to delay storage of waveform data until after the ultrasound has passed through the water and struck the front interface of the part. Thus, the unnecessary storage of data for the water path may be avoided by placing the ultrasonic testing system 10 in the interface gate mode. The recorded interface gate time-of-flight (TOF) can also be used to map the surface height of the part.

Figure 16B:
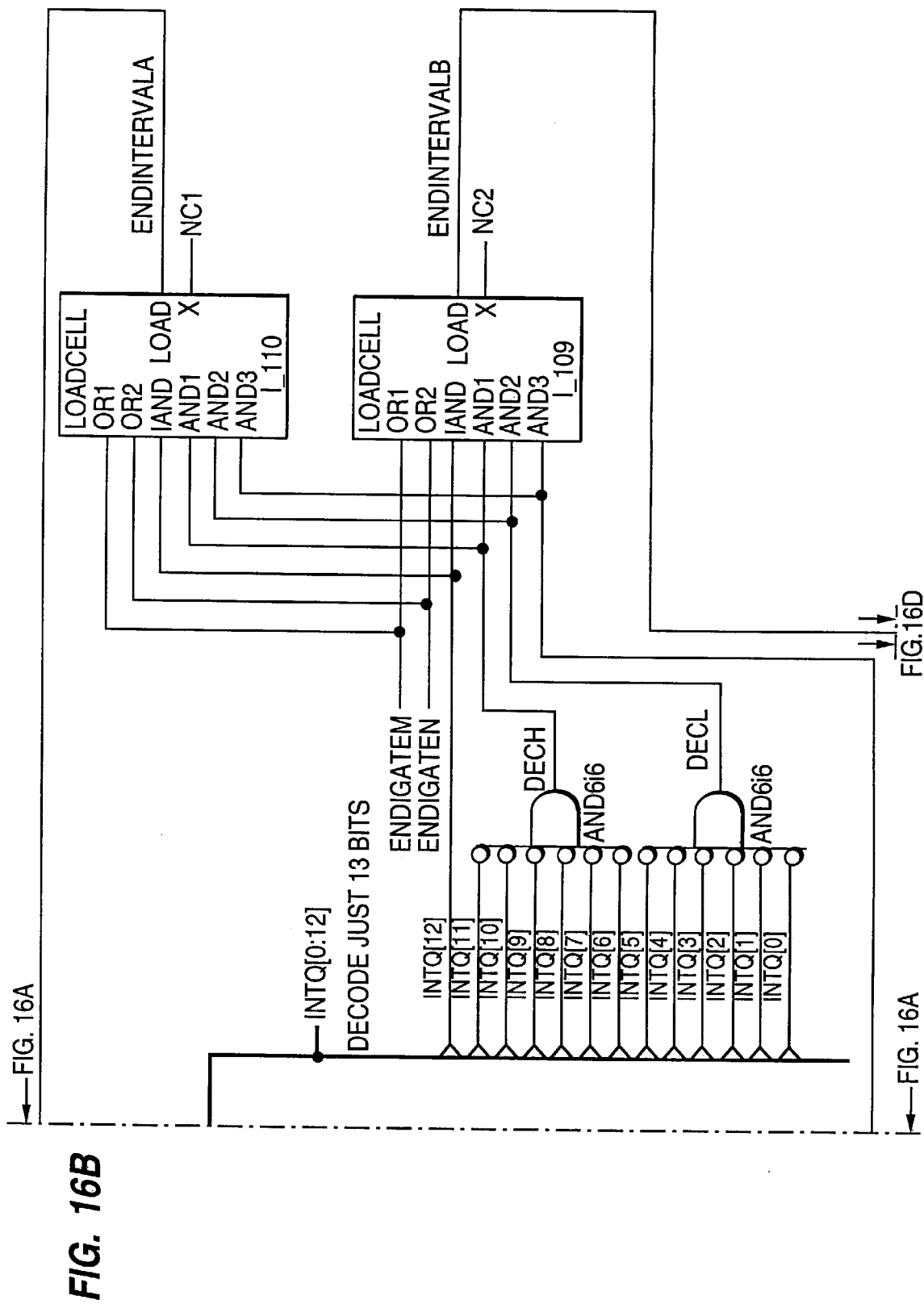
FIG. 16 (comprising FIGS. 16A, 16B, 16C and 16D) is a block diagram of an EVENCNT circuit shown in FIG. 12.
Figure 16C:
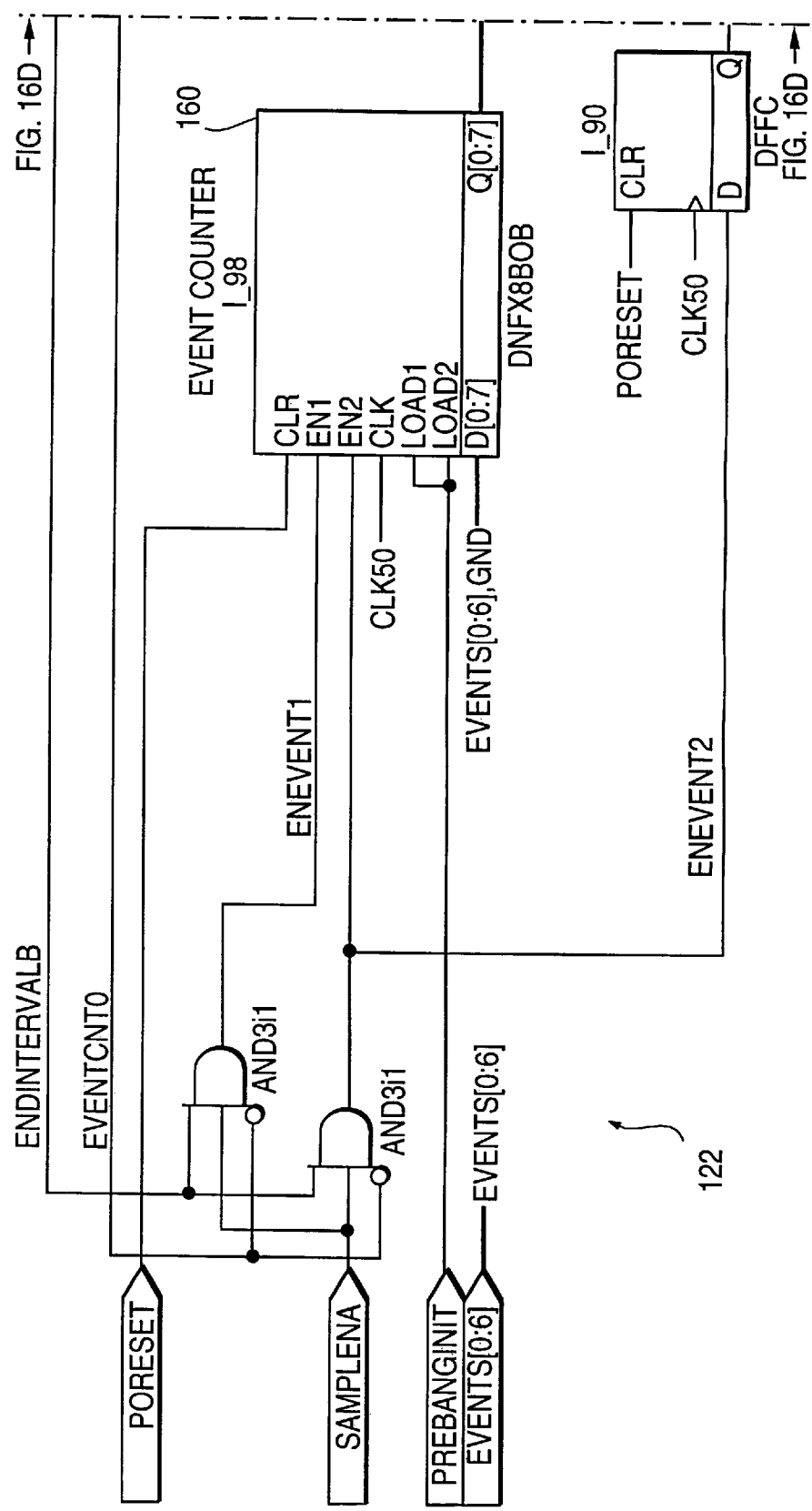

As discussed above, the timer FPGA 33 is used in conjunction with the two 8K by 8-bit SRAM's 35 and 36 to define a waveform acquisition interval and a hardware gate search interval. With reference to FIG. 16, which shows the EVENTCNT circuit 122, an 8-bit counter 160 counts down through event states or interval numbers and, in general, provides an address for the interval mode static RAM's 35 and 36. A thirteen-bit counter 161 maintains the event counter 160 in each state for the desired amount of time. More specifically, when the output INTQ(0:12) of the counter 161 is equal to 0, the event counter 160 is enabled. The static RAM's 35 and 36 have 13 bits for storing interval length which are loaded into the interval timer 161 at the beginning of each interval. The static RAM's 35 and 36 also have bits for arbitrarily programming the ultrasonic testing system 10 in one of eight modes, corresponding to the possible combinations of a waveform store enable WAVEEN, a gate 1 enable G1EN, and a gate 2 enable G2EN. These three bits of the static RAM's 35 and 36 define waveform acquisition intervals and hardware gate search intervals for the comparator FPGA 32 and for the wave FPGA 33. Inactive delay intervals are defined by programming events in intervals for which some or all of the WAVEEN, G1EN, and G2EN signal lines are inactive.

In operation, prior to the main bang, the static RAM's 35 and 36 must be loaded with the appropriate interval counts in bits 3 to 15 and the appropriate corresponding gate modes in bits 0 to 2. Just prior to each main bang, the event counter 160 and interval timer 161 are loaded with the initial count EVENTS(0:6) and the initial interval INTERVAL(0:12) by reset signals PREBANGRS and PREBANGINIT. As soon as the sample enable SAMPLEN signal goes active, the event counter 160 decrements its count and the interval timer 161 begins counting down. When the interval timer 161 reaches 0, the present value of the INTERVAL(0:12) is loaded into the interval timer 161 from the static RAM's 35 and 36 and the event counter 160 decrements thereby producing a new address for the static RAM's 35 and 36. This process continues until both counters 160 and 161 reach 0 at which time both counters 160 and 161 stop. The gate intervals are defined by the logic levels appearing at the SRAM's 35 and 36 outputs (0:2) during the countdown of the counters 160 and 161.

As stated above, the three bits (0:2) of the SRAM are used to place the ultrasonic testing system 10 in one of eight modes. More specifically, bit 0 is set high to enable waveform storage and is set low to disable waveform storage. To enable a hardware gate 1 search, bit 1 is set high and is set low to disable a hardware gate 1 search. The remaining bit, namely bit 2, is set high to enable a hardware gate 2 search and is set low to disable a hardware gate 2 search. These mode bits (0:2) are concatenated to the interval bits (3:12) corresponding to the following interval.

In order to minimize logic gate count and propagation delay, the event counter output bits are connected to the input of an OCTAL OR gate, whose second inputs are connected to the complement of the ISA interface IMSRAM address register. As a result, the address register must be set to FFh during the exam and the EVENT counter 160 must be reset by the CPU 9.

An example of the programming for the SRAM's 35 and 36 is based on the following conditions: FS=50 MS/s, interface gate enabled, search interval delay=3 us, width=4 us, waveform gate interval having a delay=1 us, a width=10 us, a hardware gate 1 search interval having a delay=3 us, width=3 us, and a hardware gate 2 search interval disabled. The waveform and hardware GATE1 events are referenced to the end of the interface gate. The contents for the ISA address event SRAM are as follows:

TABLE 1

| ISA ADDRESS | EVENT | HEX | INTERVAL, BIN | DEC. | MODE, BIN | MODE |
|---|---|---|---|---|---|---|
| F8h | 7 | 4A8h | 0000010010101 | 149 | 000 | dummy startup |
| F9h | 6 | 638h | 0000011000111 | 199 | 000 | inter. delay |
| FAh | 5 | 152h | 0000000101010 | 42 | 010 | inter. search |
| FBh | 4 | 350h | 0000001101010 | 106 | 000 | a-gate delay |
| FCh | 3 | 4A9h | 0000010010101 | 149 | 001 | a-gate active |
| FDh | 2 | 7CBh | 0000011111001 | 249 | 011 | a-gate, h.w. gate |
| FEh | 1 | 51h | 0000000001010 | 10 | 001 | a-gate active |
| FFh | 0 | 0h | 0000000000000 | 0 | 000 | wind-down |

Thus, the ultrasonic testing system 10 can generate multiple gate intervals wherein these intervals may be concatenated or, alternatively, may be disjoint. The number of gates may be expanded by one gate per bit width of timer memory. For higher number of gates, much more power and logic would be consumed with the conventional arrangement of one delay timer and one width timer per gate.

Figure 17A:
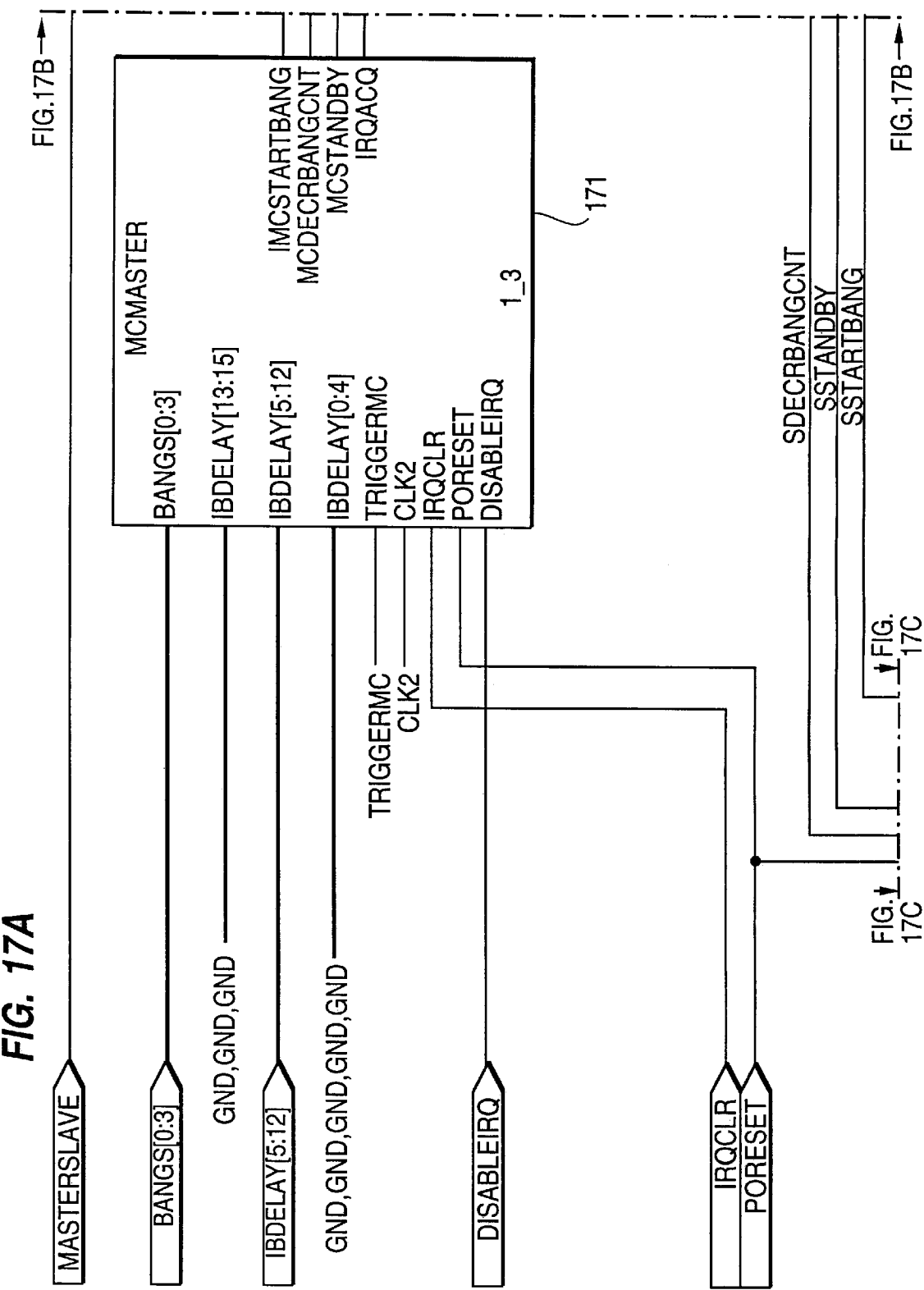
FIG. 17 (comprising FIGS. 17A, 17B, 17C and 17D) is a block diagram of an MC circuit shown in FIG. 11.
Figure 17B:
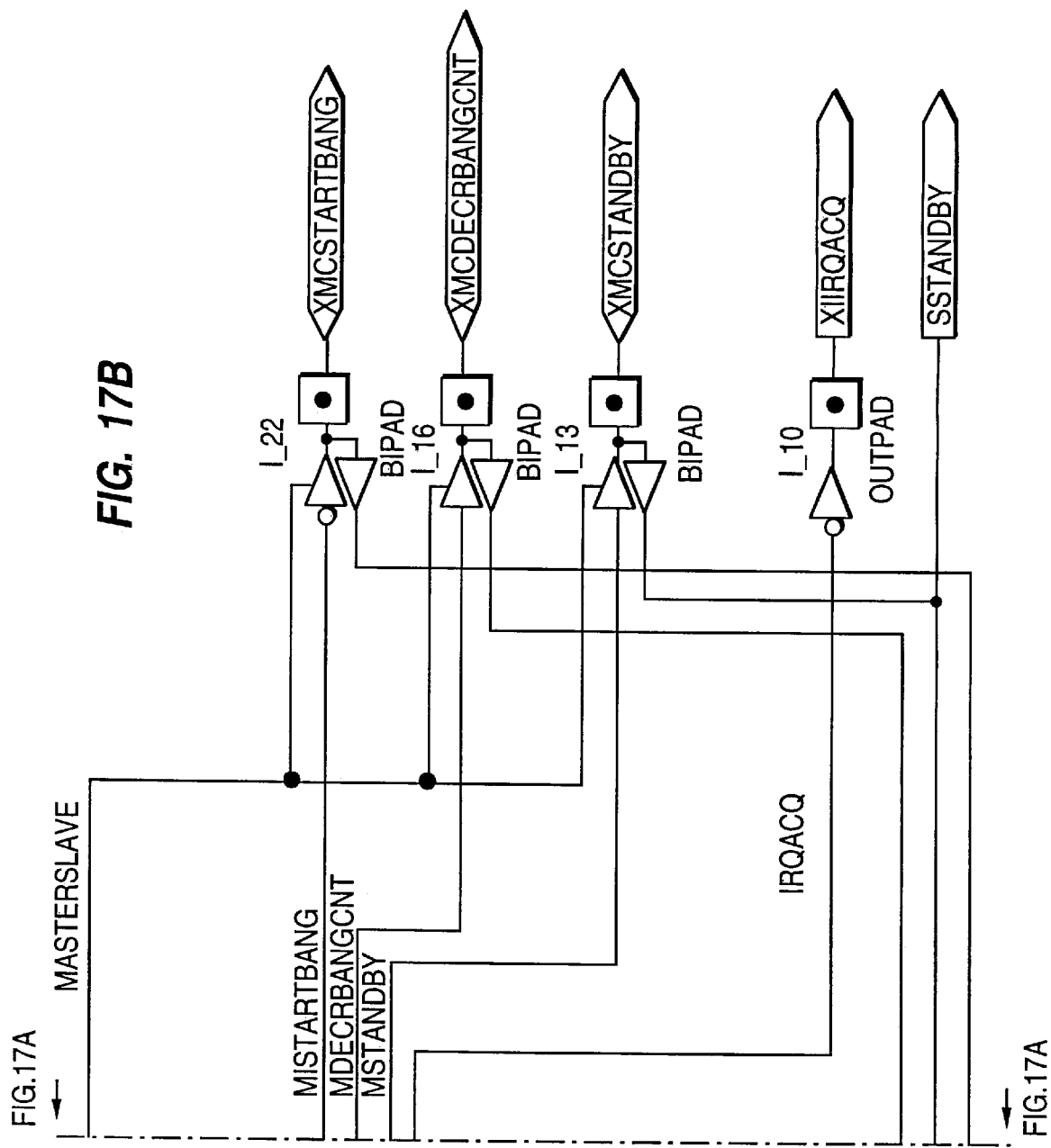
Figure 17D:
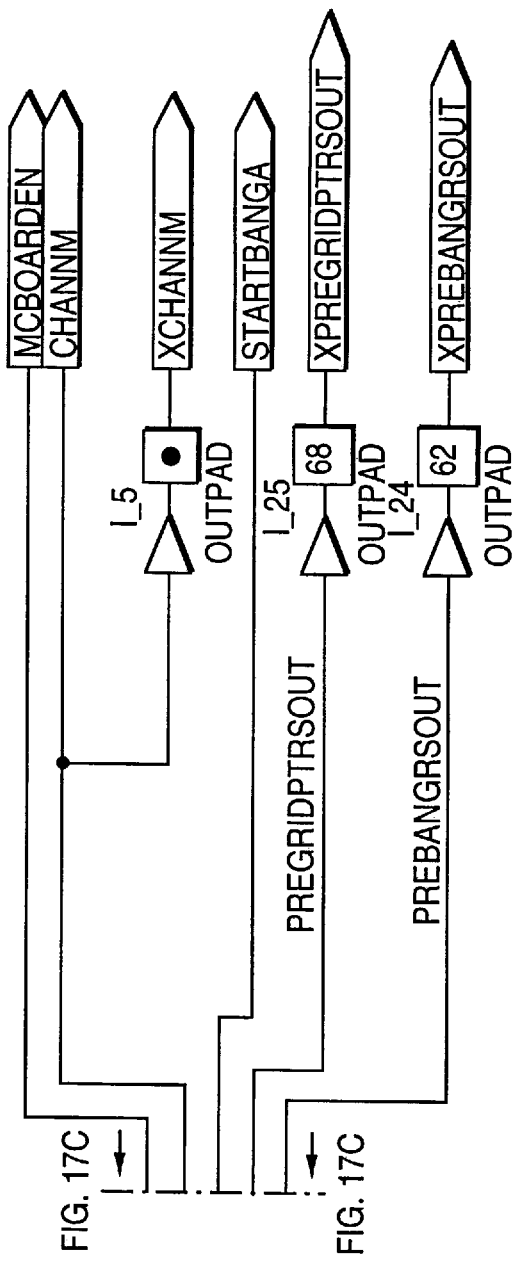
Figure 18B:
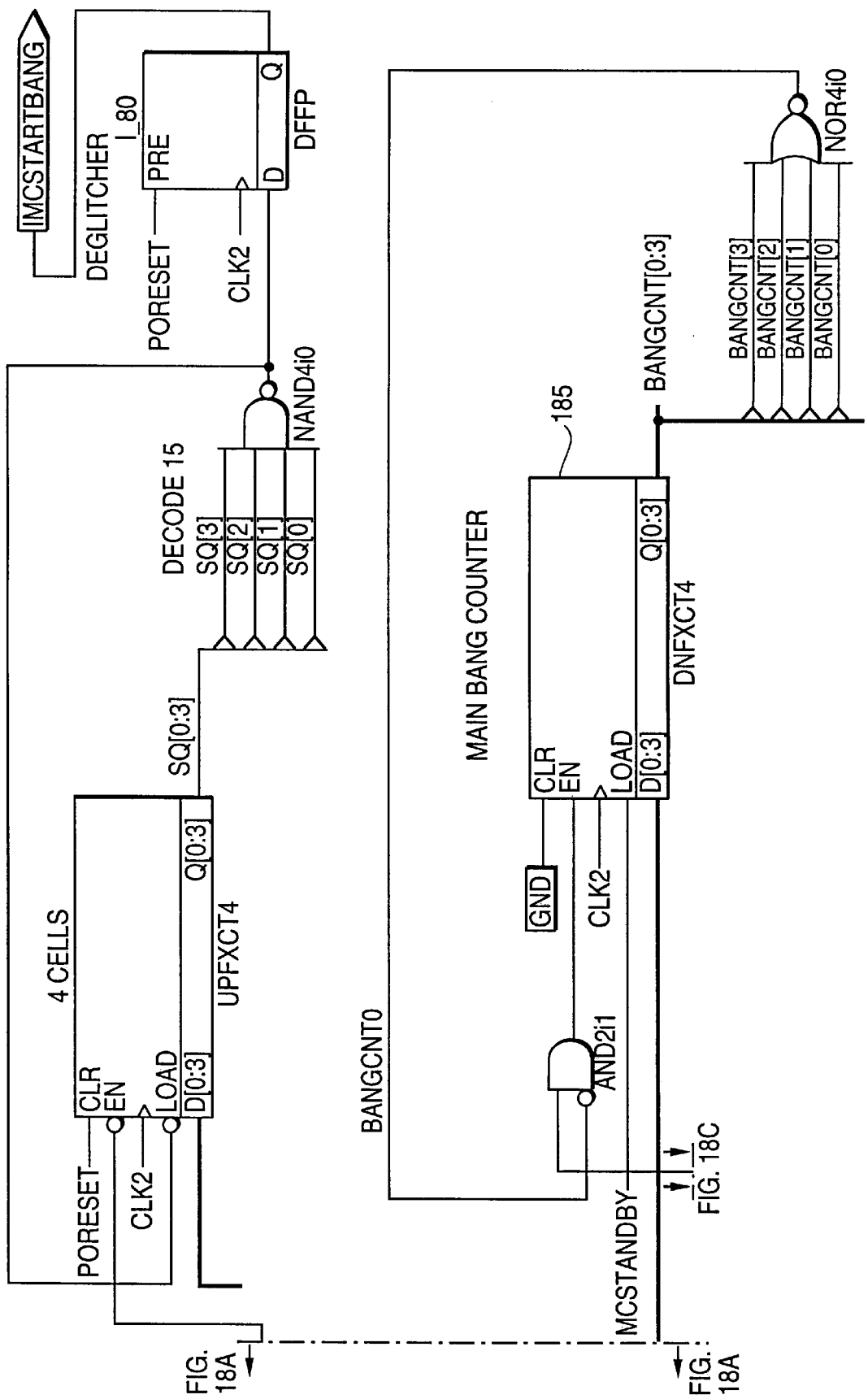
FIG. 18 (comprising FIGS. 18A, 18B, 18C, 18D, 18E and 18F) is a block diagram of an MCMASTER circuit shown in FIG. 17.
Figure 18C:
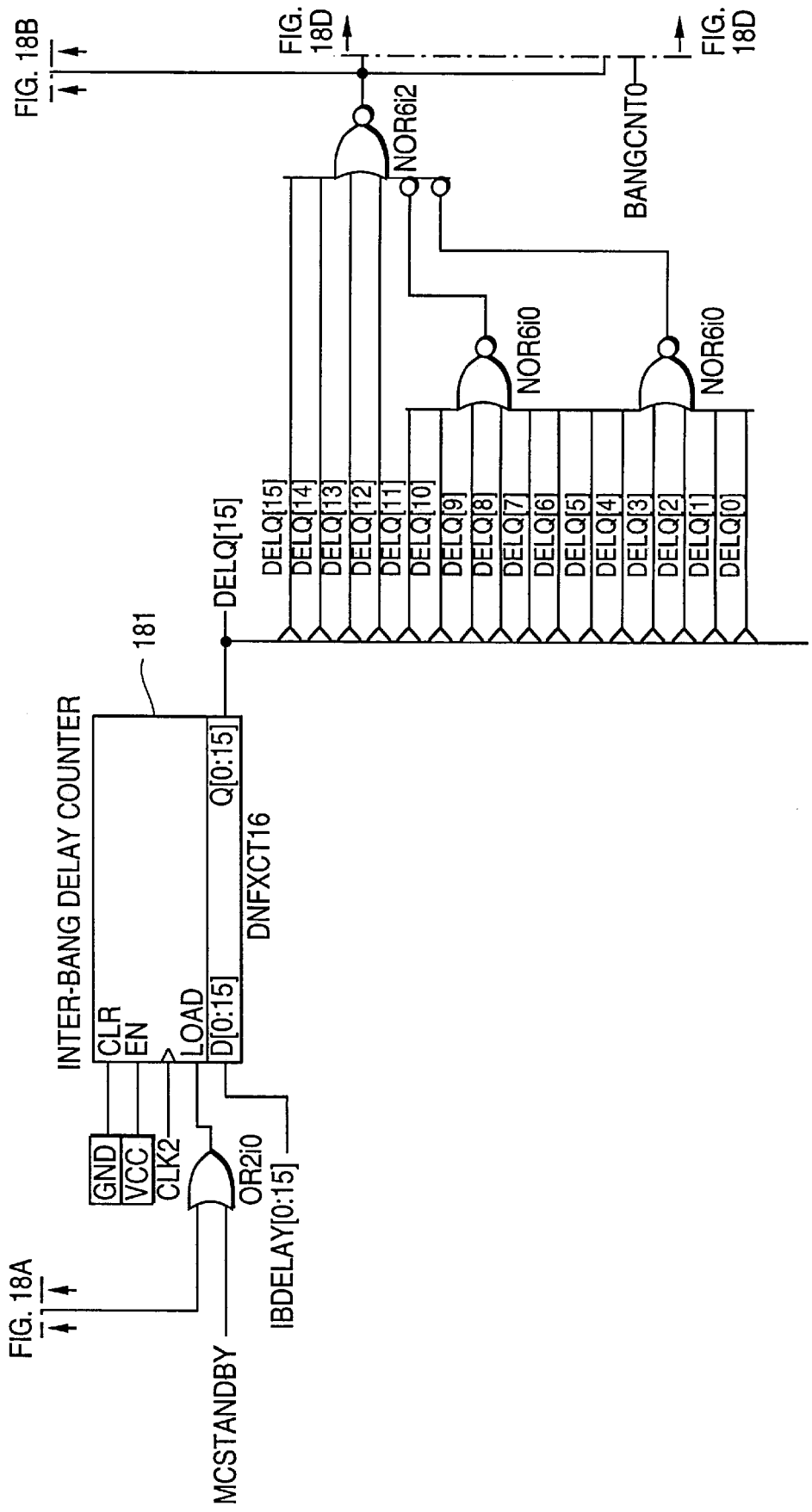
Figure 18D:
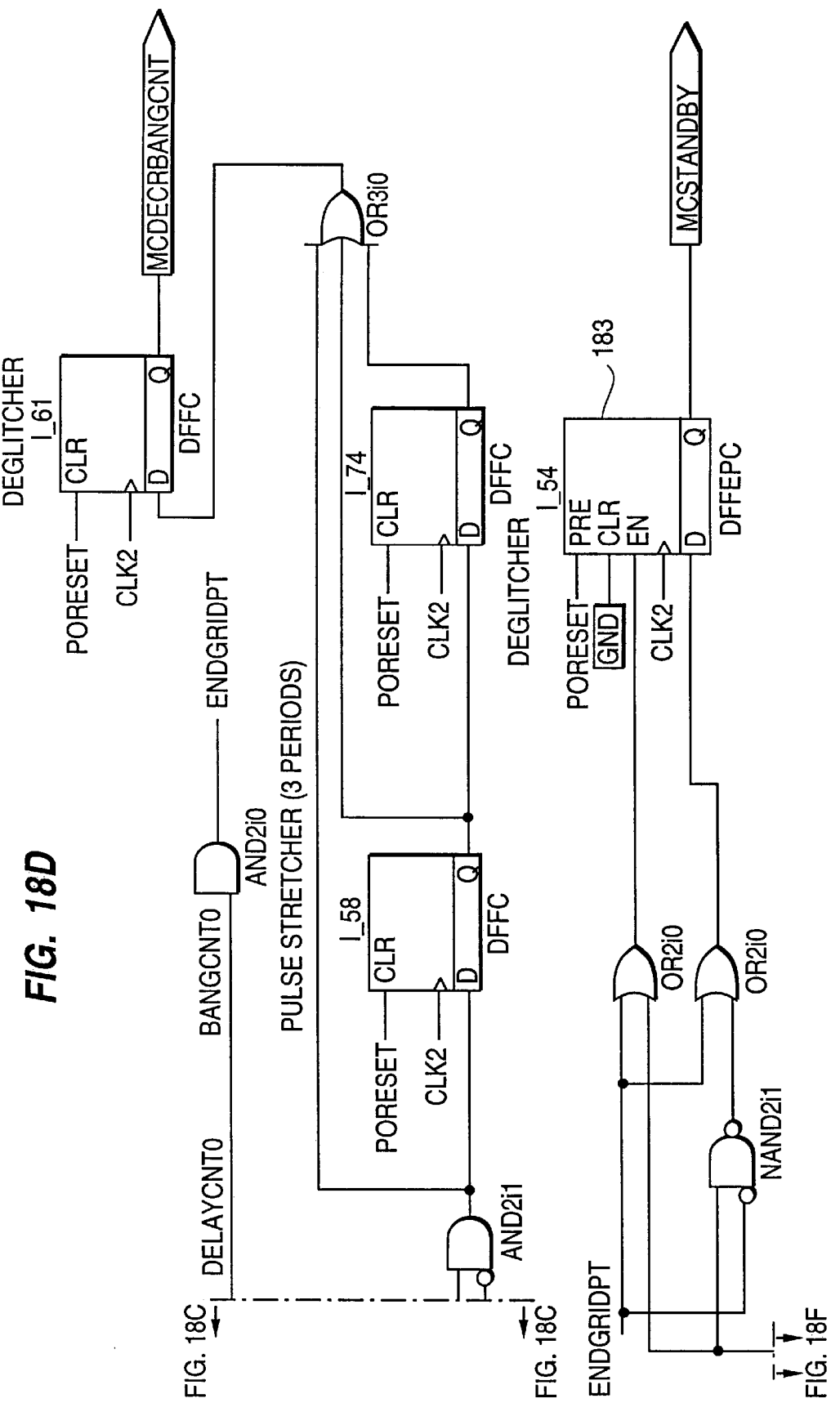
Figure 18E:
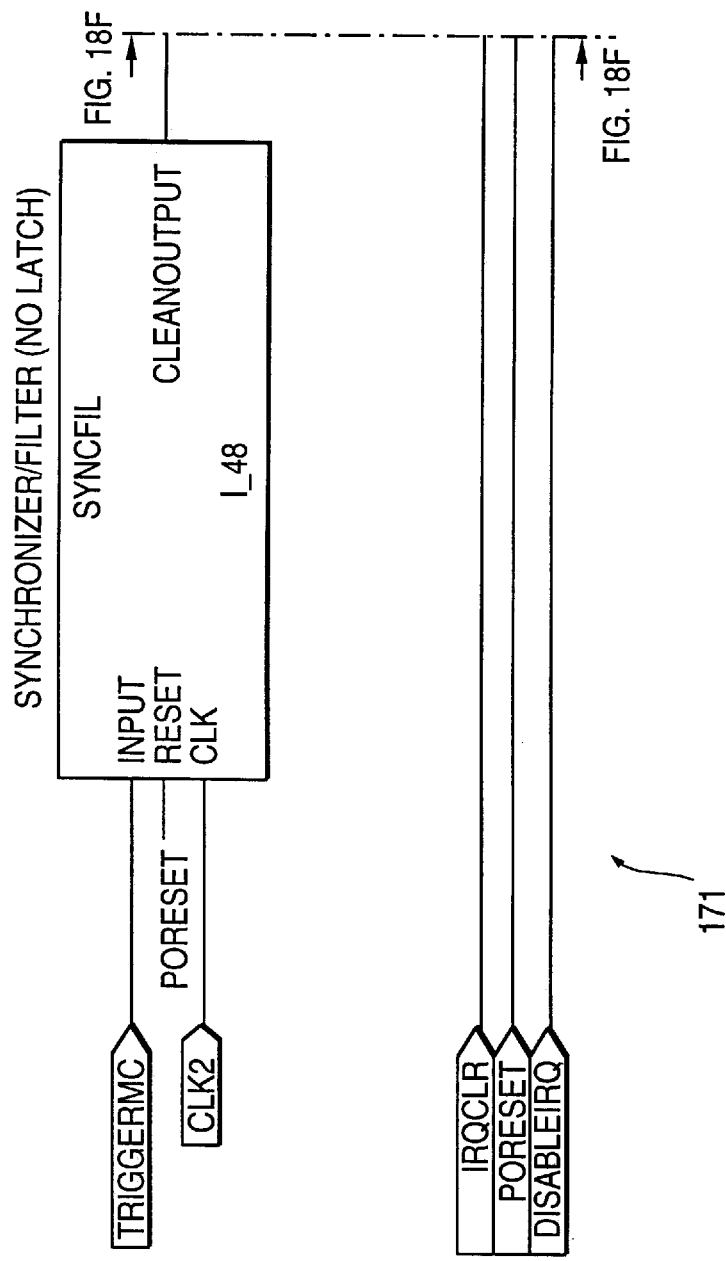
Figure 18F:
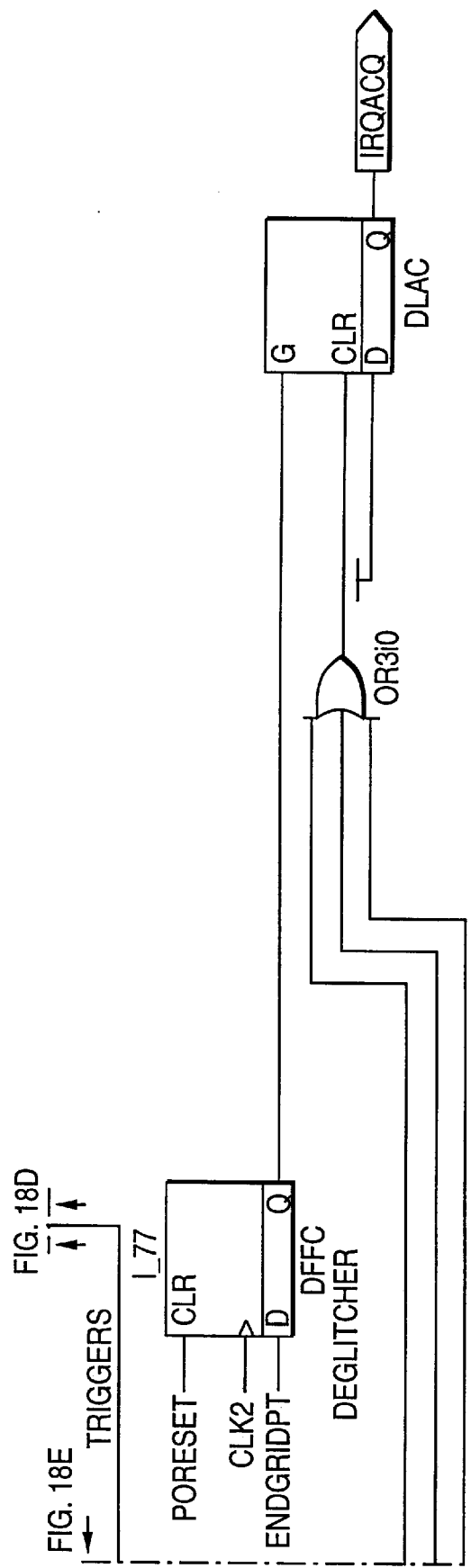

The ultrasonic testing system 10 has a multi-channel (MC) control bus, which is a three signal bus passing through a multi-channel buffer circuit 37 to the timer FPGA 33. The multi-channel control bus is connected to each UT System Board in the ultrasonic testing system. The multi-channel control logic resides in the timer FPGA 33. FIG. 17 is a block diagram of an MC circuit 111 shown in FIG. 11 while FIGS. 18 and 19 respectively illustrate an MCMASTER circuit 171 and an MCSLAVE circuit 172 shown in FIG. 17.

Figure 19B:
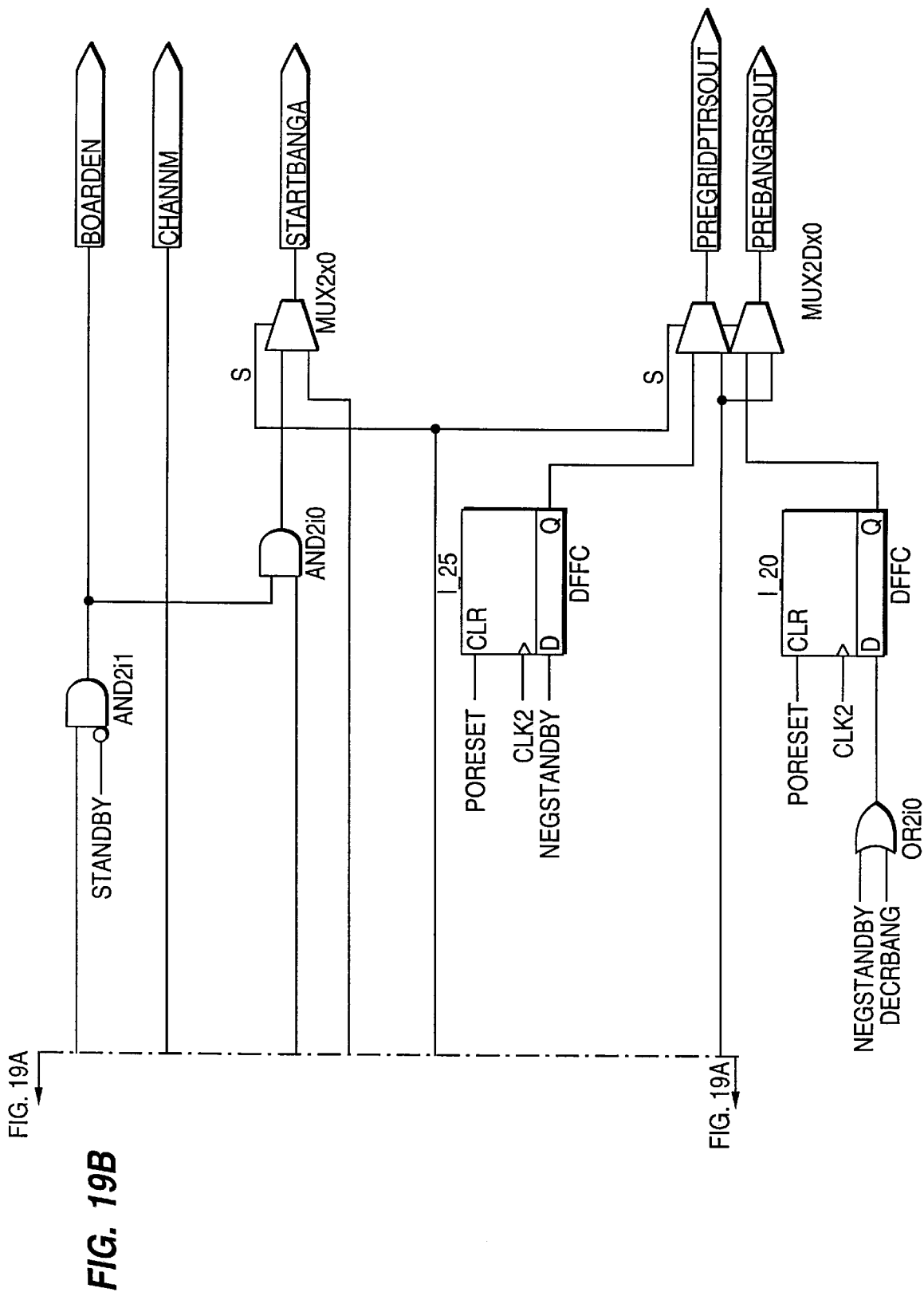
FIG. 19 (comprising FIGS. 19A, 19B, 19C and 19D) is a block diagram of an MCSLAVE circuit shown in FIG. 17.
Figure 19C:
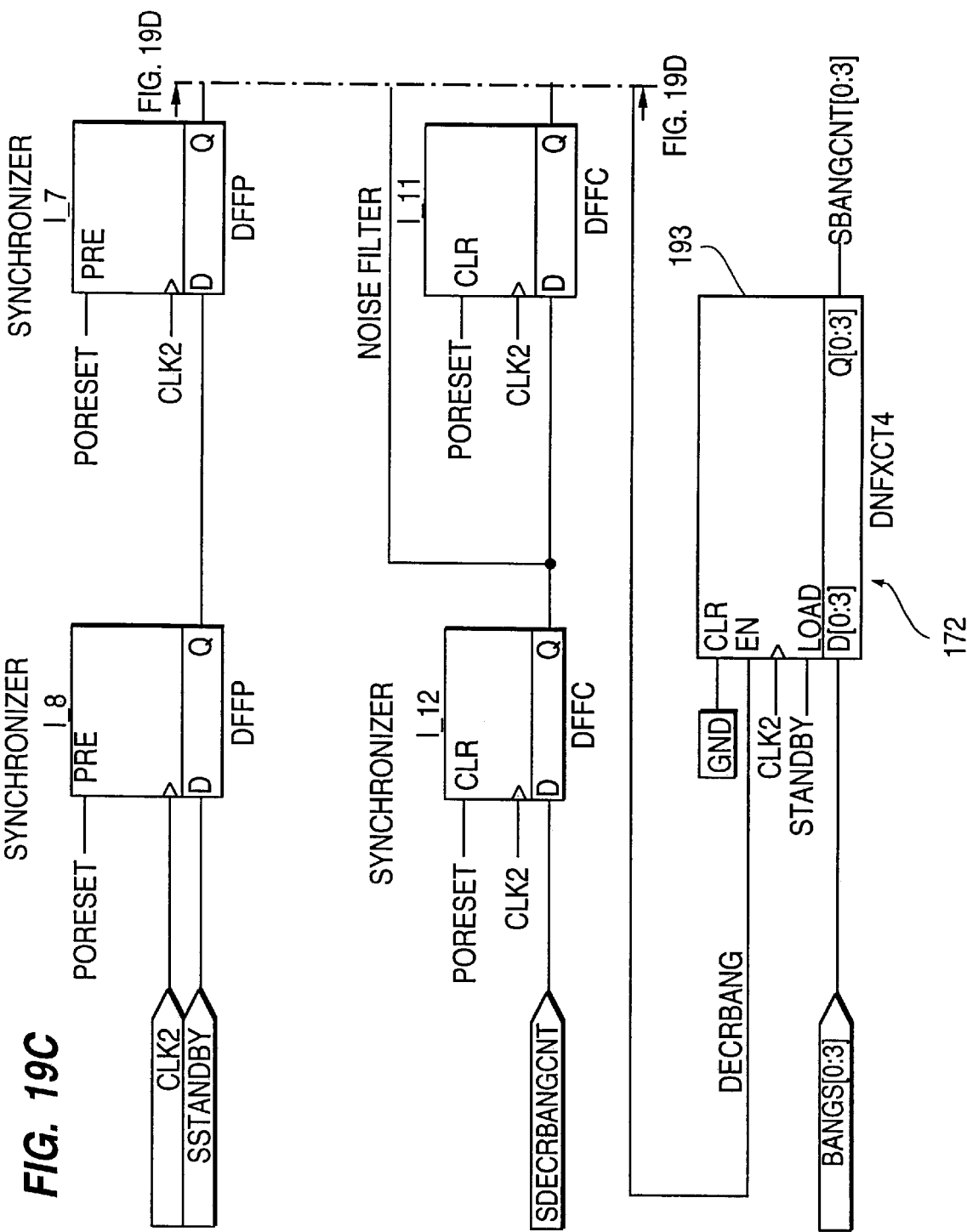
Figure 19D:
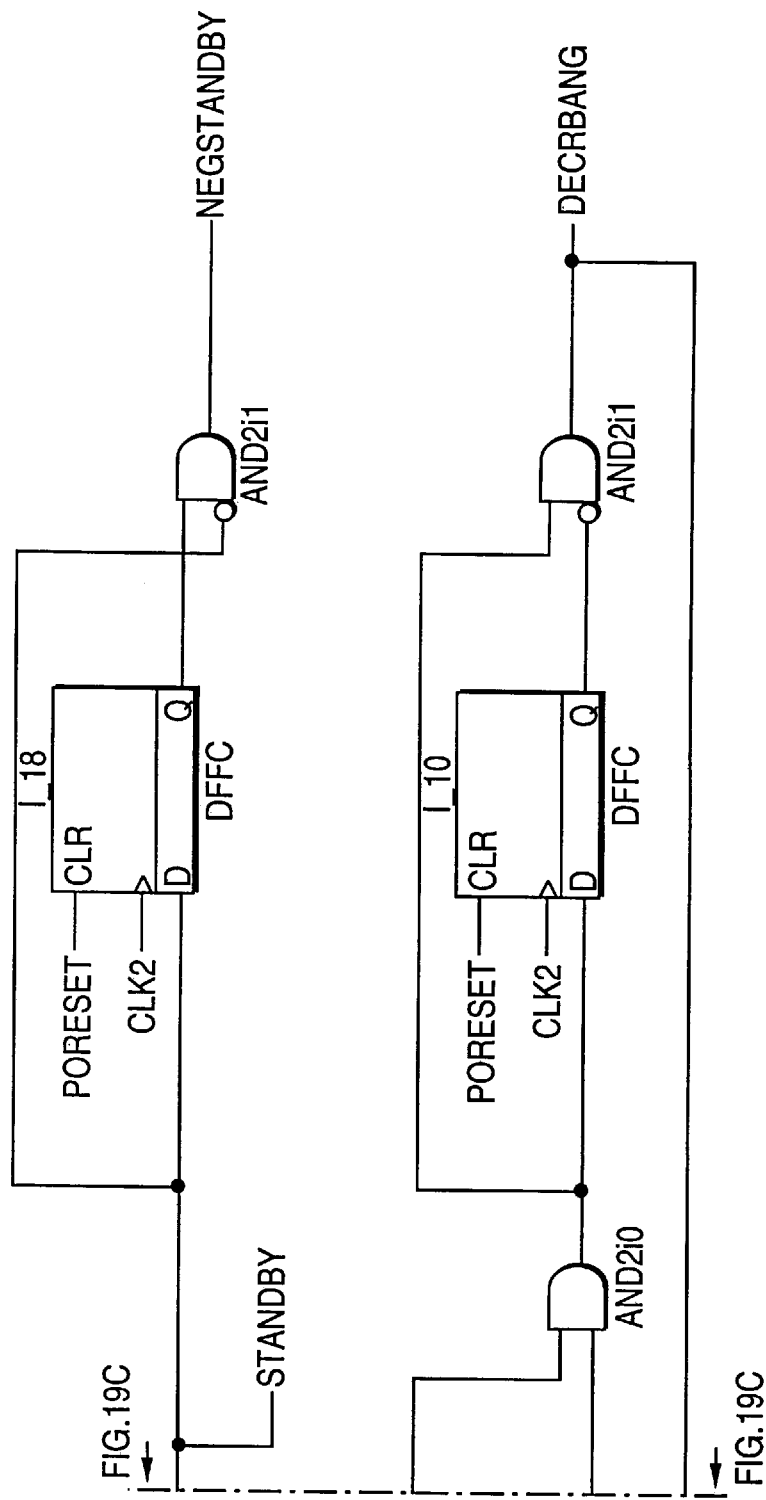

With reference to FIGS. 17 to 19, only one board out of multiple boards in the ultrasonic testing system 10 is initialized by the CPU 9 to be an active multi-channel master, or simply master, and only the master 171 drives the multi-channel control bus and the computer bus Interrupt Request (IRQ) line. However, all of the boards have active multi-channel slaves 172. The three lines comprising the multi-channel control bus are an MCSTANDBY signal line, an MCDECBANGCNT signal line, and an MCSTARTBANG signal line, which are effectively connected from the master 171 to each slave 172. The master 171 manipulates these lines to make a so-called "slave bang counter" 193 on each board count down. Each slave 172 on the various boards compares the current bang count to it's own bang assignment to decide whether to acquire data during the current bang. As defined above, the bang is the high-voltage pulse which causes the initial output pulse of ultrasonic energy from the transducer 7.

More specifically, in operation during power-on, the CPU 9 automatically initializes all boards to be slaves 172. The CPU 9 next initializes only one of the boards to be the master 172 and programs the number of bangs per grid crossing BANGS(0:3) as well as the time between bangs IBANGDELAY(5:12). Each slave 172 is initialized by the CPU 9 with the number of bangs per grid crossing BANGS (0:3) and their bang assignments BASSIGNMENT(0:3). When the master 171 is triggered by a trigger multi-channel control signal TRIGGERMC having a value of 1, the master 171 drops the MCSTANDBY signal line to 0, which initializes the slave bang counters 193, and issues an MCSTARTBANG pulse. As shown in FIG. 19, the slaves 172 have circuits 191 and 192 for determining whether their bang assignment BASSIGNMENT matches the current bang count BANGCNT and, if it does, will generate a board enable signal BOARDEN to start acquisition. An inter-bang delay counter 181 in the master 171 will begin to count down and, when it reaches 0, a decrement bang count pulse MCDECBANGCNT will be issued. This pulse MCDECBANGCNT causes a master bang counter 185 and all slave bang counters 193 to decrement their bang count. At seven microseconds later, another start bang pulse MCSTARTBANG is issued by the master 171. This process continues until the bang count BANGCNT is reduced to 0 and the inter-bang delay count is 0, at which time an interrupt IRQACQ is issued, an output of flip flop 183 causes the signal line MCSTANDBY to go high, and the control by the master 171 is inhibited. Each channel in the ultrasonic testing system 10 can be programmed to selectively fire its pulser in pulser or preamp circuits 12 or 14 during acquisition. Therefore, multiple channels may be programmed to fire simultaneously, if desired. Multiple boards 10 can be programmed to acquire data simultaneously in close synchronization to each other.

The multi-channel controller 111 is fast, flexible, and expandable and uses only one interrupt per grid crossing by the acquisition system, regardless of the number of channels, which thereby reduces computer bus overhead. In the preferred embodiment, up to 8 boards and 16 channels may be used, with each board multiplexing 2 analog channels to one A-to-D circuit 18. The ultrasonic testing system 10 according to the invention allows simultaneous waveform and/or hardware gate acquisition of data on as many channels as there are boards. The invention therefore avoids the disadvantage of the prior art which required multiple bangs and their associated ring-down time in a time-multiplexed system. Also, by simultaneously feeding one analog signal to a dual A/D converter 21 when the highest sample rate is selected, parallel processing of two half-speed data streams is allowed, which thereby enables waveform and hardware gate processing to be done at a high speed using CMOS logic technology.

An ultrasonic testing system according to the invention provides a number of advantages over existing testing systems. For instance, the ultrasonic testing system provides a fast recovery, signed digital hardware video rectifier and filter which is capable of compressing data in received ultrasonic transducer signals by a fixed ratio of up to 16:1 or more. The rectifier and filter stores the value of the highest-amplitude sample in a group of samples and recovers faster than conventional analog versions. An ultrasonic testing system also provides a higher resolution rectifier and filter which is capable of preserving the exact time-of-flight by adding one byte of timing information per waveform sample.

An ultrasonic testing system according to the invention is also operable as a hardware digital threshold-based run-length encoder for compressing data in received ultrasonic transducer signals and for storing only that data whose amplitude exceeds a user-selectable threshold. The threshold-based run-length encoding is enhanced by storing a user-selectable number of data points both before and after the below-to-above and above-to-below threshold crossings, respectively. An ultrasonic testing system may further combine the threshold-based run-length encoding with the signed digital hardware video rectifier and filter to achieve very high waveform compression ratios.

An ultrasonic testing system according to the invention provides the capability for a number of digital hardware gates. For instance, an ultrasonic testing system can search a received ultrasonic transducer signal and store the peak amplitude and polarity and the time-of-flight corresponding to that peak for a user-defined search interval. Also, a threshold flaw gate may be provided for searching an ultrasound-derived signal and storing the time-of-flight corresponding to the first excursion of the signal through a user-selected threshold for a user-defined search interval. As another example, an interface gate can be provided for delaying the normal flaw gate search and waveform store process until the received ultrasonic transducer signal exceeds a user-selectable threshold for a user-selectable search time interval.

An ultrasonic testing system according to the invention also provides for compact logic control of three gates with only two counters. The intervals may be concatenated and can be expanded by one gate per bit width of timer memory. The invention provides for higher numbers of gates with less power and logic than that required for a conventional arrangement of one delay timer and one width timer per gate.

An ultrasonic testing system according to the invention also provides a fast, flexible, and expandable multi-channel controller which uses only one interrupt per grid crossing by acquisition system regardless of the number of channels. Further, as stated above, a multi-channel testing system permits simultaneous waveform and/or hardware gate acquisition of data on numerous channels and has parallel processing of two data streams.

The foregoing description of the preferred embodiment of the invention has been presented for purposes of illustration and description. It is not intended to be exhaustive or to limit the invention to the precise form disclosed. Many modifications and variations are possible in light of the above teaching.

The embodiment was chosen and described in order to best explain the principles of the invention and its practical application to thereby enable others skilled in the art to best utilize the invention and various embodiments and with various modifications as are suited to the particular use contemplated. It is intended that the scope of the invention only be limited by the claims appended hereto.

What is claimed is:

1. An ultrasonic testing system for compressing digital data, comprising:

a pulsing circuit for stimulating an ultrasonic transducer with a voltage signal and for receiving an analog data signal from said transducer;

a timing circuit for defining acquisition intervals;

an analog-to-digital converter for converting said analog data signal into digital data at said acquisition intervals;

a counter circuit for defining user-selected groups of digital data samples;

a peak detector circuit for acquiring a peak value of said digital data within each of said groups of digital data samples; and a memory for storing only the peak values of said digital data one from each of said groups of digital data samples, whereby said digital data is compressed to said peak values.

2. The ultrasonic testing system as set forth in claim 1, wherein said digital data is compressed by an integer ratio of 16:1.

3. The ultrasonic testing system as set forth in claim 1, wherein said digital data is compressed by an integer ratio not less than 2:1.

4. The ultrasonic testing system as set forth in claim 1, further comprising a second pulsing circuit for stimulating a second ultrasonic transducer with a second voltage signal and for receiving a second analog data signal from said transducer and wherein said analog-to-digital converter converts said second analog signal into second digital data and said peak detector circuit determines the peak values out of said digital data and said second digital data.

5. The ultrasonic testing system as set forth in claim 1, further comprising a control circuit for preventing said memory from storing the peak values until said digital data exceeds a threshold value during a preceding predetermined search interval.

6. An ultrasonic testing system for compressing digital data, comprising:

a pulsing circuit for stimulating an ultrasonic transducer with a voltage signal and for receiving an analog data signal from said transducer;

a timing circuit for defining acquisition intervals;

an analog-to-digital converter for converting said analog data signal into digital data at said acquisition intervals;

a counter circuit for defining user-selected groups of digital data samples;

a peak detector circuit for acquiring a peak value of said digital data within each of said groups of digital data samples; and a memory for storing only the peak values of said digital data one from each of said groups of digital data samples, whereby said digital data is compressed to said peak values;

wherein said peak detector circuit acquires said peak value only during positive values of said analog data signal so as to result in half-wave rectification of said analog data signal.

7. An ultrasonic testing system for compressing digital data, comprising:

a pulsing circuit for stimulating an ultrasonic transducer with a voltage signal and for receiving an analog data signal from said transducer;

a timing circuit for defining acquisition intervals;

an analog-to-digital converter for converting said analog data signal into digital data at said acquisition intervals;

a counter circuit for defining user-selected groups of digital data samples;

a peak detector circuit for acquiring a peak value of said digital data within each of said groups of digital data samples; and a memory for storing only the peak values of said digital data one from each of said groups of digital data samples, whereby said digital data is compressed to said peak values;

wherein said peak detector circuit acquires said peak value only during negative values of said analog data signal so as to result in half-wave rectification of said analog data signal.

8. An ultrasonic testing system for compressing digital data, comprising:

a pulsing circuit for stimulating an ultrasonic transducer with a voltage signal and for receiving an analog data signal from said transducer;

a timing circuit for defining acquisition intervals;

an analog-to-digital converter for converting said analog data signal into digital data at said acquisition intervals;

a counter circuit for defining user-selected groups of digital data samples;

a peak detector circuit for acquiring a peak value of said digital data within each of said groups of digital data samples; and a memory for storing only the peak values of said digital data one from each of said groups of digital data samples, whereby said digital data is compressed to said peak values;

wherein said peak detector circuit acquires said peak value during both positive and negative values of said analog data signal so as to result in full-wave rectification of said analog data signal.

9. An ultrasonic testing system for compressing digital data, comprising:

a pulsing circuit for stimulating an ultrasonic transducer with a voltage signal and for receiving an analog data signal from said transducer;

an analog-to-digital converter for converting said analog data signal into digital data;

a threshold compare circuit for determining whether said digital data exceeds a user-selected threshold; and a memory for storing the digital data that exceeds said user-selected threshold.

10. An ultrasonic testing system for compressing digital data, comprising:

a pulsing circuit for stimulating an ultrasonic transducer with a voltage signal and for receiving an analog data signal from said transducer;

an analog-to-digital converter for converting said analog data signal into digital data;

a threshold compare circuit for determining whether said digital data exceeds a user-selected threshold; and a memory for storing the digital data that exceeds said user-selected threshold;

wherein said memory stores digital data both before and after the data exceeding the user-selected threshold.

11. The ultrasonic testing system as set forth in claim 9, wherein said threshold compare circuit determines whether said digital data exceeds the user-selected threshold during a user-selected interval.

12. An ultrasonic testing system for compressing digital data, comprising:

a pulsing circuit for stimulating an ultrasonic transducer with a voltage signal and for receiving an analog data signal from said transducer;

an analog-to-digital converter for converting said analog data signal into digital data;

a threshold compare circuit for determining whether said digital data exceeds a user-selected threshold; and a memory for storing the digital data that exceeds said user-selected threshold wherein said threshold compare circuit determines whether said digital data exceeds the user-selected threshold during a user-selected interval and wherein said threshold compare circuit determines whether said digital data exceeds the user-selected threshold for a plurality of user-selected intervals.

13. The ultrasonic testing system as set forth in claim 9, further comprising a control circuit for preventing said memory from storing the digital data until said digital data exceeds a second threshold value during a preceding predetermined search interval.

14. The ultrasonic testing system as set forth in claim 9, further comprising a second pulsing circuit for stimulating a second ultrasonic transducer with a second voltage signal and for receiving a second analog data signal from said transducer and wherein said analog-to-digital converter converts said second analog signal into second digital data and said threshold compare circuit determines whether said second digital data exceeds a second user-selected threshold and said memory stores said second digital data exceeding said second user-selected threshold.

15. An ultrasonic testing system, comprising:

a pulsing circuit for stimulating an ultrasonic transducer with a voltage signal and for receiving an analog data signal from said transducer;

an analog-to-digital converter for converting said analog data signal into digital data;

a timing circuit for defining a user-selected search interval;

a peak detector circuit for acquiring a peak value of said digital data during said user-selected search interval;

a first memory for storing said peak value of said digital data;

a timer for determining a time-of-flight associated with said peak value; and a second memory for storing said time-of-flight.

16. The ultrasonic testing system as set forth in claim 15, wherein said timing circuit defines a plurality of user-selected search intervals, said peak detector acquiring peak values for said intervals, said first memory storing values of said peak values, said timer determining time-of-flights for said peak values, and said second memory storing said time-of-flights.

17. The ultrasonic testing system as set forth in claim 15, further comprising a control circuit for preventing said system from delaying and then searching for the peak value and the time-of-flight until said digital data exceeds a second threshold value during a preceding predetermined search interval.

18. The ultrasonic testing system as set forth in claim 15, further comprising a second pulsing circuit for stimulating a second ultrasonic transducer with a second voltage signal and for receiving a second analog data signal from said transducer and wherein said analog-to-digital converter converts said second analog signal into second digital data and said peak detector circuit acquires the peak value of said digital data and said second digital data.

19. An ultrasonic testing system, comprising:

a pulsing circuit for stimulating an ultrasonic transducer with a voltage signal and for receiving an analog data signal from said transducer;

an analog-to-digital converter for converting said analog data signal into digital data;

a timing circuit for defining a user-selected search interval;

a peak detector circuit for acquiring a peak value of said digital data during said user-selected search interval;

a first memory for storing said peak value of said digital data;

a timer for determining a time-of-flight associated with said peak value; and a second memory for storing said time-of-flight;

wherein said peak detector circuit further determines a polarity of the peak value and said first memory stores said polarity.

20. An ultrasonic testing system, comprising:

a pulsing circuit for stimulating an ultrasonic transducer with a voltage signal and for receiving an analog data signal from said transducer;

an analog-to-digital converter for converting said analog data signal into digital data;

a timing circuit for defining a user-selected search interval;

a comparator for determining whether said digital data exceeds a user-selected threshold during said user-selected search interval;

a timer for determining a time-of-flight associated with a first data sample that exceeds said user-selected threshold; and a memory for storing said time-of-flight.

21. The ultrasonic testing system as set forth in claim 20, further comprising a control circuit for preventing said system from delaying and then searching for a threshold crossing until said digital data exceeds a second threshold value during a preceding predetermined search interval.

22. The ultrasonic testing system as set forth in claim 20, further comprising a second pulsing circuit for stimulating a second ultrasonic transducer with a second voltage signal and for receiving a second analog data signal from said transducer and wherein said analog-to-digital converter converts said second analog signal into second digital data and comparator determines whether said second digital data exceeds a second user-selected threshold during a second user-selected interval.

23. An ultrasonic testing system, comprising:

a first pulsing circuit for stimulating a first ultrasonic transducer with a first voltage signal and for receiving a first analog data signal from said first transducer;

a second pulsing circuit for stimulating a second ultrasonic transducer with a second voltage signal and for receiving a second analog data signal from said second transducer;

analog-to-digital converting means for receiving said first and second analog data signals and for converting said first and second analog data signals into first digital data and second digital data, said analog-to-digital converting means delaying said second digital data relative to said first digital data; and means for processing said first digital data in parallel with said second digital data.

24. The ultrasonic testing system as set forth in claim 23, wherein said analog-to-digital converting means comprises a dual channel analog-to-digital converter.

25. The ultrasonic testing system as set forth in claim 23, wherein said analog-to-digital converting means comprises a single analog-to-digital converter and said system further comprises means for demultiplexing an output of said single analog-to-digital converter into said first digital data and said second digital data.

* * * * *